(12) United States Patent
Kungl

(10) Patent No.: US 7,807,413 B2
(45) Date of Patent: Oct. 5, 2010

(54) GAG BINDING PROTEIN

(75) Inventor: Andreas J. Kungl, Graz (AT)

(73) Assignee: Protaffin Biotechnologie AG, Graz (AT)

( * ) Notice: Subject to any disclaimer, the term of this patent is extended or adjusted under 35 U.S.C. 154(b) by 323 days.

(21) Appl. No.: 12/131,311

(22) Filed: Jun. 2, 2008

(65) Prior Publication Data

US 2009/0005541 A1 Jan. 1, 2009

Related U.S. Application Data

(60) Division of application No. 11/422,169, filed on Jun. 5, 2006, now Pat. No. 7,585,937, which is a continuation of application No. PCT/EP2004/013670, filed on Dec. 2, 2004.

(30) Foreign Application Priority Data

Dec. 4, 2003 (AT) .............................. A 1952/2003

(51) Int. Cl.
C12N 15/63 (2006.01)
C12N 15/64 (2006.01)
C12N 5/10 (2006.01)

(52) U.S. Cl. ................... 435/69.51; 435/69.5; 435/71.1

(58) Field of Classification Search ........................ None
See application file for complete search history.

(56) References Cited

FOREIGN PATENT DOCUMENTS

| WO | WO 92/07935 | 5/1992 |
| WO | WO 96/34965 | 11/1996 |
| WO | WO 02/20715 | 3/2002 |

OTHER PUBLICATIONS

Brander, Translation of Klonierung, Expression und Reinigung bindungsmodifizierter Interleukin-8 Mutanten, Zur Erlangung des akademischen Grades einer, Magistra Pharmaciae, an der Naturwissenschaftlichen Fakultät der, Karl-Franzens-Universität Graz (2002).
Brandner, Klonierung, Expression und Reinigung bindungsmodifizierter Interleukin-8 Mutanten, Zur Erlangung des akademischen Grades einer, Magistra Pharmaciae, an der Naturwissenschaftlichen Fakultät der, Karl-Franzens-Universität Graz (2002) (with English Abstract).
Butcher et al., FEBS Letters 409: 183-187 (1997).
Ecker, Österreichische Apotheker-Zeitung 57(14): 658-660 (2003).
Jayaraman et al., FEBS Letters 482: 154-158 (2000).
Jinno-Oue et al., Journal of Virology 75(24): 12439-12445 (2001).
Hileman et al., BioEssays 20: 156-167 (1998).
Lortat-Jacob et al., PNAS 99(3): 1229-1234 (2002).
Verrecchio et al., The Journal of Biological Chemistry 275(11): 7701-7707 (2000).
Wong et al., The Journal of Biological Chemistry 273(29): 18617-18622 (1998).
Yang et al., Journal of Cellular Biochemistry 56: 455-468 (1994).

*Primary Examiner*—Prema Mertz
(74) *Attorney, Agent, or Firm*—Perkins Coie LLP

(57) ABSTRACT

A method is provided for introducing a GAG binding site into a protein comprising the steps:
identifying a region in a protein which is not essential for structure maintenance
introducing at least one basic amino acid into said site and/or deleting at least one bulky and/or acidic amino acid in said site,
whereby said GAG binding site has a GAG binding affinity of $Kd \leq 10$ μM, preferably $\leq 1$ μM, still preferred $\leq 0.1$ μM, as well as modified GAG binding proteins.

16 Claims, 4 Drawing Sheets

Figures 1, 2:
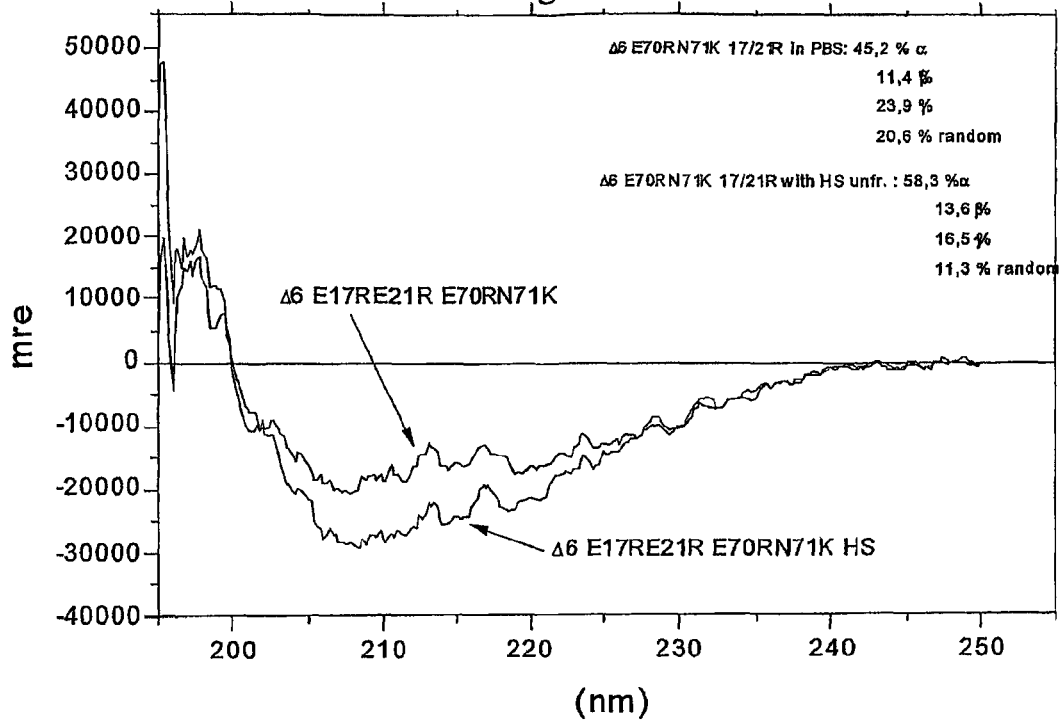

| sec. structure | IL-8Δ6 E70R | IL-8Δ6 E70R HS | IL-8Δ6 F17RF21R E70K | IL-8Δ6 F17RF21R E70K HS |
|---|---|---|---|---|
| α-helix [%] | 24,9 | 37 | 17,4 | 28,7 |
| β-sheet [%] | 23,6 | 23 | 29,8 | 22 |
| turns [%] | 20,9 | 27,3 | 25,9 | 29,7 |
| others [%] | 40,7 | 12,7 | 26,9 | 19,6 |

GAG BINDING PROTEIN

This application is a divisional of U.S. application Ser. No. 11/422,169 filed on Jun. 5, 2006, now U.S. Pat. No. 7,585,937 which is a continuation of PCT/EP2004/013670 filed on Dec. 2, 2004. The entire contents of the above-identified applications are hereby incorporated by reference.

The present invention relates to methods and tools for the inhibition of the interaction of chemokines and their high-affinity receptors on leukocytes and methods for the therapeutic treatment of inflammatory diseases.

Chemokines, originally derived from chemoattractant cytokines, actually comprise more than 50 members and represent a family of small, inducible, and secreted proteins of low molecular weight (6-12 kDa in their monomeric form) that play a decisive role during immunosurveillance and inflammatory processes. Depending on their function in immunity and inflammation, they can be distinguished into two classes. Inflammatory chemokines are produced by many different tissue cells as well as by immigrating leukocytes in response to bacterial toxins and inflammatory cytokines like IL-1, TNF and interferons. Their main function is to recruit leukocytes for host defence and in the process of inflammation. Homing chemokines, on the other hand, are expressed constitutively in defined areas of the lymphoid tissues. They direct the traffic and homing of lymphocytes and dendritic cells within the immune system. These chemokines, as illustrated by BCA-1, SDF-1 or SLC, control the relocation and recirculation of lymphocytes in the context of maturation, differentiation, activation and ensure their correct homing within secondary lymphoid organs.

Despite the large number of representatives, chemokines show remarkably similar structural folds although the sequence homology varies between 20 to 70 percent. Chemokines consist of roughly 70-130 amino acids with four conserved cysteine residues. The cysteines form two disulphide bonds (Cys 1→Cys 3, Cys 2→Cys 4) which are responsible for their characteristic three-dimensional structure. Chemotactic cytokines consist of a short amino terminal domain (3-10 amino acids) preceding the first cysteine residue, a core made of β-strands and connecting loops found between the second and the fourth cysteine residue, as well as a carboxy-terminal α-helix of 20-60 amino acids. The protein core has a well ordered structure whereas the N- and C-terminal parts are disordered. As secretory proteins they are synthesised with a leader sequence of 20-25 amino acids which is cleaved off before release.

The chemokines have been subdivided into four families on the basis of the relative position of their cysteine residues in the mature protein. In the α-chemokine subfamily, the first two of the four cysteines are separated by a single amino acid (CXC), whereas in the β-chemokines the corresponding cysteine residues are adjacent to each other (CC). The α-chemokines can be further classified into those that contain the ELR sequence in the N-terminus, thereby being chemotactic for neutrophils (IL-8 for example), and those that lack the ELR motif and act on lymphocytes (I-TAC for example). Structurally the β-chemokines can be subdivided into two families: the monocyte-chemoattractant protein eotaxin family, containing the five monocyte chemoattractant proteins (MCP) and eotaxin which are approximately 65 percent identical to each other, and the remaining β-chemokines. As with the CXC-family, the N-terminal amino acids preceding the CC-residues are critical components for the biologic activity and leukocyte selectivity of the chemokines. The β-chemokines, in general, do not act on neutrophils but attract monocytes, eosinophils, basophils and lymphocytes with variable selectivity.

Only a few chemokines do not fit into the CC- or the CXC-family. Lymphotactin is so far the only chemokine which shows just two instead of the four characteristic cysteines in its primary structure, and is thus classified as γ- or C-chemokine. On the other hand, by concluding this classification, fractalkine has to be mentioned as the only representative of the δ- or CXXXC-subfamily with three amino acids separating the first two cysteines. Both of them, Lymphotaxin and fractalkine, induce chemotaxis of T-cells and natural killer cells.

Chemokines induce cell migration and activation by binding to specific cell surface, seven transmembrane-spanning (7TM) G-protein-coupled receptors on target cells. Eighteen chemokine receptors have been cloned so far including six CXC, ten CC, one CX3C and one XC receptor. Chemokine receptors are expressed on different types of leukocytes, some of them are restricted to certain cells (e.g. CXCR1 is restricted to neutrophils) whereas others are more widely expressed (e.g. CCR2 is expressed on monocytes, T cells, natural killer cells and basophils). Similar to chemokines, the receptors can be constitutively expressed on certain cells, whereas some are inducible. Some of them can even be down-regulated making the cells unresponsive to a certain chemokine but remaining responsive to another. Most receptors recognise more than one chemokine and vice versa but recognition is restricted to chemokines of the corresponding subfamily (see Table 1).

TABLE 1

| Chemokine | | Receptor | Chemotactic for | Inflammatory Diseases |
|---|---|---|---|---|
| CXC-Chemokine (+ELR-motif) | IL-8 | CXCR1 CXCR2 | Neutrophils | Acute respiratory distress syndrome [71]; Bacterial pneumonia [72]; Rheumathoid arthritis [73]; Inflammatory bowel disease [74]; Psoriasis [75]; Bacterial meningitis [76] |
| CC-Chemokine | MCP-1 | CCR2 | Basophils; Monocytes; Activated T cells; Dentritic cells; Natural killer cells | Asthma [77]; Glomerulonephritis [78]; Atheroscleosis [79]; Inflammatory bowel disease [80]; Psoriasis [81]; Bacterial and viral meningitis [82, 83] |

TABLE 1-continued

| Chemokine | Receptor | Chemotactic for | Inflammatory Diseases |
|---|---|---|---|
| RANTES | CCR1 | Eosinophils; Monocytes; Activated T cells; Dentritic cells | Asthma [84]; Glomerulonephritis [85] |
| | CCR3 | Eosinophils; Basophils; Dentritic cells | |
| | CCR5 | Monocytes; Activated T cells; Dentritic cells; Natural killer cells | |

Chemokines have two main sites of interaction with their receptors, one in the amino-terminal domain and the other within an exposed loop of the backbone that extends between the second and the third cysteine residue. Both sites are kept in close proximity by the disulphide bonds. The receptor recognises first the binding site within the loop region which appears to function as a docking domain. This interaction restricts the mobility of the chemokine thus facilitating the proper orientation of the amino-terminal domain. Studies have been performed with mutant chemokines that still bound effectively to their receptors but did not signal. These mutants were obtained by amino acid deletion or modification within the N-termini of, for example, IL-8, RANTES and MCP-1.

Multiple intracellular signalling pathways occur after receptor activation as a result of chemokine binding. Chemokines also interact with two types of nonsignalling molecules. One is the DARC receptor which is expressed on erythrocytes and on endothelial cells and which binds CC- as well as CXC-chemokines to prevent them from circulation. The second type are heparan sulphate glycosaminoglycans (GAGs) which are part of proteoglycans and which serve as co-receptors of chemokines. They capture and present chemokines on the surface of the homing tissue (e.g. endothelial cells) in order to establish a local concentration gradient. In an inflammatory response, such as in rheumatoid arthritis, leukocytes rolling on the endothelium in a selectin-mediated process are brought into contact with the chemokines presented by the proteoglycans on the cell surface. Thereby, leukocyte integrins become activated which leads to firm adherence and extravasation. The recruited leukocytes are activated by local inflammatory cytokines and may become desensitised to further chemokine signalling because of high local concentration of chemokines. For maintaining a tissue bloodstream chemokine gradient, the DARC receptor functions as a sink for surplus chemokines.

Heparan sulphate (HS) proteoglycans, which consist of a core protein with covalently attached glycosaminoglycan sidechains (GAGs), are found in most mammalian cells and tissues. While the protein part determines the localisation of the proteoglycan in the cell membrane or in the extracellular matrix, the glycosaminoglycan component mediates interactions with a variety of extracellular ligands, such as growth factors, chemokines and adhesions molecules. The biosynthesis of proteoglycans has previously been extensively reviewed. Major groups of the cell surface proteoglycans are the syndecan family of transmembrane proteins (four members in mammals) and the glypican family of proteins attached to the cell membrane by a glycosylphosphatidylinositol (GPI) tail (six members in mammals). While glypicans are expressed widely in the nervous system, in kidney and, to a lesser extent, in skeletal and smooth muscle, syndecan-1 is the major HSPG in epithelial cells, syndecan-2 predominates in fibroblasts and endothelial cells, syndecan-3 abounds in neuronal cells and syndecan-4 is widely expressed. The majority of the GAG chains added to the syndecan core proteins through a tetrasaccharide linkage region onto particular serines are HS chains. Although the amino acid sequences of the extracellular domains of specific syndecan types are not conserved among different species, contrary to the transmembrane and the cytoplasmic domains, the number and the positions of the GAG chains are highly conserved. The structure of the GAGs, however, is species-specific and is, moreover, dependent upon the nature of the HSPG-expressing tissue.

Heparan sulphate (HS) is the most abundant member of the glycosaminoglycan (GAG) family of linear polysaccharides which also includes heparin, chondroitin sulphate, dermatan sulphate and keratan sulphate. Naturally occurring HS is characterised by a linear chain of 20-100 disaccharide units composed of N-acetyl-D-glucosamine (GlcNAc) and D-glucuronic acid (GlcA) which can be modified to include N- and O-sulphation (6-0 and 3-0 sulphation of the glucosamine and 2-0 sulphation of the uronic acid) as well as epimerisation of β-D-gluronic acid to α-L-iduronic acid (IdoA).

Clusters of N- and O-sulphated sugar residues, separated by regions of low sulphation, are assumed to be mainly responsible for the numerous protein binding and regulatory properties of HS. In addition to the electrostatic interactions of the HS sulphate groups with basic amino acids, van der Waals and hydrophobic interactions are also thought to be involved in protein binding. Furthermore, the presence of the conformationally flexible iduronate residues seems to favour GAG binding to proteins. Other factors such as the spacing between the protein binding sites play also a critical role in protein-GAG binding interactions: For example γ-interferon dimerisation induced by HS requires GAG chains with two protein binding sequences separated by a 7 kDa region with low sulphation. Additional sequences are sometimes required for full biological activity of some ligands: in order to support FGF-2 signal transduction, HS must have both the minimum binding sequence as well as additional residues that are supposed to interact with the FGF receptor.

Heparin binding proteins often contain consensus sequences consisting of clusters of basic amino acid residues. Lysine, arginine, asparagine, histidine and glutamine are frequently involved in electrostatic contacts with the sulphate and carboxyl groups on the GAG. The spacing of the basic amino acids, sometimes determined by the proteins 3-D structure, are assumed to control the GAG binding specificity and affinity. The biological activity of the ligand can also be affected by the kinetics of HS-protein interaction. Reducing the dimension of growth factor diffusion is one of the suggested HSPG functions for which the long repetitive character of the GAG chains as well as their relatively fast on and off rates of protein binding are ideally suited. In some cases, kinetics rather than thermodynamics drives the physiological function of HS-protein binding. Most HS ligands require GAG sequences of well-defined length and structure. Heparin, which is produced by mast cells, is structurally very similar to heparan sulphate but is characterised by higher levels of post-polymerisation modifications resulting in a uniformly high degree of sulphation with a relatively small degree of structural diversity. Thus, the highly modified blocks in heparan sulphate are sometimes referred to as "heparin-like". For this reason, heparin can be used as a perfect HS analogue for protein biophysical studies as it is, in addition, available in larger quantities and therefore less expensive than HS. Different cell types have been shown to synthesise proteoglycans with different glycosaminoglycan structure which changes during pathogenesis, during development or in response to extracellular signals such as growth factors. This structural diversity of HSPGs leads to a high binding versatility emphasising the great importance of proteoglycans.

Since the demonstration that heparan sulphate proteoglycans are critical for FGF signalling, several investigations were performed showing the importance of chemokine-GAG binding for promoting chemokine activity. First, almost all chemokines studied to date appear to bind HS in vitro, suggesting that this represents a fundamental property of these proteins. Second, the finding that in vivo T lymphocytes secrete CC-chemokines as a complex with glycosaminoglycans indicates that this form of interaction is physiologically relevant. Furthermore, it is known that the association of chemokines with HS helps to stabilise concentration gradients across the endothelial surface thereby providing directional information for migrating leukocytes. HS is also thought to protect chemokines from proteolytic degradation and to induce their oligomerisation thus promoting local high concentrations in the vicinity of the G-coupled signalling receptors. The functional relevance of oligomerisation, however, remains controversial although all chemokines have a clear structural basis for multimerisation. Dimerisation through association of the β-sheets is observed for all chemokines of the CXC-family (e.g. IL-8), contrary to most members of the CC-chemokine family (e.g. RANTES), which dimerise via their N-terminal strands.

A wealth of data has been accumulated on the inhibition of the interaction of chemokines and their high-affinity receptors on leukocytes by low molecular weight compounds. However, there has been no breakthrough in the therapeutic treatment of inflammatory diseases by this approach.

Interleukin-8 (IL-8) is a key molecule involved in neutrophil attraction during chronic and acute inflammation. Several approaches have been undertaken to block the action of IL-8 so far, beginning with inhibition of IL-8 production by for example glucocorticoids, Vitamin D3, cyclosporin A, transforming growth factor β, interferons etc., all of them inhibiting IL-8 activity at the level of production of IL-8 mRNA. A further approach previously used is to inhibit the binding of IL-8 to its receptors by using specific antibodies either against the receptor on the leukocyte or against IL-8 itself in order to act as specific antagonists and therefore inhibiting the IL-8 activity.

The aim of the present invention is therefore to provide an alternative strategy for the inhibition or disturbance of the interaction of chemokines/receptors on leukocytes. Specifically the action of IL-8, RANTES or MCP-1 should be targeted by such a strategy.

Subject matter of the present invention is therefore a method to produce new GAG binding proteins as well as alternative GAG binding proteins which show a high(er) affinity to a GAG co-receptor (than the wild type). Such modified GAG binding proteins can act as competitors with wild-type GAG binding proteins and are able to inhibit or down-regulate the activity of the wild-type GAG binding protein, however without the side effects which occur with the known recombinant proteins used in the state of the art. The molecules according to the present invention do not show the above mentioned disadvantages. The present modified GAG binding proteins can be used in drugs for various therapeutical uses, in particular—in the case of chemokines—for the treatment of inflammation diseases without the known disadvantages which occur in recombinant chemokines known in the state of the art. The modification of the GAG binding site according to the present invention turned out to be a broadly applicable strategy for all proteins which activity is based on the binding event to this site, especially chemokines with a GAG site. The preferred molecules according to the present invention with a higher GAG binding affinity proved to be specifically advantageous with respect to their biological effects, especially with respect to their anti-inflammatory activity by their competition with wild type molecules for the GAG site.

Therefore, the present invention provides a method for introducing a GAG binding site into a protein characterised in that it comprises the steps:

- identifying a region in a protein which is not essential for structure maintenance
- introducing at least one basic amino acid into said site and/or deleting at least one bulky and/or acidic amino acid in said site, whereby said GAG binding site has a GAG binding affinity of $K_d \leqq 10$ μM, preferably $\leqq 1$ μM, still preferred $\leqq 0.1$ μM. By introducing at least one basic amino acid and/or deleting at least one bulky and/or acidic amino acid in said region, a novel, improved "artificial" GAG binding site is introduced in said protein. This comprises the new, complete introduction of a GAG binding site into a protein which did not show a GAG binding activity before said modification. This also comprises the introduction of a GAG binding site into a protein which already showed GAG binding activity. The new GAG binding site can be introduced into a region of the protein which did not show GAG binding affinity as well as a region which did show GAG binding affinity. However, with the most preferred embodiment of the present invention, a modification of the GAG binding affinity of a given GAG binding protein is provided, said modified protein's GAG binding ability is increased compared to the wild-type protein. The present invention relates to a method of introducing a GAG binding site into a protein, a modified GAG binding protein as well as to an isolated DNA molecule, a vector, a recombinant cell, a pharmaceutical composition and the use of said modified protein.

BRIEF DESCRIPTION OF THE DRAWINGS

FIG. 1 shows a CD spectra.

FIG. 2 shows secondary structure contents of various mutants.

FIG. 3 shows graphics of results from fluorescence anisotropy tests of various mutants.

FIG. 4 shows graphics of results from fluorescence anisotropy tests of two mutants.

FIG. 5 shows the graphic of results from isothermal fluorescence titrations.

FIG. 6 shows the graphic of results from unfolding experiments of various mutants.

FIG. 7 shows chemotaxis index of IL-8 mutants.

FIG. 8 shows the results of the RANTES chemotaxis assay.

The term "introducing at least one basic amino acid" relates to the introduction of additional amino acids as well as the substitution of amino acids. The main purpose is to increase the relative amount of basic amino acids, preferably Arg, Lys, His, Asn and/or Gln, compared to the total amount of amino acids in said site, whereby the resulting GAG binding site should preferably comprise at least 3 basic amino acids, still preferred 4, most preferred 5 amino acids.

The GAG binding site is preferably at a solvent exposed position, e.g. at a loop. This will assure an effective modification.

Whether or not a region of a protein is essential for structure maintenance, can be tested for example by computational methods with specific programmes known to the person skilled in the art. After modification of the protein, the conformational stability is preferably tested in silico.

The term "bulky amino acid" refers to amino acids with long or sterically interfering side chains; these are in particular Trp, Ile, Leu, Phe, Tyr. Acidic amino acids are in particular Glu and Asp. Preferably, the resulting GAG binding site is free of bulky and acidic amino acids, meaning that all bulky and acidic amino acids are removed.

The GAG binding affinity is determined—for the scope of protection of the present application—over the dissociation constant $K_d$. One possibility is to determine the dissociation constant ($K_d$) values of any given protein by the structural change in ligand binding. Various techniques are well known to the person skilled in the art, e.g. isothermal fluorescence titrations, isothermal titration calorimetry, surface plasmon resonance, gel mobility assay, and indirectly by competition experiments with radioactively labelled GAG ligands. A further possibility is to predict binding regions by calculation with computational methods also known to the person skilled in the art, whereby several programmes may be used.

A protocol for introducing a GAG binding site into a protein is for example as follows:
- Identify a region of the protein which is not essential for overall structural maintenance and which might be suitable for GAG binding
- Design a new GAG binding site by introducing (replacement or insertion) basic Arg, Lys, His, Asp and Gln residues at any position or by deleting amino acids which interfere with GAG binding
- Check the conformational stability of the resulting mutant protein in silico
- Clone the wild-type protein cDNA (alternatively: purchase the cDNA)
- Use this as template for PCR-assisted mutagenesis to introduce the above mentioned changes into the amino acid sequence
- Subclone the mutant gene into a suitable expression system (prokaryotic or eukaryotic dependent upon biologically required post-translational modifications)
- Expression, purification and characterisation of the mutant protein in vitro
- Criterion for an introduced GAG binding affinity: $K_d^{GAG}$ (mutant) <10 µM.

Examples of said engineered proteins with new GAG binding sites are for example the Fc part of IgG as well as the complement factors C3 and C4 modified as follows:

```
Fc:
(439) KSLSLS (444) -> KSKKLS     (SEQ ID NOS 1 & 2)

C3:
(1297) WIASHT (1302) -> WKAKHK   (SEQ ID NOS 3 & 4)

C4:
(1) MLDAERLK (8) -> MKKAKRLK     (SEQ ID NOS 5 & 6)
```

A further aspect of the present invention is a protein obtainable by the inventive method as described above. The inventive protein therefore comprises a—compared to the wild-type protein—new GAG binding site as defined above and will therefore act as competitor with natural GAG binding proteins, in particular since the GAG binding affinity of the inventive protein is very high, e.g. $K_d \leq 10$ µM.

A further aspect of the present invention is a modified GAG binding protein, whereby a GAG binding region in said protein is modified by substitution, insertion, and/or deletion of at least one amino acid in order to increase the relative amount of basic amino acids in said GAG binding region, and/or reduce the amount of bulky and/or acidic amino acids in said GAG binding region, preferably at a solvent exposed position, and in that the GAG binding affinity of said protein is increased compared to the GAG binding affinity of a respective wild-type protein.

It has been surprisingly shown that by increasing the relative amount of basic amino acids, in particular Arg, Lys, His, Asn and Gln, in the GAG binding region, the modified GAG binding protein shows increased GAG binding affinity compared to the wild-type proteins, in particular when the relative amount of basic amino acids is increased at a solvent exposed position, since a positively charged area on the protein surface has shown to enhance the binding affinity. Preferably, at least 3, still preferred 4, most preferred 5, basic amino acids are present in the GAG binding region.

The term "GAG binding protein" relates to any protein which binds to a GAG co-receptor. Whether or not a protein binds to a GAG co-receptor can be tested with the help of known protocols as mentioned above. Hileman et al. (BioEssays 20 (1998), 156-167) disclose consensus sites in glycosaminoglycan binding proteins. The information disclosed in this article is also useful as starting information for the present invention. The term "protein" makes clear that the molecules provided by the present invention are at least 80 amino acids in length. This is required for making them suitable candidates for the present anti-inflammation strategy. Smaller molecules interacting with a GAG binding site and being physiologically or pathologically relevant due to such an interaction are not known and therefore not relevant for the present invention. Preferably, the molecules according to the present invention are composed of at least 90, at least 100, at least 120, at least 150, at least 200, at least 300, at least 400 or at least 500 amino acid residues.

In the scope of the present application the term "GAG binding region" is defined as a region which binds to GAG with a dissociation constant ($K_d$-value) of under 100 µM, preferably under 50 µM, still preferred under 20 µM, as determined by isothermal fluorescence titration (see examples below).

Any modifications mentioned in the present application can be carried out with known biochemical methods, for example site-directed mutagenesis. It should also be noted that molecular cloning of GAG binding sites is, of course, prior art (see e.g. WO96/34965 A, WO 92/07935 A, Jayaraman et al. (FEBS Letters 482 (2000), 154-158), WO02/20715 A, Yang et al. (J. Cell. Biochem. 56 (1994), 455-468), wherein molecular shuffling or de novo synthesis of GAG regions are described; Butcher et al., (FEBS Letters 4009 (1997), 183-187) (relates to artificial peptides, not proteins); Jinno-Oue et al, (J. Virol. 75 (2001), 12439-12445) de novo synthesis)).

The GAG binding region can be modified by substitution, insertion and/or deletion. This means that a non-basic amino acid may be substituted by a basic amino acid, a basic amino acid may be inserted into the GAG binding region or a non-basic amino acid may be deleted. Furthermore, an amino acid which interferes with GAG binding, preferably all interfering amino acids binding is deleted. Such amino acids are in particular bulky amino acids as described above as well as acidic amino acids, for example Glu and Asp. Whether or not an amino acid interferes with GAG binding may be examined with for example mathematical or computational methods. The result of any of these modifications is that the relative amount of basic amino acids in said GAG binding region is increased, whereby "relative" refers to the amount of basic amino acids in said GAG binding region compared to the number of all amino acids in said GAG binding region. Furthermore, amino acids which interfere sterically or electrostatically with GAG binding are deleted.

Whether or not an amino acid is present in a solvent exposed position, can be determined for example with the help of the known three dimensional structure of the protein or with the help of computational methods as mentioned above.

Whether or not the GAG binding affinity of said modified protein is increased compared to the GAG binding affinity of the respective wild-type protein, can be determined as mentioned above with the help of, for example, fluorescence titration experiments which determine the dissociation constants. The criterion for improved GAG binding affinity will be $K_d$ (mutant)<$K_d$ (wild-type), preferably by at least 100%. Specifically improved modified proteins have—compared with wild-type $K_d$—a GAG binding affinity which is higher by a factor of minimum 5, preferably of minimum 10, still preferred of minimum 100. The increased GAG binding affinity will therefore preferably show a $K_d$ of under 10 µM, preferred under 1 µM, still preferred under 0.1 µM.

By increasing the GAG binding affinity the modified protein will act as a specific antagonist and will compete with the wild-type GAG binding protein for the GAG binding.

Preferably, at least one basic amino acid selected from the group consisting of Arg, Lys, and His is inserted into said GAG binding region. These amino acids are easily inserted into said GAG binding region, whereby the term "inserted" relates to an insertion as such as well as substituting any non-basic amino acid with arginine, lysine or histidine. Of course, it is possible to insert more than one basic amino acid whereby the same basic amino acid may be inserted or also a combination of two or three of the above mentioned amino acids.

Still preferred, the protein is a chemokine, preferably IL-8, RANTES or MCP-1. Chemokines are known to have a site of interaction with co-receptor GAG whereby this chemokine binding is often a condition for further receptor activation as mentioned above. Since chemokines are often found in inflammatory diseases, it is of major interest to block the chemokine receptor activation. Such chemokines are preferably IL-8, RANTES or MCP-1, which are well characterised molecules and of which the GAG binding regions are well known (see, for example, Lortat-Jacob et al., PNAS 99 (3) (2002), 1229-1234). By increasing the amount of basic amino acids in the GAG binding region of these chemokines, their binding affinity is increased and therefore the wild-type chemokines will bind less frequently or not at all, depending on the concentration of the modified protein in respect to the concentration of the wild-type protein.

According to an advantageous aspect, said GAG binding region is a C terminal α-helix. A typical chemical monomer is organised around a triple stranded anti-parallel β-sheet overlaid by a C-terminal α-helix. It has been shown that this C-terminal α-helix in chemokines is to a major part involved in the GAG binding, so that modification in this C-terminal α-helix in order to increase the amount of basic amino acids results in a modified chemokine with an increased GAG binding affinity.

Advantageously, positions 17, 21, 70, and/or 71 in IL-8 are substituted by Arg, Lys, His, Asn and/or Gln. Here it is possible that only one of these aforementioned sites is modified. However, also more than one of these sites may be modified as well as all, whereby all modifications may be either Arg or Lys or His or Asn or Gln or a mixture of those. In IL-8 these positions have shown to highly increase the GAG binding affinity of IL-8 and therefore these positions are particularly suitable for modifications.

Preferably the increased binding affinity is an increased binding affinity to heparan sulphate and/or heparin. Heparan sulphate is the most abundant member of the GAG family of linear polysaccharides which also includes heparin. Heparin is structurally very similar to heparan sulphate characterised by higher levels of post-polymerisation modifications resulting in a uniformly high degree of sulphation with a relatively small degree of structural diversity. Therefore, the highly modified blocks in heparan sulphate are sometimes referred to as heparin-like and heparin can be used as a heparan sulphate analogue for protein biophysical studies. In any case, both, heparan sulphate and heparin are particularly suitable.

Still preferred, a further biologically active region is modified thereby inhibiting or down-regulating a further biological activity of said protein. This further biological activity is known for most GAG binding proteins, for example for chemokines. This will be the binding region to a receptor, for example to the 7TM receptor. The term "further" defines a biologically active region which is not the GAG binding region which, however, binds to other molecules, cells or receptors and/or activates them. By modifying this further biologically active region the further biological activity of this protein is inhibited or down-regulated and thereby a modified protein is provided which is a strong antagonist to the wild-type protein. This means that on the one hand the GAG binding affinity is higher than in the wild-type GAG binding protein, so that the modified protein will to a large extent bind to the GAG instead of the wild-type protein. On the other hand, the further activity of the wild-type protein which mainly occurs when the protein is bound to GAG, is inhibited or down-regulated, since the modified protein will not carry out this specific activity or carries out this activity to a lesser extent. With this modified protein an effective antagonist for wild-type GAG binding proteins is provided which does not show the side effects known from other recombinant proteins as described in the state of the art. This further biologically active region can for example be determined in vitro by receptor competition assays (using fluorescently labelled wt chemokines, calcium influx, and cell migration (performed on native leukocytes or on 7TM stably-transfected cell lines). Examples of such further biologically active regions are, in addition to further receptor binding sites (as in the growth factor family), enzymatic sites (as in hydrolases, lyases, sulfotransferases, N-deacetylases, and copolymerases), protein interaction sites (as in antithrombin III), and membrane binding domains (as in the herpes simplex virus gD protein). With this preferred embodiment of double-modified proteins therefore dominant (concerning GAG binding) negative (concerning receptor) mutants are provided which are specifically advantageous with respect to the objectives set for the present invention.

Still preferred, said further biologically active region is modified by deletion, insertion, and/or substitution, preferably with alanine, a sterically and/or electrostatically similar residue. It is, of course, possible to either delete or insert or substitute at least one amino acid in said further biologically active region. However, it is also possible to provide a combination of at least two of these modifications or all three of them. By substituting a given amino acid with alanine or a sterically/electronically similar residue—"similar" meaning similar to the amino acid being substituted—the modified protein is not or only to a lesser extent modified sterically/electrostatically. This is particularly advantageous, since other activities of the modified protein, in particular the affinity to the GAG binding region, are not changed.

Advantageously, said protein is a chemokine and said further biological activity is leukocyte activation. As mentioned above, chemokines are involved in leukocyte attraction during chronic and acute inflammation. Therefore, by inhibiting or down-regulating leukocyte activation inflammation is decreased or inhibited which makes this particular modified protein an important tool for studying, diagnosing and treating inflammatory diseases.

According to an advantageous aspect, said protein is IL-8 and said further biologically active region is located within the first 10 N-terminal amino acids. The first N-terminal amino acids are involved in leukocyte activation, whereby in particular Glu-4, Leu-5 and Arg-6 were identified to be essential for receptor binding and activation. Therefore, either these three or even all first 10 N-terminal amino acids can be substituted or deleted in order to inhibit or down-regulate the receptor binding and activation.

A further advantageous protein is an IL-8 mutant with the first 6 N-terminal amino acids deleted. As mentioned above, this mutant will not or to a lesser extent bind and activate leukocytes, so that it is particularly suitable for studying, diagnosing and treating inflammatory diseases.

Preferably, said protein is an IL-8 mutant selected from the group consisting of del6F17RE70KN71R, del6F17RE70RN71K and del6E70KN71K. These mutants have shown to be particularly advantageous, since the deletion of the first 6 N-terminal amino acids inhibits or down-regulates receptor binding and activation. Furthermore, the two phenylalanines in position 17 and 21 were found to make first contact with the receptor on its N-terminal extracellular domain to facilitate the later activation of the receptor. In order to prevent any neutrophil contact, these two amino acids 17 and 21 are exchanged, whereby they are exchanged to basic amino acids, since they are in close proximity to the GAG binding motif of the C-terminal α-helix as can be seen on a three dimensional model of a protein. By exchanging the position 17 and/or 21 to either arginine or lysine the GAG binding affinity is therefore increased.

A further aspect of the present invention is an isolated polynucleic acid molecule which codes for the inventive protein as described above. The polynucleic acid may be DNA or RNA. Thereby the modifications which lead to the inventive modified protein are carried out on DNA or RNA level. This inventive isolated polynucleic acid molecule is suitable for diagnostic methods as well as gene therapy and the production of inventive modified protein on a large scale.

Still preferred, the isolated polynucleic acid molecule hybridises to the above defined inventive polynucleic acid molecule under stringent conditions. Depending on the hybridisation conditions complementary duplexes form between the two DNA or RNA molecules, either by perfectly being matched or also comprising mismatched bases (see Sambrook et al., Molecular Cloning: A laboratory manual, $2^{nd}$ ed., Cold Spring Harbor, N.Y. 1989). Probes greater in length than about 50 nucleotides may accommodate up to 25 to 30% mismatched bases. Smaller probes will accommodate fewer mismatches. The tendency of a target and probe to form duplexes containing mismatched base pairs is controlled by the stringency of the hybridisation conditions which itself is a function of factors, such as the concentration of salt or formamide in the hybridisation buffer, the temperature of the hybridisation and the post-hybridisation wash conditions. By applying well-known principles that occur in the formation of hybrid duplexes conditions having the desired stringency can be achieved by one skilled in the art by selecting from among a variety of hybridisation buffers, temperatures and wash conditions. Thus, conditions can be selected that permit the detection of either perfectly matched or partially mismatched hybrid duplexes. The melting temperature (Tm) of a duplex is useful for selecting appropriate hybridisation conditions. Stringent hybridisation conditions for polynucleotide molecules over 200 nucleotides in length typically involve hybridising at a temperature 15-25° C. below the melting temperature of the expected duplex. For oligonucleotide probes over 30 nucleotides which form less stable duplexes than longer probes, stringent hybridisation usually is achieved by hybridising at 5 to 10° C. below the Tm. The Tm of a nucleic acid duplex can be calculated using a formula based on the percent G+C contained in the nucleic acids and that takes chain lengths into account, such as the formula $Tm=81.5-16.6(\log[Na^+)])+0.41(\%\ G+C)-(600/N)$, where N=chain length.

A further aspect of the present invention relates to a vector which comprises an isolated DNA molecule according to the present invention as defined above. The vector comprises all regulatory elements necessary for efficient transfection as well as efficient expression of proteins. Such vectors are well known in the art and any suitable vector can be selected for this purpose.

A further aspect of the present application relates to a recombinant cell which is stably transfected with an inventive vector as described above. Such a recombinant cell as well as any therefrom descendant cell comprises the vector. Thereby a cell line is provided which expresses the modified protein either continuously or upon activation depending on the vector.

A further aspect of the present invention relates to a pharmaceutical composition which comprises a protein, a polynucleic acid or a vector according to the present invention as defined above and a pharmaceutically acceptable carrier. Of course, the pharmaceutical composition may further comprise additional substances which are usually present in pharmaceutical compositions, such as salts, buffers, emulgators, colouring agents, etc.

A further aspect of the present invention relates to the use of the modified protein, a polynucleic acid or a vector according to the present invention as defined above in a method for inhibiting or supressing the biological activity of the respective wild-type protein. As mentioned above, the modified protein will act as an antagonist whereby the side effects which occur with known recombinant proteins will not occur with the inventive modified protein. In the case of chemokines this will be in particular the biological activity involved in inflammatory reactions.

Therefore, a further use of the modified protein, polynucleic acid or vector according to the present invention is in a method for producing a medicament for the treatment of an inflammatory condition. In particular, if the modified protein is a chemokine, it will act as antagonist without side effects and will be particularly suitable for the treatment of an inflammatory condition. Therefore, a further aspect of the present application is also a method for the treatment of an inflammatory condition, wherein a modified protein according to the present invention, the isolated polynucleic acid molecule or vector according to the present invention or a pharmaceutical composition according to the present invention is administered to a patient.

Preferably, the inflammatory condition is selected from a group comprising rheumatoid arthritis, psoriasis, osteoarthritis, asthma, Alzheimer's disease, and multiple sclerosis. Since the activation through chemokines can be inhibited with a modified protein according to the present invention, inflammatory reactions can be inhibited or down-regulated whereby the above mentioned inflammatory conditions can be prevented or treated.

Figure 3:
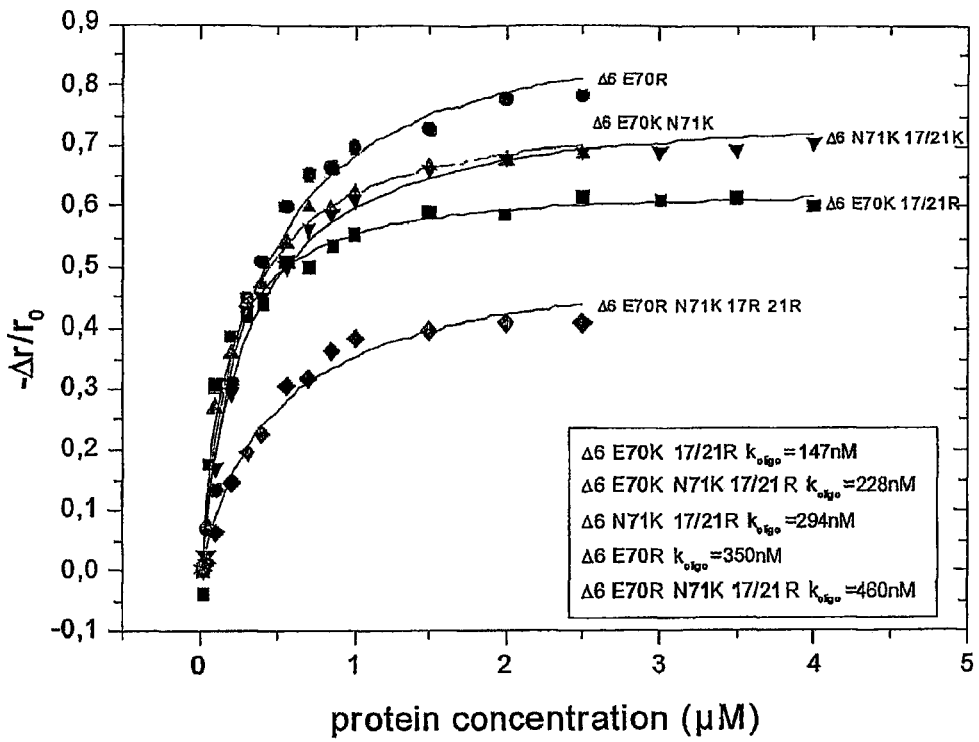
Figure 4:
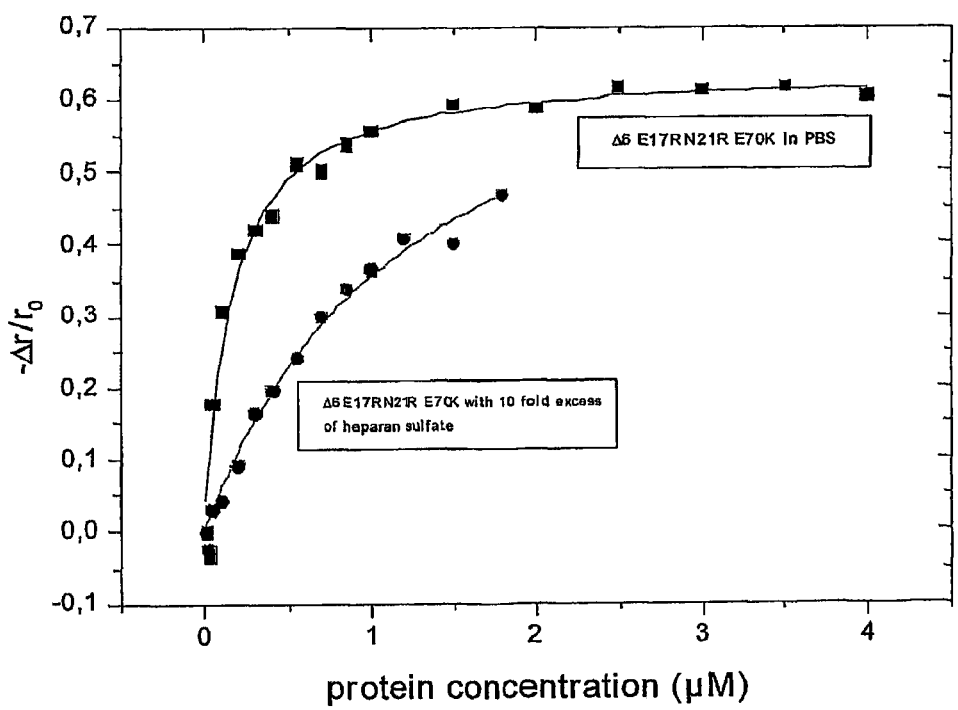
Figure 5:
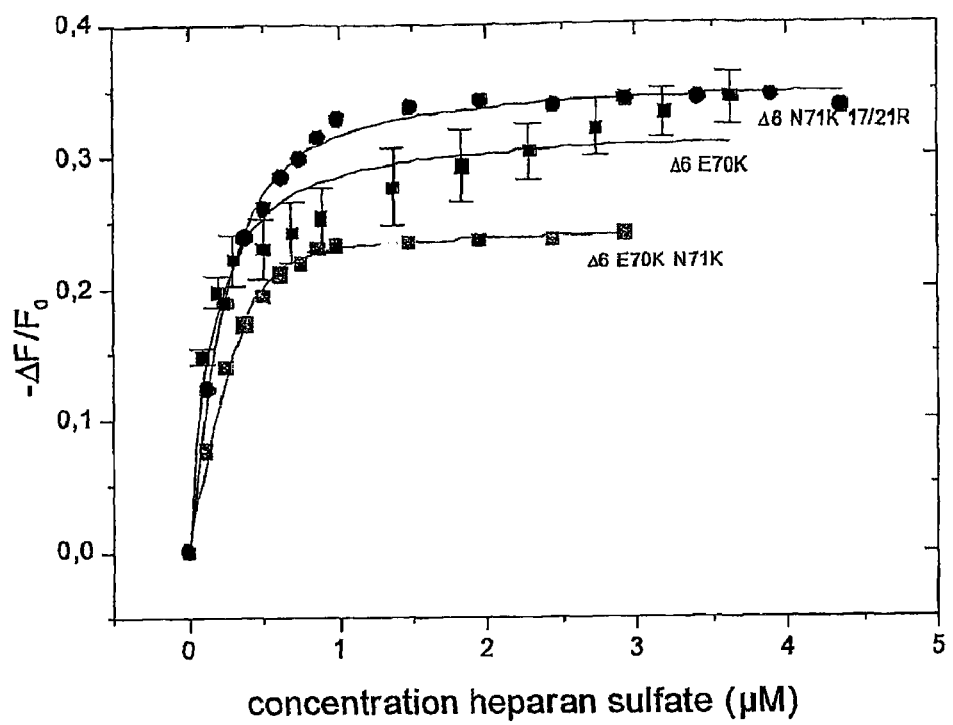
Figure 6:
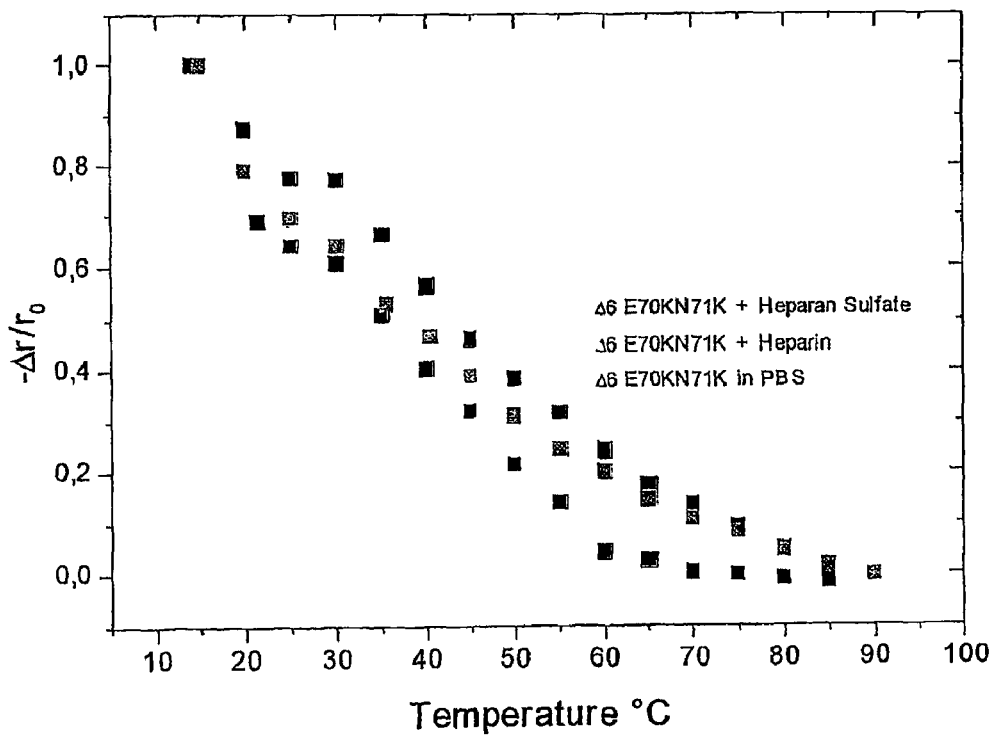
Figure 7:
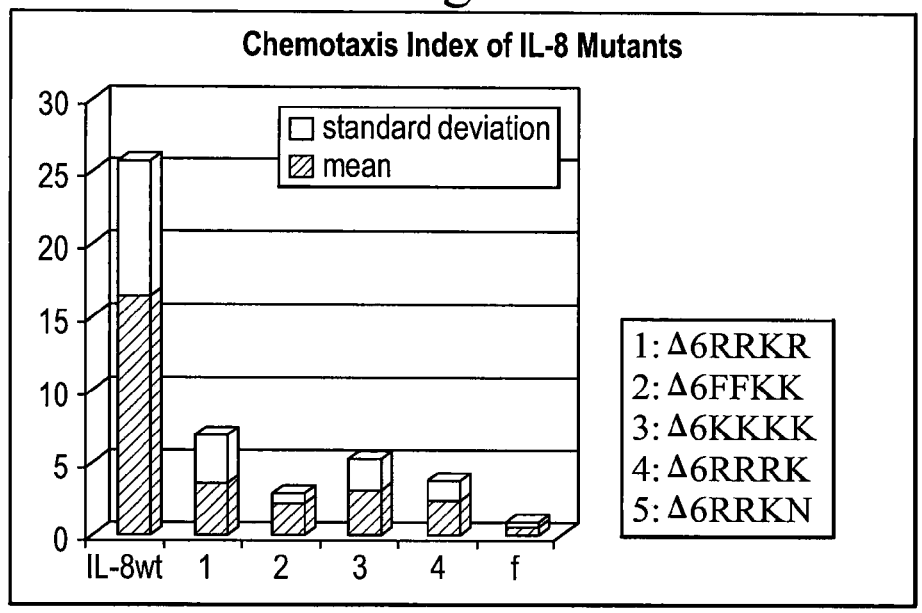
Figure 8:
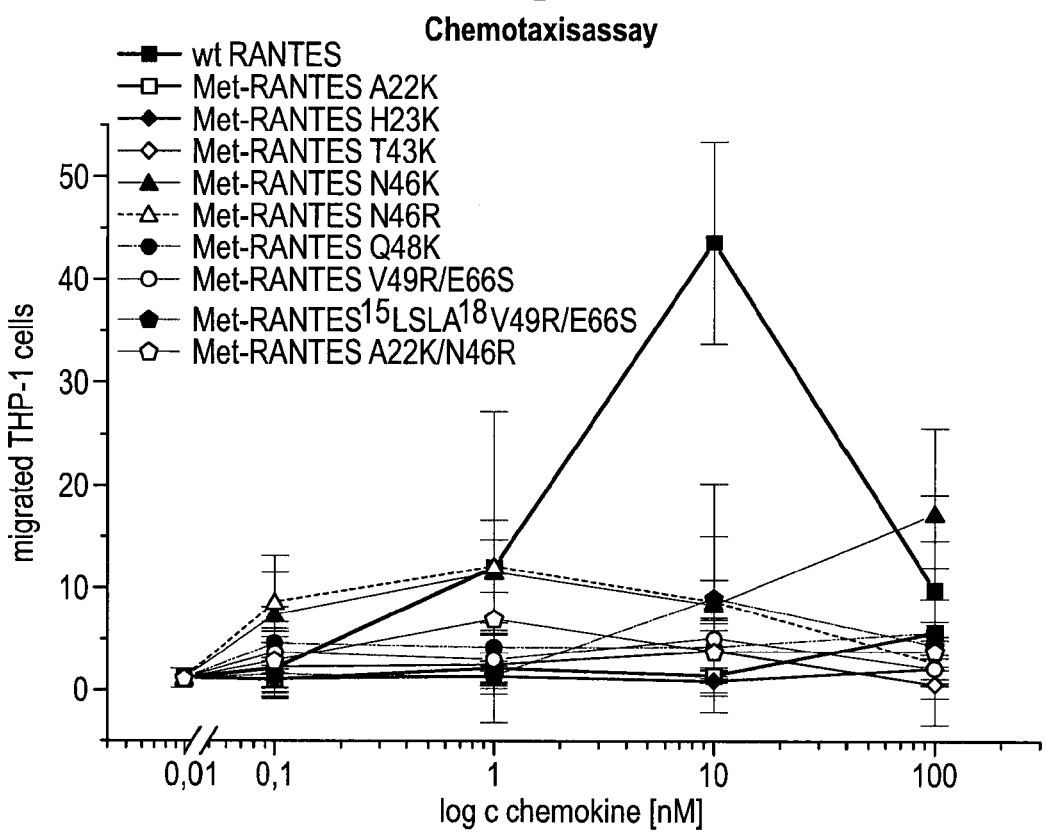

The present invention is described in further detail with the help of the following examples and figures to which the invention is, however, not limited whereby FIG. 1 is a CD spectra; FIG. 2 shows secondary structure contents of various mutants; FIGS. 3 and 4 show graphics of results from fluorescence anisotropy tests of various mutants; FIG. 5 shows the graphic of results from isothermal fluorescence titrations; FIG. 6 shows the graphic of results from unfolding experiments of various mutants, FIG. 7 shows chemotaxis index of IL-8 mutants (SEQ ID NOS 1070-1074 are disclosed respectively in order of appearance), and FIG. 8 shows the results of the RANTES chemotaxis assay.

EXAMPLES

Example 1

Generation of Recombinant IL-8 Genes and Cloning of the Mutants

Polymerase chain reaction (PCR) technique was used to generate the desired cDNAs for the mutants by introducing the mutations using sense and antisense mutagenesis primers. A synthetic plasmid containing the cDNA for wtIL-8 was used as template, Clontech Advantage®2 Polymerase Mix applied as DNA polymerase and the PCR reaction performed using a Mastergradient Cycler of Eppendorf. The mutagenesis primers used are summarised in the table below beginning with the forward sequences (5' to 3'):

```
                                          (SEQ ID NO: 7)
CACC ATG TGT CAG TGT ATA AAG ACA TAC TCC
(primer for the mutation Δ6)

(SEQ ID NO: 8)
CACC ATG TGT CAG TGT ATA AAG ACA TAC TCC AAA CCT

AGG CAC CCC AAA AGG ATA
(primer for the mutation Δ6 F17R F21R)
```

The reverse sequences are (5' to 3'):

```
TTA TGA ATT CCT AGC CCT CTT       (SEQ ID NO: 9)
(primer for the mutation E70R)

TTA TGA ATT CTT AGC CCT CTT       (SEQ ID NO: 10)
(primer for the mutation E70K)

TTA TGA CTT CTC AGC CCT CTT       (SEQ ID NO: 11)
(primer for the mutation N71K)

TTA TGA CTT CTT AGC CCT CTT       (SEQ ID NO: 12)
(primer for the mutation E70K
N71K)

TTA TGA CTT CCT AGC CCT CTT       (SEQ ID NO: 13)
(primer for the mutation E70R
N71K)

TTA TGA CCT CTT AGC CCT CTT       (SEQ ID NO: 14)
(primer for the mutation E70K
N71R)

TTA TGA CCT CCT AGC CCT CTT       (SEQ ID NO: 15)
(primer for the mutation E70R
N71R)
```

The PCR products were purified, cloned into the pCR®T7/NT-TOPO®TA (Invitrogen) vector and transformed into TOP10F competent *E. coli* (Invitrogen). As a next step a confirmation of the sequence was carried out by double-stranded DNA sequencing using a ABI PRISM CE1 Sequencer.

Example 2

Expression and Purification of the Recombinant Proteins

Once the sequences were confirmed, the constructs were transformed into calcium-competent BL21(DE3) *E. coli* for expression. Cells were grown under shaking in 1 l Lennox Broth (Sigma) containing 100 µg/ml Ampicillin at 37° C. until an $OD_{600}$ of about 0.8 was reached. Induction of protein expression was accomplished by addition of isopropyl-β-D-thiogalactopyranoside (IPTG) to a final concentration of 1 mM. Four hours later the cells were harvested by centrifugation at 6000 g for 20 minutes. The cell pellet was then resuspended in a buffer containing 20 mM TRIS/HCl, 50 mM NaCl, pH 8, sonicated at 100 watts for 5×20 s and finally centrifuged again for 20 min at 10,000 g. Since the main fraction of the recombinant IL-8 proteins was found in inclusion bodies, denaturing conditions were chosen for further purification. So the cell pellet was resuspended in a buffer of 6M Gua/HCl and 50 mM MES, pH 6.5. The suspension was then stirred at 4° C. for 4 hours, followed by a dialysis step against 50 mM MES, pH 6.5. The resulting suspension was then centrifuged and filtered to be loaded on a strong cation exchange column (SP Sepharose from Pharmacia Biotech). The elution was accomplished by a linear gradient from 0M-1M NaCl in a 50 mM MES buffer, pH 6.5 over 60 minutes. After lyophilisation of the fractions containing the desired protein, a second purification step was carried out by reversed-phase HPLC using a C18 column. In this case a non-linear gradient from 10%-90% Acetonitril was chosen to elute the desired protein. Refolding of the denatured protein was finally accomplished by the same cation exchange column under the same conditions as described above.

The protein was then checked for purity and identity by silver stain analysis in the first case and Western Blot analysis, using a specific monoclonal antibody against wtIL-8, in the second. Refolding of the proteins was also confirmed by Circular Dichroism (CD) measurements.

Example 3

Biophysical Characterisation of the Mutants 3.1 Circular Dicroism Measurements and Analysis In order to investigate secondary structure changes of the mutant protein in the presence and absence of heparan sulphate (HS), CD spectroscopy was carried out. Measurements were recorded on a Jasco J-710 spectropolarimeter over a range of 195-250 nm, and a cell of 0.1 cm path length was used. Spectra of the protein solutions with a concentration of 5 µM were recorded with a response time of 1 s, step resolution of 0.2 nm, speed of 50 nm/min, band width of 1 nm and a sensitivity of 20 mdeg. Three scans were averaged to yield smooth spectra. The protein spectra were then background-corrected relating to the CD-signal either of the buffer itself or buffer/HS. Secondary structure analysis of the protein in the presence and absence of HS was finally accomplished using the programme SELCON.

Since a great number of amino acids were changed in a number of novel combinations, it was tried to find out the dimension of the resulting secondary structure changes by circular dichroism methods.

Different structures were obtained depending on the mutations introduced. Except for one mutant expressed (Δ6 F17R F21R E70K N71R) which didn't show any structure, all mutants exhibited measurable α-helices, β-sheets and loops. Compared to IL-8 wt only one mutant (Δ6 E70R) showed nearly similar structure whereas the others differed mainly in their α-helix which ranged from 17.20 to 45.2% out of the total structure. Nevertheless, this fact suggests that the overall structure of IL-8 wt was maintained despite many changes within the proteins sequence. This could not have been previously predicted. Having already found that heparan sulphate oligosaccharides only, and not heparin, were able to affect IL-8 wt secondary structure, attention was focused on the effects induced by unfractionated heparan sulphate. All examined mutants showed structural changes upon HS binding which can be seen as evidence of complex formation.

To demonstrate the structural changes upon introduced mutations and heparan sulphate addition, some of the data obtained are summarised in the graphs above and below.

3.2 Fluorescence Measurements

For studying concentration and ligand dependent quaternary structure changes fluorescence spectroscopy was performed. Due to its high sensitivity, requiring only nanogram quantities of protein, fluorescence technique was the method of choice for carrying out the desired investigations. Measurements were undertaken using a Perkin-Elmer (Beaconsfield, England) LS50B fluorometer.

3.3 Fluorescence Anisotropy

By recording the concentration dependent fluorescence anisotropy of the chemokine resulting from the extrinsic chromophore bisANS it was aimed to find out the dimerisation constant of the mutants. Measurements were performed in PBS starting with high concentrations (up to 4 μM protein) followed by stepwise dilution. For each data point, the anisotropy signal (r) recorded at 507 nm was averaged over 60 sec.

IL-8 oligomerisation has been reported to relevantly influence the proteins GAG binding properties. Set at monomeric concentration, IL-8 bound size defined oligosaccharides 1000-fold tighter than at dimeric concentration. Therefore, the oligomerisation properties of IL-8 mutants were investigated by fluorescence anisotropy. Since the IL-8 intrinsic fluorophore (Trp57) was not sensitive enough for all of the mutants, the extrinsic fluorophore bis-ANS was used for these measurements.

Again, as already noticed for the secondary structure, the mutant Δ6 E70R showed high resemblance also in the oligomerisation constant ($k_{oligo}$=350 nM) to IL-8 wt ($k_{oligo}$=379 nM). The mutant with the highest $k_{oligo}$ ($k_{oligo}$=460 μM), which therefore dimerised worst, was Δ6 F17RF21R E70RN71K. Previous studies identified the β-sheets to be mainly involved in the dimerisation process, a fact, which correlates with the results for this mutants' secondary structure, which showed a very low share of β-sheet of only 11.4%. The mutant with the lowest $k_{oligo}$ ($k_{oligo}$=147 nM), was found to be Δ6 F17RF21R E70K, which again showed the highest share of β-sheet structure (29.8%) of all mutants investigated. Also the impact of heparan sulphate addition was observed. As for IL-8 wt, where heparan sulphate caused a shift of the oligomerisation constant to much higher levels ($k_{oligo}$=1.075 μM), this was also found for the IL-8 mutants investigated. Δ6 F17RF21R E70K shifted from 0.147 μM to 1.162 μM, and the mutant Δ6 E70R from 0.350 μM to 1.505 μM in the presence of heparan sulphate. Some of the results obtained are demonstrated in FIGS. 3 and 4, whereby FIG. 3 shows the dependence of the fluorescence anisotropy of IL-8 mutants in PBS on the chemokine concentration and FIG. 4 shows the dependence of the fluorescence anisotropy of Δ6 F17RF21R E70K in PBS on the chemokine concentration in the presence (ten fold excess) and absence of HS ((pc=10 xy excess) protein concentration).

3.4 Isothermal Fluorescence Titration (IFT) Experiments

Dissociation constants ($K_d$ values) are a measure for the binding affinity of a ligand to a protein and therefore concentration-dependent change in the fluorescence emission properties of the protein (fluorescence quenching) upon ligand binding was used for the determination of $K_d$. Since these mutants contain an intrinsic tryptophan chromophore which is located at or near the proposed GAG binding site and therefore should be sensitive to structural changes upon ligand binding, IFT experiments seemed to be suitable for this kind of investigation. Fluorescence intensity titration was performed in PBS using a protein concentration of 700 nM. The emission of the protein solution upon excitation at 282 nm was recorded over a range of 300-400 nm following the addition of an aliquot of the respective GAG ligand and an equilibration period of 60 sec.

Binding to unfractionated heparin and heparan sulphate was investigated. The mutants were set at dimeric concentration to assure sufficient sensitivity. A quenching of Trp57 fluorescence intensity upon GAG binding was registered within a range of 25-35%. Significant improvement of ligand binding was observed, especially for heparin binding. Δ6 F17RN71R E70K ($K_d$=14 nM) and Δ6 F17RF21R N71K ($K_d$=14.6 nM) showed 2600-fold better binding, and Δ6 E70K N71K ($K_d$=74 nM) 1760-fold better binding compared to IL-8 wt ($K_d$=37 μM). Good results were also obtained for heparan sulphate binding. For Δ6 F17RN71R E70K a $K_d$ of 107 nM was found, for Δ6 F17RF21R N71K the $K_d$ was 95 nM and the mutant AG E70K N71K showed a $K_d$ of 34 nM. As IL-8 wt binds with a $K_d$ of 4.2 μM, the $K_d$s found for the mutants represent an extraordinary improvement in binding, see FIG. 5.

3.5 Unfolding Experiments

In order to obtain information about the proteins stability and whether this stability would be changed upon GAG ligand binding, unfolding experiments were undertaken. As mentioned above fluorescence techniques are very sensitive for observing quaternary structure changes and therefore are also the method of choice to investigate thermal structural changes of the protein. Measurements were undertaken as described for the IFT in which not the ligand concentration was changed but the temperature. Protein structure was observed at a concentration of 0.7 μM from temperatures of 15-85° C. in the absence and the presence of a 10 fold excess of heparan sulphate or heparin.

The emission maximum of the proteins ranged from 340 nm to 357 nm, values which are typical for a solvent exposed tryptophan residue. Beginning with the unfolding experiments at 15° C., the emission maximum of the mutants varied between 340 nm-351 nm. Compared to IL-8 wt, whose emission maximum was observed at 340 nm, this means slightly higher values. Upon an increase in temperature, the intensity of emission maximum decreased, accompanied by a shift of the maximum to either a higher or lower wavelength. The emission maximum of Δ6 E70R and Δ6 E70K N71K shifted from 352.5 nm-357 nm and 343 nm-345 nm, which is typical for a further exposure of the Trp57 residue to the solvent trough temperature increase, but interestingly the mutants Δ6 F17RN71R E70K and Δ6 F17RF21R E70R N71K showed a blue shift, ranging from 350 nm-343 nm and, less pronounced, from 350 nm-348 nm (see FIG. 6). By slowly decreasing the temperature, the process of unfolding was partially reversible regarding both the wavelength shift and changes of intensity. Addition of a 5 fold excess of heparan sulphate led to an increase of stability of the proteins, probably through complex formation. This could be observed on the one hand by a shift of the melting point to higher temperature, and on the other hand by a significantly less pronounced shift of emission maximum upon temperature increase.

Example 4

Cell-Based Assay of the Receptor-"Negative" Function of the Dominant-Negative IL-8 Mutants In order to characterise the impaired receptor function of the IL-8 mutants with respect to neutrophil attraction, transfilter-based chemotaxis of neutrophils in response to IL-8 mutants was assayed in a microchemotaxis chamber equipped with a 5 µm PVP-free polycarbonate membrane.

Cell Preparation:

Briefly, a neutrophil fraction was prepared from freshly collected human blood. This was done by adding a 6% dextran solution to heparin-treated blood (1:2) which was then left for sedimentation for 45 min. The upper clear cell solution was collected and washed twice with HBSS w/o Ca and Mg. Cells were counted and finally diluted with HBSS at 2 Mio/ml cell suspension, taking into account that only 60% of the counted cells were neutrophils.

Chemotaxis Assay:

IL-8 mutants were diluted at concentrations of 10 µg/ml, 1 µg/ml and 0.1 µg/ml and put in triplicates in the lower compartment of the chamber (26 µl per well). The freshly prepared neutrophils were seeded in the upper chamber (50 µl per well) and incubated for 30 minutes at 37° C. in a 5% $CO_2$ humidified incubator. After incubation, the chamber was disassembled, the upper side of the filter was washed and wiped off and cells attached to the lower side were fixed with methanol and stained with Hemacolor solutions (Merck). Cells were then counted at 400× magnifications in 4 randomly selected microscopic fields per well. Finally, the mean of three independent experiments was plotted against the chemokine concentration. In FIG. 7, the chemotaxis index for various IL-8 mutants is shown. As expected, all mutants showed significantly decreased receptor binding activity.

Example 5

Generation of Recombinant RANTES Genes, Expression, Biophysical and Activity Characterisation of the Mutants The concept of dominant-negative "GAG-masking" chemokine mutants was also employed to RANTES, a chemokine involved in type IV hypersensitivity reactions like transplant rejection, atopic dermatitis as well as in other inflammatory disorders like arthritis, progressive glomerulonephritis and inflammatory lung disease.

The receptor binding capability was impaired by introducing into the wt protein an initiating methionine residue. Expression of the wt RANTES in *E. Coli* lead to the retention of this methionine residue, which renders wt RANTES to a potent inhibitor of monocyte migration, the so-called Met-RANTES. Different mutations enhancing the GAG binding affinity were introduced via PCR-based site-directed mutagenesis methods.

By these means 9 RANTES mutants have so far been cloned, expressed and purified, Met-RANTES A22K, Met-RANTES H23K, Met-RANTES T43K, Met-RANTES N46R, Met-RANTES N46K, Met-RANTES Q48K, Met-RANTES A22K/N46R, Met-RANTES V49R/E66S and Met-RANTES $^{15}$LSLA$^{18}$ V49R/E66S.

Isothermal fluorescence titration experiments were carried out to measure the relative affinity constants (Kd values) of the RANTES mutants for size defined heparin. As can be seen in the table all RANTES mutant proteins showed higher affinities for this heparin, with Met-RANTES A22K, Met-RANTES H23K, Met-RANTES T43K and Met-RANTES A22K/N46R showing the most promising results.

|  | Kd in nM |
|---|---|
| Wt Rantes | 456.2 ± 8.5 |
| Met-Rantes V49R/E66S | 345.5 ± 21.7 |
| Rantes 15LSLA18 V49R/66S | 297.3 ± 14.1 |
| Rantes N46R | 367.7 ± 11.7 |
| Rantes N46K | 257.4 ± 10.2 |
| Rantes H23K | 202.5 ± 12.8 |
| Rantes Q48K | 383.4 ± 39.6 |
| Rantes T43K | 139.2 ± 30.1 |
| Rantes A22K | 202.1 ± 9.8 |
| Rantes A22K/N46R | 164.0 ± 16.6 |

RANTES Chemotaxis Assay

RANTES mutant directed cell migration was investigated using the 48-well Boyden chamber system equipped with 5 µm PVP-coated polycarbonate membranes. RANTES and RANTES mutant dilutions in RPMI 1640 containing 20 mM HEPES pH 7.3 and 1 mg/ml BSA were placed in triplicates in the lower wells of the chamber. 50 µl of THP-1 cell suspensions (promonocytic cell line from the European collection of cell cultures) in the same medium at $2\times10^6$ cells/ml were placed in the upper wells. After a 2 h incubation period at 37° C. in 5% $CO_2$ the upper surface of the filter was washed in HBSS solution. The migrated cells were fixed in methanol and stained with Hemacolor solution (Merck). Five 400× magnifications per well were counted and the mean of three independently conducted experiments was plotted against the chemokine concentration in FIG. 8. The error bars represent the standard error of the mean of the three experiments. Again, as in the case of the IL-8 mutants, all RANTES mutants showed significantly reduced receptor binding activity.

Example 6

Proteins with GAG Binding Regions

By bioinformatical and by proteomical means GAG binding proteins were characterised together with their GAG binding regions. In the following tables 2 and 3 chemokines are shown with their GAG binding regions (table 2) and examples of other proteins are given also with their GAG binding regions (table 3).

TABLE 2

| Chemokines and their GAG binding domains |
|---|
| CXC-chemokines |

IL-8:
$^{18}$HPK$^{20}$, (R47) $^{60}$RVVEKFLKR$^{68}$
(residues 60-68 of SEQ ID NO: 16)
SAKELRCQCIKTYSKPFHPKFIKELRVIESGPHCANTEIIVKLSDGRELC
LDPKENWVQRVVEKFLKRAENS
(SEQ ID NO: 16)

TABLE 2-continued

Chemokines and their GAG binding domains

MGSA/GROα:
[19]HPK[21], [45]KNGR[48]
(residues 45-48 of SEQ ID NO: 17),
[60]KKIIEK[66]
(residues 60-66 of SEQ ID NO: 17)
ASVATELRCQCLQTLQGIHPKNIQSVNVKSPGPHCAQTEVIATLKNGRKA
CLNPASPIVKKIIEKMLNSDKSN
(SEQ ID NO: 17)

MIP-2α/GROβ:
[19]HLK[21], K45, [60]KKIIEKMLK[68]
(residues 60-68 of SEQ ID NO: 18)
APLATELRCQCLQTLQGIHLKNIQSVKVKSPGPHCAQTEVIATLKNGQKA
CLNPASPMVKKIIEKMLKNGKSN
(SEQ ID NO: 18)

NAP-2:
[15]HPK[18], [42]KDGR[45]
(residues 42-45 of SEQ ID NO: 19),
[57]KKIVQK[62]
(residues 57-62 of SEQ ID NO: 19)
AELRCLCIKTTSGIHPKNIQSLEVIGKGTHCNQVEVIATLKDGRKICLDP
DAPRIKKIVQKKLAGDESAD
(SEQ ID NO: 19)

PF-4:
[20]RPRH[23]
(residues 20-23 of SEQ ID NO: 20),
[46]KNGR[49]
(residues 46-49 of SEQ ID NO: 20),
[61]KKIIKK[66]
(residues 61-66 of SEQ ID NO: 20)
EAEEDGDLQCLCVKTTSQVRPRHITSLEVIKAGPHCPTAQLIATLKNGRK
ICLDLQAPLYKKIIKKLLES
(SEQ ID NO: 20)

SDF-1α:
K1, [24]KHLK[27]
(residues 24-27 of SEQ ID NO: 21),
[41]RLK[43]
KPVSLSYRCPCRFFESHVARANVKHLKILNTPNCALQIVARLKNNNRQVC
IDPKLKWIQEYLEKALN
(SEQ ID NO: 21)

CC-chemokines

RANTES:
([17]RPLPRAH[23] (residues 17-23 of SEQ ID NO: 22))
[44]RKNR[47] (residues 44-47 of SEQ ID NO: 22)
SPYSSDTTPCCFAYIARPLPRAHIKEYFYTSGKCSNPAVVFVTKRNRQVC
ANPEKKWVREYINSLEMS
(SEQ ID NO: 22)

MCP-2:
[18]RKIPIQR[24]
(residues 18-24 of SEQ ID NO: 23),
[46]KRGK[49]
(residues 46-49 of SEQ ID NO: 23)
QPDSVSIPITCCFNVINRKIPIQRLESYTRITNIQCPKEAVIFKTKRGKE
VCADPKERWVRDSMKHLDQIFQNLKP
(SEQ ID NO: 23)

MCP-3:
[22]KQR[24], [47]KLDK[50]
(residues 47-50 of SEQ ID NO: 24),
[66]KHLDKK[71]
(residues 66-71 of SEQ ID NO: 24)
QPVGINTSTTCCYRFINKKIPKQRLESYRRTTSSHCPREAVIFKTKLDKE
ICADPTQKWVQDFMKHLDKKTQTPKL
(SEQ ID NO: 24)

TABLE 2-continued

Chemokines and their GAG binding domains

MIP-1α:
R17, [44]KRSR[47]
(residues 44-47 of SEQ ID NO: 25)
SLAADTPTACCFSYTSRQIPQNFIADYFETSSQCSKPGVIFLTKRSRQVC
ADPSEEWVQKYVSDLELSA
(SEQ ID NO: 25)

MIP-1β:
R18, [45]KRSK[48]
(residues 45-48 of SEQ ID NO: 26)
APMGSDPPTACCFSYTARKLPRNFVVDYYETSSLCSQPAVVFQTKRSKQV
CADPSESWVQEYVYDLELN
(SEQ ID NO: 26)

MPIF-1:
R18, [45]KKGR[48]
(residues 45-48 of SEQ ID NO: 27)
MDRFHATSADCCISYTPRSIPCSLLESYFETNSECSKPGVIFLTKKGRRF
CANPSDKQVQVCMRMLKLDTRIKTRKN
(SEQ ID NO: 27)

MIP-5/HCC-2:
[40]KKGR[43]
(residues 40-43 of SEQ ID NO: 28)
HFAADCCTSYISQSIPCSLMKSYFETSSECSKPGVIFLTKKGRQVCAKPS
GPGVQDCMKKLKPYSI
(SEQ ID NO: 28)

TABLE 3

| | SEQ ID NO: | | |
|---|---|---|---|
| Peroxisome biogenesis factor 1 | 29 | 181 | TRRAKE 186 |
| | 30 | 367 | QKKIRS 372 |
| | 31 | 1263 | PKRRKN 1268 |
| | 32 | 181 | TRRAKE 186 |
| | 33 | 367 | QKKIRS 372 |
| | 34 | 1263 | PKRRKN 1268 |
| MLTK-beta | 35 | 415 | SKRRGKKV 422 |
| | 36 | 312 | ERRLKM 317 |
| | 37 | 416 | KRRGKK 421 |
| | 38 | 312 | ERRLKM 317 |
| | 39 | 416 | KRRGKK 421 |
| BHLH factor Hes4 | 40 | 43 | EKRRRARI 50 |
| | 41 | 43 | EKRRRA 48 |
| | 42 | 43 | EKRRRA 48 |
| Protocadherin 11 | 43 | 867 | MKKKKKKK 874 |
| | 44 | 867 | MKKKKKK 872 |
| | 45 | 867 | MKKKKK 872 |
| | 46 | 899 | MKKKKKKK 906 |
| | 47 | 899 | MKKKKK 904 |
| | 48 | 899 | MKKKKK 904 |
| catenin (cadherin-associated protein), delta 1 | 49 | 315 | RRRLRS 320 |
| | 50 | 404 | VRKLKG 409 |
| | 51 | 460 | LRKARD 465 |
| | 52 | 545 | RRKLRE 550 |
| | 53 | 621 | AKKGKG 626 |
| | 54 | 787 | AKKLRE 792 |
| | 55 | 315 | RRRLRS 320 |
| | 56 | 404 | VRKLKG 409 |
| | 57 | 460 | LRKARD 465 |
| | 58 | 545 | RRKLRE 550 |
| | 59 | 621 | AKKGKG 626 |
| | 60 | 787 | AKKLRE 792 |

TABLE 3-continued

| | SEQ ID NO: | | |
|---|---|---|---|
| Muscarinic acetylcholine receptor M5 | 61 | 221 | EKRTKD 226 |
| | 62 | 427 | TKRKRV 432 |
| | 63 | 514 | WKKKKV 519 |
| | 64 | 221 | EKRTKD 226 |
| | 65 | 427 | TKRKRV 432 |
| | 66 | 514 | WKKKKV 519 |
| Alpha-2A adrenergi receptor | 67 | 147 | PRRIKA 152 |
| | 68 | 224 | KRRTRV 229 |
| | 69 | 147 | FRRIKA 152 |
| | 70 | 224 | KRRTRV 229 |
| IL-S promoter REII-region-binding protein | 71 | 440 | TKKKTRRR 447 |
| | 72 | 569 | GKRRRRG 576 |
| | 73 | 38 | ARKGKR 43 |
| | 74 | 437 | GKKTKK 442 |
| | 75 | 444 | TRRRRA 449 |
| | 76 | 569 | GKRRRR 574 |
| | 77 | 38 | ARKGKR 43 |
| | 78 | 437 | GKKTKK 442 |
| | 79 | 444 | TRRRRA 449 |
| | 80 | 569 | GKRRRR 574 |
| Mitofusin 1 | 81 | 291 | ARKQKA 296 |
| | 82 | 395 | KKKIKE 400 |
| | 83 | 291 | ARKQKA 296 |
| | 84 | 395 | KKKIKE 400 |
| N-cym protein | 85 | 71 | VRRCKI 76 |
| | 86 | 71 | VRRCKI 76 |
| Smad ubiquitination regulatory factor 1 | 87 | 672 | ERRARL 677 |
| | 88 | 672 | ERRARL 677 |
| CUG-BP and ETR-3 like factor 5 | 89 | 468 | MKRLKV 473 |
| | 90 | 475 | LKRPKD 480 |
| | 91 | 468 | MKRLKV 473 |
| | 92 | 475 | LKRPKD 480 |
| Ewings sarcoma EWS-Fli1 | 93 | 347 | QRKSKP 352 |
| | 94 | 347 | QRKSKP 352 |
| NUF2R | 95 | 455 | LKRKMFKM 462 |
| | 96 | 331 | LKKLKT 336 |
| | 97 | 347 | VKKEKL 352 |
| | 98 | 331 | LKKLKT 336 |
| | 99 | 347 | VKKEKL 352 |
| Kruppel-like zinc finger protein GLIS2 | 100 | 22 | EKRERT 27 |
| | 101 | 22 | EKEERT 27 |
| FKSG32 | 102 | 15 | LKRVRE 20 |
| | 103 | 431 | VRRGRI 436 |
| | 104 | 15 | LKRVRE 20 |
| | 105 | 431 | VRRGRI 436 |
| BARH-LIKE 1 PROTEIN | 106 | 175 | LKKPRK 180 |
| | 107 | 228 | NRRTKW 233 |
| | 108 | 175 | LKKPRK 180 |
| | 109 | 228 | NRRTKW 233 |
| Nucleolar GTP-binding protein | 110 | 393 | SRKKRERD 400 |
| | 111 | 624 | GKRKAGKK 631 |
| | 112 | 48 | MRKVKF 53 |
| | 113 | 141 | IKRQKQ 146 |
| | 114 | 383 | ARRKRM 388 |
| | 115 | 393 | SRKKRE 398 |
| | 116 | 490 | KKKLKI 495 |
| | 117 | 543 | ARRSRS 548 |
| | 118 | 550 | TRKRKR 555 |
| | 119 | 586 | VKKAKT 591 |
| | 120 | 629 | GKKDRR 634 |
| | 121 | 48 | MRKVKF 53 |
| | 122 | 141 | IKRQKQ 146 |
| | 123 | 383 | ARRKRM 388 |
| | 124 | 393 | SRKKRE 398 |
| | 125 | 490 | KKKLKI 495 |
| | 126 | 543 | ARRSRS 548 |
| | 127 | 550 | TRKRKR 555 |
| | 128 | 586 | VKKAKT 591 |
| | 129 | 629 | GKKDRR 634 |
| EVG1 | 130 | 17 | RRRPKT 22 |
| | 131 | 138 | ERRKRA 143 |
| | 132 | 17 | RRRPKT 22 |
| | 133 | 138 | ERRKRA 143 |
| ASPL | 134 | 282 | PKKSKS 287 |
| | 135 | 282 | PKKSKS 287 |
| Zinc transporter 1 | 136 | 477 | EKKPRR 482 |
| | 137 | 477 | EKKPRR 482 |
| Uveal autoantigen | 138 | 603 | EKKGRK 608 |
| | 139 | 995 | ERKFKA 1000 |
| | 140 | 1023 | VKKNKQ 1028 |
| | 141 | 603 | EKKGRK 608 |
| | 142 | 995 | ERKFKA 1000 |
| | 143 | 1023 | VKKNKQ 1028 |
| RAB39 | 144 | 7 | VRRDRV 12 |
| | 145 | 7 | VRRDRV 12 |
| Down syndrome cell adhesion molecule | 146 | 320 | PRKVKS 325 |
| | 147 | 387 | VRKDKL 392 |
| | 148 | 320 | PRKVKS 325 |
| | 149 | 387 | VRKDKL 392 |
| Proteintyrosine phosphatase, non-receptor type 12 | 150 | 139 | GRKKCERY 146 |
| | 151 | 59 | VKKNRY 64 |
| | 152 | 59 | VKKNRY 64 |
| WD-repeat protein 11 | 153 | 752 | VRKIRF 757 |
| | 154 | 752 | VRKIRF 757 |
| Gastric cancer-related protein VRG107 | 155 | 20 | SRKRQTRR 27 |
| | 156 | 25 | TRRRRN 30 |
| | 157 | 25 | TRRRRN 30 |
| Early growth response protein 4 | 158 | 356 | ARRKGRRG 363 |
| | 159 | 452 | EKKRHSKV 459 |
| | 160 | 357 | RRKGRR 362 |
| | 161 | 357 | RRKGRR 362 |
| Vesicle transport-related protein | 162 | 309 | PKRKNKKS 316 |
| | 163 | 226 | DKKLRE 231 |
| | 164 | 310 | KRKNKK 315 |
| | 165 | 355 | VKRLKS 360 |
| | 166 | 226 | DKKLRE 231 |
| | 167 | 310 | KRKNKK 315 |
| | 168 | 355 | VKRLKS 360 |
| UPF3X | 169 | 140 | AKKKTKKR 147 |
| | 170 | 141 | KKKTKK 146 |
| | 171 | 217 | ERRRRE 222 |
| | 172 | 225 | RKRQRE 230 |
| | 173 | 233 | RRKWKE 238 |
| | 174 | 240 | EKRKRK 245 |
| | 175 | 296 | DKREKA 301 |
| | 176 | 373 | RRRQKE 378 |
| | 177 | 393 | MKKEKD 398 |
| | 178 | 426 | VKRDRI 431 |
| | 179 | 140 | AKKKTKKRD 148 |
| | 180 | 141 | KKKTKK 146 |
| | 181 | 217 | ERRRRE 222 |
| | 182 | 225 | RKRQRE 230 |
| | 183 | 233 | RRKWKE 238 |
| | 184 | 240 | EKRKRK 245 |
| | 185 | 296 | DKREKA 301 |
| | 186 | 373 | RRRQKE 378 |
| | 187 | 393 | MKKEKD 398 |
| | 188 | 426 | VKRDRI 431 |

TABLE 3-continued

| | SEQ ID NO: | | |
|---|---|---|---|
| CGI-201 protein, type IV | 189 | 49 ARRTRS | 54 |
| | 190 | 49 ARRTRS | 54 |
| RING finger protein 23 | 191 | 98 KRKIRD | 103 |
| | 192 | 98 KRKIRD | 103 |
| FKSG17 | 193 | 72 EKKARK | 77 |
| | 194 | 95 IRKSKN | 100 |
| | 195 | 72 EKKARK | 77 |
| | 196 | 95 IRKSKN | 100 |
| P83 | 197 | 681 ARKERE | 686 |
| | 198 | 681 ARKERE | 686 |
| Ovarian cancer-related protein 1 | 199 | 62 LKRDRF | 67 |
| | 200 | 62 LKRDRF | 67 |
| MHC class II transactivator CIITA | 201 | 407 HRRPRE | 412 |
| | 202 | 741 PRKKRP | 746 |
| | 203 | 783 DRKQKV | 788 |
| | 204 | 407 HRRPRE | 412 |
| | 205 | 741 PRKKRP | 746 |
| | 206 | 783 DRKQKV | 788 |
| Platelet glycoprotein VI-2 | 207 | 275 SRRKRLRN | 282 |
| | 208 | 275 SRRKRL | 280 |
| | 209 | 275 SRRKRL | 280 |
| Ubiquitin-like 5 protein | 210 | 11 GKKVRV | 16 |
| | 211 | 11 GKKVRV | 16 |
| Protein kinase D2 | 212 | 191 ARKRRL | 196 |
| | 213 | 191 ARKRRL | 196 |
| Homeobox protein GSH-2 | 214 | 202 GKRMRT | 207 |
| | 215 | 252 NRRVKH | 257 |
| | 216 | 202 GKRMRT | 207 |
| | 217 | 252 NRRVKH | 257 |
| ULBP3 protein | 218 | 166 ARRMKE | 171 |
| | 219 | 201 HRKKRL | 206 |
| | 220 | 166 ARRMKE | 171 |
| | 221 | 201 HRKKRL | 206 |
| Type II iodothyronine deiodinase | 222 | 87 SKKEKV | 92 |
| | 223 | 87 SKKEKV | 92 |
| | 224 | 299 SKRCKK | 304 |
| | 225 | 299 SKRCKK | 304 |
| Sperm antigen | 226 | 160 LKKYKE | 165 |
| | 227 | 478 IKRLKE | 483 |
| | 228 | 160 LKKYKEKRT | 168 |
| | 229 | 160 LKKYKE | 165 |
| | 230 | 478 IKRLKE | 483 |
| UDP-GalNAc: polypeptide N-acetylgalactosaminyl-transferase | 231 | 4 ARKIRT | 9 |
| | 232 | 44 DRRVRS | 49 |
| | 233 | 138 PRKCRQ | 143 |
| | 234 | 4 ARKIRT | 9 |
| | 235 | 44 DRRVRS | 49 |
| | 236 | 138 PRKCRQ | 143 |
| NCBE | 237 | 62 HRRHRN | 67 |
| | 238 | 73 RKRDRE | 78 |
| | 239 | 1012 SKKKKL | 1017 |
| | 240 | 62 HRRHRH | 67 |
| | 241 | 73 RKRDRE | 78 |
| | 242 | 1012 SKKKKL | 1017 |
| WD repeat protein | 243 | 372 LKKKEERL | 379 |
| | 244 | 384 EKKQRR | 389 |
| | 245 | 400 AKKMRP | 405 |
| | 246 | 384 EKKQRR | 389 |
| | 247 | 400 AKKMRP | 405 |
| Phosphodiesterase 11A | 248 | 27 MRKGKQ | 32 |
| | 249 | 27 MRKGKQ | 32 |
| probable cation-transporting ATPase 2 | 250 | 891 ERRRRPRD | 898 |
| | 251 | 306 SRKWRP | 311 |
| | 252 | 891 ERRRRP | 896 |
| | 253 | 306 SRKWRP | 311 |
| | 254 | 891 ERRRRP | 896 |
| HMG-box transcription factor TCF-3 | 255 | 420 GKKKKRKR | 427 |
| | 256 | 399 ARKERQ | 404 |
| | 257 | 420 GKKKKR | 425 |
| | 258 | 420 GKKKKRKRE | 428 |
| | 259 | 399 ARKERQ | 404 |
| | 260 | 420 GKKKKR | 425 |
| HVPS11 | 261 | 793 VRRYRE | 798 |
| | 262 | 793 VRRYRE | 798 |
| PIST | 263 | 165 NKKEKM | 170 |
| | 264 | 165 NKKEKM | 170 |
| FYN-binding protein | 265 | 473 KKREKE | 478 |
| | 266 | 501 KKKFKL | 506 |
| | 267 | 682 LKKLKK | 687 |
| | 268 | 696 RKKFKY | 701 |
| | 269 | 473 KKREKE | 478 |
| | 270 | 501 KKKFKL | 506 |
| | 271 | 682 LKKLKK | 687 |
| | 272 | 696 RKKFKY | 701 |
| C1orf25 | 273 | 620 GKKQKT | 625 |
| | 274 | 620 GKKQKT | 625 |
| C1orf14 | 275 | 441 LRRKGKR | 448 |
| | 276 | 70 LRRWRR | 75 |
| | 277 | 441 LRRRKG | 446 |
| | 278 | 70 LRRWRR | 75 |
| | 279 | 441 LRRRKG | 446 |
| T-box transcription factor TBX3 | 280 | 144 DKKAKY | 149 |
| | 281 | 309 GRREKR | 314 |
| | 282 | 144 DKKAKY | 149 |
| | 283 | 309 GRREKR | 314 |
| Mitochondrial 39S ribosomal protein L47 | 284 | 121 AKRQRL | 126 |
| | 285 | 216 EKRARI | 221 |
| | 286 | 230 RKKAKI | 235 |
| | 287 | 121 AKRQRL | 126 |
| | 288 | 216 EKRARI | 221 |
| | 289 | 230 RKKAKI | 235 |
| CGI-203 | 290 | 33 VRRIRD | 38 |
| | 291 | 33 VRRIRD | 38 |
| Jagged1 | 292 | 1093 LRKRRK | 1098 |
| | 293 | 1093 LRKRRK | 1098 |
| Secretory carrier-associated membrane protein 1 | 294 | 102 DRRERE | 107 |
| | 295 | 102 DRRERE | 107 |
| Vitamin D receptor-interacting protein complex component DRIP205 | 296 | 673 KKKKSSRL | 680 |
| | 297 | 672 TKKKKS | 677 |
| | 298 | 954 QKRVKE | 959 |
| | 299 | 978 GKRSRT | 983 |
| | 300 | 995 PKRKKA | 1000 |
| | 301 | 1338 GKREKS | 1343 |
| | 302 | 1482 HKKHKK | 1487 |
| | 303 | 1489 KKKVKD | 1494 |
| | 304 | 672 TKKKKS | 677 |
| | 305 | 954 QKRVKE | 959 |
| | 306 | 978 GKRSRT | 983 |
| | 307 | 999 PKRKKA | 1000 |
| | 308 | 1338 GKREKS | 1343 |
| | 309 | 1482 HKKHKK | 1487 |
| | 310 | 1489 KKKVKD | 1494 |

TABLE 3-continued

| | SEQ ID NO: | | |
|---|---|---|---|
| Secretory carrier-associated membrane protein 2 | 311 | 100 | ERKERE 105 |
| | 312 | 100 | ERKERE 105 |
| Nogo receptor | 313 | 420 | SRKNRT 425 |
| | 314 | 420 | SRKNRT 425 |
| FLAMINGO 1 | 315 | 169 | GRRKRN 174 |
| | 316 | 2231 | ARRQRR 2236 |
| | 317 | 169 | GRRKRN 174 |
| | 318 | 2231 | ARRQRR 2236 |
| CC-chemokine receptor | 319 | 58 | CKRLKS 63 |
| | 320 | 58 | CKRLKS 63 |
| Prolactin regulatory element-binding protien | 321 | 271 | HKRLRQ 276 |
| | 322 | 271 | HKRLRQ 276 |
| Kappa B and V(D)J recombination signal sequences binding protien | 323 | 17 | PRKRLTKG 24 |
| | 324 | 713 | RKRRKEKS 720 |
| | 325 | 903 | PKKKRLRL 910 |
| | 326 | 180 | HKKERK 185 |
| | 327 | 629 | TKKTKK 634 |
| | 328 | 712 | LRKRRK 717 |
| | 329 | 903 | PKKKRL 908 |
| | 330 | 1447 | QKRVKE 1452 |
| | 331 | 1680 | SRKPRM 1685 |
| | 332 | 180 | HKKERK 185 |
| | 333 | 629 | TKKTKK 634 |
| | 334 | 712 | LRKRRK 717 |
| | 335 | 903 | PKKKRL 908 |
| | 336 | 1447 | QKRVKE 1452 |
| | 337 | 1680 | SRKPRM 1685 |
| Breast cancer metastasis-suppressor 1 | 338 | 200 | SKRKKA 205 |
| | 339 | 229 | IKKARA 234 |
| | 340 | 200 | SKRKKA 205 |
| | 341 | 229 | IKKARA 234 |
| Forkhead box protein P3 | 342 | 414 | RKKRSQRP 421 |
| | 343 | 413 | FRKKRS 418 |
| | 344 | 413 | FRKKRS 418 |
| FAS BINDING PROTEIN | 345 | 228 | LKRKLIRL 235 |
| | 346 | 391 | RKKRRARL 398 |
| | 347 | 358 | ARRLRE 363 |
| | 348 | 390 | ERKKRR 395 |
| | 349 | 629 | CKKSRK 634 |
| | 350 | 358 | ARRLRE 363 |
| | 351 | 390 | ERKKRR 395 |
| | 352 | 629 | CKKSRK 634 |
| Ubiquitin carboxyl-terminal hydrolase 12 | 353 | 28 | HKRMKV 233 |
| | 354 | 244 | LKRFKY 249 |
| | 355 | 228 | HKRMKV 233 |
| | 356 | 244 | LKRFKY 249 |
| K1AA0472 protein | 357 | 110 | HRKPKL 115 |
| | 358 | 110 | HRKPKL 115 |
| PNAS-101 | 359 | 68 | LKRSRP 73 |
| | 360 | 106 | PRKSRR 111 |
| | 361 | 68 | LKRSRP 73 |
| | 362 | 106 | PRKSRR 111 |
| PNAS-26 | 363 | 118 | DRRTRL 123 |
| | 364 | 118 | DRRTRL 123 |
| Myelin transcription factor 2 | 365 | 176 | GRRKSERQ 183 |
| Sodium/potassium-transporting ATPase gamma chain | 366 | 47 | SRRFRC 52 |
| | 367 | 55 | NKKRRQ 60 |
| | 368 | 47 | SRRFRC 52 |
| | 369 | 55 | NKKRRQ 60 |
| Mdm4 protein | 370 | 441 | EKRPRD 446 |
| | 371 | 464 | ARRLKK 469 |
| | 372 | 441 | EKRPRD 446 |
| | 373 | 464 | ARRLKK 469 |
| G antigen family D 2 protein | 374 | 87 | QKKIRI 92 |
| | 375 | 87 | QKKIRI 92 |
| NipSnap2 protein | 376 | 153 | FRKARS 158 |
| | 377 | 153 | FRKARS 158 |
| Stannin | 378 | 73 | ERKAKL 78 |
| | 379 | 73 | ERKAKL 78 |
| Sodium bicarbonate cotransporter | 380 | 973 | EKKKKKK 980 |
| | 381 | 165 | LRKHRH 170 |
| | 382 | 666 | LKKFKT 671 |
| | 383 | 966 | DKKKKE 971 |
| | 384 | 973 | EKKKKK 978 |
| | 385 | 165 | LRKHRH 170 |
| | 386 | 666 | LKKFKT 671 |
| | 387 | 966 | DKKKKE 971 |
| | 388 | 973 | EKKKKK 978 |
| Myosin X | 389 | 683 | YKRYKV 688 |
| | 390 | 828 | EKKKRE 833 |
| | 391 | 1653 | LKRIRE 1658 |
| | 392 | 1676 | LKKTKC 1681 |
| | 393 | 683 | YKRYKV 688 |
| | 394 | 828 | EKKKRE 833 |
| | 395 | 1653 | LKRIRE 1658 |
| | 396 | 1676 | LKKTKC 1681 |
| PNAS-20 | 397 | 21 | RKRKSVRG 28 |
| | 398 | 20 | ERKRKS 25 |
| | 399 | 20 | ERKRKS 25 |
| Pellino | 400 | 36 | RRKSRF 41 |
| | 401 | 44 | FKRPKA 49 |
| | 402 | 36 | RRKSRF 41 |
| | 403 | 44 | FKRPKA 49 |
| Hyaluronan mediated motility receptor | 404 | 66 | ARKVKS 71 |
| | 405 | 66 | ARKVKS 71 |
| Short transient receptor potential channel 7 | 406 | 753 | FKKTRY 758 |
| | 407 | 753 | FKKTRY 758 |
| Liprin-alpha2 | 408 | 825 | PKKKGIKS 832 |
| | 409 | 575 | IRRPRR 580 |
| | 410 | 748 | LRKHRR 753 |
| | 411 | 839 | GKKEKA 844 |
| | 412 | 875 | DRRLKK 880 |
| | 413 | 575 | IRRPRR 580 |
| | 414 | 748 | LRKHRR 753 |
| | 415 | 839 | GKKEKA 844 |
| | 416 | 875 | DRRLKK 880 |
| Transcription intermediary factor 1-alpha | 417 | 904 | DKRKCERL 911 |
| | 418 | 1035 | PRKKRLKS 1042 |
| | 419 | 321 | NKKGKA 326 |
| | 420 | 1035 | PRKKRL 1040 |
| | 421 | 321 | NKKGKA 326 |
| | 422 | 1035 | PRKKRL 1040 |
| CARTILAGE INTERMEDIATE LAYER PROTEIN | 423 | 719 | QRRNKR 724 |
| | 424 | 719 | QRRNKR 724 |
| UBX domain-containing protien 1 | 425 | 194 | YRKIKL 199 |
| | 426 | 194 | YRKIKL 199 |
| Arachidonate 12-lipoxygenase, 12R type | 427 | 166 | VRRHRN 171 |
| | 428 | 233 | WKRLKD 238 |
| | 429 | 166 | VRRHRN 171 |
| | 430 | 233 | WKRLKD 238 |

TABLE 3-continued

| | SEQ ID NO: | | |
|---|---|---|---|
| Hematopoietic PBX-interacting protein | 431 | 159 | LRRRRGRE 166 |
| | 432 | 698 | LKKRSGKK 705 |
| | 433 | 159 | LRRRRG 164 |
| | 434 | 703 | GKKDKH 708 |
| | 435 | 159 | LRRRRG 164 |
| | 436 | 703 | GKKDKH 708 |
| NAG18 | 437 | 28 | LKKKKK 33 |
| | 438 | 28 | LKKKKK 33 |
| POU 5 domain protein | 439 | 222 | ARKRKR 227 |
| | 440 | 222 | ARKRKR 227 |
| NRCAM PROTEIN | 441 | 2 | PKKKRL 7 |
| | 442 | 887 | SKRNRR 892 |
| | 443 | 1185 | IRRNKG 1190 |
| | 444 | 1273 | GKKEKE 1278 |
| | 445 | 2 | PKKKRL 7 |
| | 446 | 887 | SKRNRR 892 |
| | 447 | 1185 | IRRNKG 1190 |
| | 448 | 1273 | GKKEKE 1278 |
| protocadherin gamma cluster | 449 | 11 | TRRSRA 16 |
| | 450 | 11 | TRRSRA 16 |
| SKD1 protein | 451 | 288 | IRRRFEKR 295 |
| | 452 | 251 | ARRIKT 256 |
| | 453 | 362 | FKKVRG 367 |
| | 454 | 251 | ARRIKT 256 |
| | 455 | 362 | FKKVRG 367 |
| ANTI-DEATH PROTEIN | 456 | 58 | HRKRSRRV 65 |
| | 457 | 59 | RKRSRR 64 |
| | 458 | 59 | RKRSRR 64 |
| Centrin 3 | 459 | 14 | TKRKKRRE 21 |
| | 460 | 14 | TKRKKR 19 |
| | 461 | 14 | TKRKKR 19 |
| Ectonucleoside triphosphate diphosphohydrolase 3 | 462 | 512 | TRRKRH 517 |
| | 463 | 512 | TRRKRH 517 |
| Homeobox protein prophet of PIT-1 | 464 | 12 | PKKGRV 17 |
| | 465 | 69 | RRRHRT 74 |
| | 466 | 119 | NRRAKQ 124 |
| | 467 | 12 | PKKGRV 17 |
| | 468 | 69 | RRRHRT 74 |
| | 469 | 119 | NRRAKQ 124 |
| PROSTAGLANDIN EP3 RCEPTOR | 470 | 77 | YRRRESKR 84 |
| | 471 | 389 | MRKRRLRE 396 |
| | 472 | 82 | SKRKKS 87 |
| | 473 | 389 | MRKRRL 394 |
| | 474 | 82 | SKRKKS 87 |
| | 475 | 389 | MRKRRL 394 |
| Pituitary homeobox 3 | 476 | 58 | LKKKQRRQ 65 |
| | 477 | 59 | KKKQRR 64 |
| | 478 | 112 | NRRAXW 117 |
| | 479 | 118 | RKRERS 123 |
| | 480 | 59 | KKKQRR 64 |
| | 481 | 112 | NRRAKW 117 |
| | 482 | 118 | RKRERS 123 |
| HPRL-3 | 483 | 136 | KRRGRI 141 |
| | 484 | 136 | KRRGRI 141 |
| Advillin | 485 | 812 | MKKEKG 817 |
| | 486 | 812 | MKKEKG 817 |
| Nuclear LIM interactor-interacting factor 1 | 487 | 32 | GRRARP 37 |
| | 488 | 109 | LKKQRS 114 |
| | 489 | 32 | GRRARP 37 |
| | 490 | 109 | LKKQRS 114 |

TABLE 3-continued

| | SEQ ID NO: | | |
|---|---|---|---|
| Core histone macro-H2A.1 | 491 | 5 | GKKKSTKT 12 |
| | 492 | 114 | AKKRGSKG 121 |
| | 493 | 70 | NKKGRV 75 |
| | 494 | 132 | ANKAKS 137 |
| | 495 | 154 | ARKSKK 159 |
| | 496 | 302 | DKKLKS 307 |
| | 497 | 70 | NKKGRV 75 |
| | 498 | 132 | AKKAKS 137 |
| | 499 | 154 | ARKSKK 159 |
| | 500 | 302 | DKKLKS 307 |
| Villin-like protein | 501 | 180 | KRRRNQKL 187 |
| | 502 | 179 | EKRRRN 184 |
| | 503 | 179 | EKRRRN 184 |
| BETA-FILAMIN | 504 | 254 | PKKARA 259 |
| | 505 | 2002 | ARRAKV 2007 |
| | 506 | 254 | FKKARA 259 |
| | 507 | 2002 | ARRAKV 2007 |
| Tripartite motif protein TRIM31 alpha | 508 | 290 | LKKFKD 295 |
| | 509 | 290 | LKKFKD 295 |
| Nuclear receptor co-repressor 1 | 510 | 106 | SKRPRL 111 |
| | 511 | 299 | ARKQRE 304 |
| | 512 | 330 | RRKAKE 335 |
| | 513 | 349 | IRKQRE 354 |
| | 514 | 412 | QRRVKF 417 |
| | 515 | 497 | KRRGRN 502 |
| | 516 | 580 | RRKGRI 585 |
| | 517 | 687 | SRKPRE 692 |
| | 518 | 2332 | SRKSKS 2337 |
| | 519 | 106 | SKRPRL 111 |
| | 520 | 299 | ARKQRE 304 |
| | 521 | 330 | RRKAKE 335 |
| | 522 | 349 | IRKQRE 354 |
| | 523 | 412 | QRRVKF 417 |
| | 524 | 497 | KRRGRN 502 |
| | 525 | 580 | RRKGRI 585 |
| | 526 | 687 | SRKPRE 692 |
| | 527 | 2332 | SRKSKS 2337 |
| BRAIN EXPRESSED RING FINGER PROTEIN | 528 | 432 | KRRVKS 437 |
| | 529 | 432 | KRRVKS 437 |
| PB39 | 530 | 231 | TKKIKL 236 |
| | 531 | 231 | TKKIKL 236 |
| Sperm acrosomal protein | 532 | 48 | FRKRMEKE 55 |
| | 533 | 24 | RRKARE 29 |
| | 534 | 135 | KRKLKE 140 |
| | 535 | 213 | KKRLRQ 218 |
| | 536 | 24 | RRKARE 29 |
| | 537 | 135 | KRKLKE 140 |
| | 538 | 213 | KKRLRQ 218 |
| VESICLE TRAFFICKING PROTEIN SEC22B | 539 | 177 | SKKYRQ 182 |
| | 540 | 177 | SKKYRQ 182 |
| Nucleolar transcription factor 1 | 541 | 79 | VRKFRT 84 |
| | 542 | 102 | GKLLKK 107 |
| | 543 | 125 | EKRAKY 130 |
| | 544 | 147 | SKKYKE 152 |
| | 545 | 156 | KKKNKY 161 |
| | 546 | 240 | KKRLKW 245 |
| | 547 | 451 | KKKAKY 456 |
| | 548 | 523 | EKKEKL 528 |
| | 549 | 558 | SKKMKF 563 |
| | 550 | 79 | VRKFRT 84 |
| | 551 | 102 | GKLLKK 107 |
| | 552 | 125 | EKRAKY 130 |
| | 553 | 147 | SKKYKE 152 |
| | 554 | 156 | KKKMKY 161 |
| | 555 | 240 | KKRLKW 245 |

TABLE 3-continued

| | SEQ ID NO: | | |
|---|---|---|---|
| | 556 | 451 | KKKAKY 456 |
| | 557 | 523 | EKKEKL 528 |
| | 558 | 558 | SKKMKF 563 |
| Plexin-B3 | 559 | 248 | FRRRGARA 255 |
| Junctophilin type 3 | 560 | 626 | QKRRYSKG 633 |
| Plaucible mixed-lineage kinase protein | 561 | 773 | YRKKPHRP 780 |
| | 562 | 312 | ERRLKM 317 |
| | 563 | 312 | ERRLKM 317 |
| fatty acid binding protein 4, adipocyte | 564 | 78 | DRKVKS 83 |
| | 565 | 105 | IKRKRE 110 |
| | 566 | 78 | DRKVKS 83 |
| | 567 | 105 | IKRKRE 110 |
| exostoses (multiple) 1 | 568 | 78 | SKKGRK 83 |
| | 569 | 78 | SKKGRK 83 |
| DHHC-domain-containing cysteine-rich protein | 570 | 64 | HRRPRG 69 |
| | 571 | 64 | HRRPRG 69 |
| Myb proto-oncogene protein | 572 | 2 | ARRPRH 7 |
| | 573 | 292 | EKRIKE 297 |
| | 574 | 523 | LKKIKQ 528 |
| | 575 | 2 | ARRPRH 7 |
| | 576 | 292 | EKRIKE 297 |
| | 577 | 523 | LKKIKQ 528 |
| Longchain-fatty-acid--COA ligase 2 | 578 | 259 | RRKPKP 264 |
| | 579 | 259 | RRKPKP 264 |
| syntaxin1B2 | 580 | 260 | ARRKKI 265 |
| | 581 | 260 | ARRKKI 265 |
| Dachshund 2 | 582 | 162 | ARRKRQ 167 |
| | 583 | 516 | QKRLKK 521 |
| | 584 | 522 | EKKTKR 527 |
| | 585 | 162 | APRKRQ 167 |
| | 586 | 516 | QKRLKK 521 |
| | 587 | 522 | EKKTKR 527 |
| DEAD/DEXH helicase DDX31 | 588 | 344 | EKRKSEKA 351 |
| | 589 | 760 | TRKKRK 765 |
| | 590 | 760 | TRKKRK 765 |
| Androgen receptor | 591 | 628 | ARKLKK 633 |
| | 592 | 628 | ARKLKK 633 |
| Retinoic acid receptor alpha | 593 | 364 | RKRRPSRP 371 |
| | 594 | 163 | NKKKKE 168 |
| | 595 | 363 | VKRRRP 368 |
| | 596 | 163 | NKKKKE 168 |
| | 597 | 363 | VKRRRP 368 |
| Kinesin heavy chain | 598 | 340 | WKKKYEKE 347 |
| | 599 | 605 | VKRCKQ 610 |
| | 600 | 864 | EKRLRA 869 |
| | 601 | 605 | VKRCKQ 610 |
| | 602 | 864 | EKRLRA 869 |
| DIUBIQUITIN | 603 | 30 | VKKIKE 35 |
| | 604 | 30 | VKKIKE 35 |
| BING1 PROTEIN | 605 | 519 | NKKFKM 524 |
| | 606 | 564 | ERRHRL 569 |
| | 607 | 519 | NKKFKM 524 |
| | 608 | 564 | ERRHRL 569 |
| Focal adhesion kinase 1 | 609 | 664 | SRRPRF 669 |
| | 610 | 664 | SRRPRF 669 |
| EBN2 PROTEIN | 611 | 20 | TKRKKPRR 27 |
| | 612 | 13 | PKKDKL 18 |
| | 613 | 20 | TKRKKP 25 |
| | 614 | 47 | NKKNRE 52 |
| | 615 | 64 | LKKSRI 69 |

TABLE 3-continued

| | SEQ ID NO: | | |
|---|---|---|---|
| | 616 | 76 | PKKPRE 81 |
| | 617 | 493 | SRKQRQ 498 |
| | 618 | 566 | VKRKRK 571 |
| | 619 | 13 | PKKDKL 18 |
| | 620 | 20 | TKRKKP 25 |
| | 621 | 47 | NKKNRE 52 |
| | 622 | 64 | LKKSRI 69 |
| | 623 | 76 | PKKPRE 81 |
| | 624 | 493 | SRKQRQ 498 |
| | 625 | 566 | VKRKRK 571 |
| CO16 PROTEIN | 626 | 33 | ARRLRR 38 |
| | 627 | 115 | PRRCKW 120 |
| | 628 | 33 | ARRLRR 38 |
| | 629 | 115 | PRRCKW 120 |
| KYNURENINE 3-MONOOXYGENASE | 630 | 178 | MKKPRF 183 |
| | 631 | 178 | MKKPRF 183 |
| MLN 51 protein | 632 | 4 | RRRQRA 9 |
| | 633 | 255 | PRRIRK 260 |
| | 634 | 407 | ARRTRT 412 |
| | 635 | 4 | RRRQRA 9 |
| | 636 | 255 | PRRIRK 260 |
| | 637 | 407 | ARRTRT 412 |
| MHC class II antigen | 638 | 99 | QKRGRV 104 |
| MHC class II antigen | 639 | 99 | QKRGRV 104 |
| Transforming acidic colied-coli-containing protein 1 | 640 | 225 | SRRSKL 230 |
| | 641 | 455 | PKKAKS 460 |
| | 642 | 225 | SRRSKL 230 |
| | 643 | 455 | PKKAKS 460 |
| Neuro-endocrine specific protein VGF | 644 | 479 | EKRNRK 484 |
| | 645 | 479 | EKRNRK 484 |
| Organic cation transporter | 646 | 230 | GRRYRR 235 |
| | 647 | 535 | PRKNKE 540 |
| | 648 | 230 | GRRYRR 235 |
| | 649 | 535 | PRKNKE 540 |
| DNA polymerase theta | 650 | 215 | KRRKHLKR 222 |
| | 651 | 214 | WKRRH 219 |
| | 652 | 220 | LKRSRD 225 |
| | 653 | 1340 | GRKLRIA 1345 |
| | 654 | 1689 | SRKRKL 1694 |
| | 655 | 214 | WKRRH 219 |
| | 656 | 220 | LKRSRD 225 |
| | 657 | 1340 | GRKLRL 1345 |
| | 658 | 1689 | SRKRKL 1694 |
| CDC45-related protein | 659 | 169 | MRRRQRRE 176 |
| | 660 | 155 | EKRTRL 160 |
| | 661 | 170 | RRRQRR 175 |
| | 662 | 483 | NRRCKL 488 |
| | 663 | 155 | EKRTRL 160 |
| | 664 | 170 | RRRQRR 175 |
| | 665 | 483 | NRRCKL 488 |
| Chloride intracellular channel protein 2 | 666 | 197 | AKKYRD 202 |
| | 667 | 197 | AKKYRD 202 |
| Methyl-CpG binding protein | 668 | 85 | KRKKPSRP 92 |
| | 669 | 83 | SKRRKK 88 |
| | 670 | 318 | QKRQKC 323 |
| | 671 | 354 | YRRRKR 359 |
| | 672 | 83 | SKKRKK 88 |
| | 673 | 318 | QKRQKC 323 |
| | 674 | 354 | YRRRKR 359 |
| Protein kinase C, eta type | 675 | 155 | RKRQRA 160 |
| | 676 | 155 | RKRQRA 160 |

TABLE 3-continued

| | SEQ ID NO: | | |
|---|---|---|---|
| Heterogeneous nuclear ribonucleoprotein H | 677 | 71 | LKKDRE 76 |
| | 678 | 169 | LKKHKE 174 |
| | 679 | 71 | LKKDRE 76 |
| | 680 | 169 | LKKHKE 174 |
| ORF2 | 681 | 11 | SRRTRW 16 |
| | 682 | 155 | ERRRKF 160 |
| | 683 | 185 | LRRCRA 190 |
| | 684 | 530 | SRSRS 535 |
| | 685 | 537 | GRRRKS 542 |
| | 686 | 742 | ERRAKQ 747 |
| | 687 | 11 | SRRTRW 16 |
| | 688 | 155 | ERRRKF 160 |
| | 689 | 185 | LRRCRA 190 |
| | 690 | 530 | SRSRS 535 |
| | 691 | 537 | GRRRKS 542 |
| | 692 | 742 | ERRAKQ 747 |
| F-box only protein 24 | 693 | 9 | LRRRVKR 16 |
| | 694 | 9 | LRRRV 14 |
| | 695 | 29 | EKRGKG 34 |
| | 696 | 9 | LRRRV 14 |
| | 697 | 29 | EKRGKG 34 |
| Leucin rich neuronal protein | 698 | 51 | NRRLKH 56 |
| | 699 | 51 | NRRLKH 56 |
| RER1 protein | 700 | 181 | KRRYG 186 |
| | 701 | 181 | KRRYG 186 |
| Nephrocystin | 702 | 3 | ARRQRD 8 |
| | 703 | 430 | PKKPKT 435 |
| | 704 | 557 | NRRSRN 562 |
| | 705 | 641 | EKRDKE 646 |
| | 706 | 3 | ARRQRD 8 |
| | 707 | 430 | PKKPKT 435 |
| | 708 | 557 | NRRSRN 562 |
| | 709 | 641 | EKRDKE 646 |
| Adenylate kinase isoenzyme 2, mitochondrial | 710 | 60 | GKKLKA 65 |
| | 711 | 116 | KRKEKL 121 |
| | 712 | 60 | GKKLKA 65 |
| | 713 | 116 | KRKEKL 121 |
| Chlordecone reductase | 714 | 245 | AKKHKR 250 |
| | 715 | 245 | AKKHKR 250 |
| Metaxin 2 | 716 | 166 | KRKNKA 171 |
| | 717 | 166 | KRKMKA 171 |
| Paired mesoderm homebox protein 1 | 718 | 89 | KKKRKQRR 96 |
| | 719 | 88 | EKKKRK 93 |
| | 720 | 94 | QRRNRT 99 |
| | 721 | 144 | NRRAKF 149 |
| | 722 | 88 | EKKKRK 93 |
| | 723 | 94 | QRRNRT 99 |
| | 724 | 144 | NRRAKF 149 |
| Ring finger protein | 725 | 174 | LKRKWZLRC 181 |
| | 726 | 8 | TRKIKL 13 |
| | 727 | 95 | MRKQRE 100 |
| | 728 | 8 | TRKIKL 13 |
| | 729 | 95 | MRKQRE 100 |
| Ataxin 7 | 730 | 55 | PRRTRP 60 |
| | 731 | 377 | GRRKRF 382 |
| | 732 | 704 | GKKRKN 709 |
| | 733 | 834 | GKKRKC 839 |
| | 734 | 55 | PRRTRP 60 |
| | 735 | 377 | GRRKRF 382 |
| | 736 | 704 | GKKRKN 709 |
| | 737 | 834 | GKKRKC 839 |
| Growth-arrest-specific protein 1 | 738 | 169 | ARRRCDRD 176 |
| SKAP55 protein | 739 | 115 | EKKSKD 120 |
| | 740 | 115 | EKKSKD 120 |
| Serine palmitoyl-transferase 1 | 741 | 232 | PRKARV 237 |
| | 742 | 232 | PRKARV 237 |
| Serine palmitoyl-transferase 2 | 743 | 334 | KKKYKA 339 |
| | 744 | 450 | RRRLKE 455 |
| | 745 | 334 | KKKYKA 339 |
| | 746 | 450 | RRRLKE 455 |
| Synaptopodin | 747 | 405 | KRRQRD 410 |
| | 748 | 405 | KRRQRD 410 |
| Alpha-tectorin | 749 | 1446 | TRRCRC 1451 |
| | 750 | 2080 | IRRKRL 2085 |
| | 751 | 1446 | TRRCRC 1451 |
| | 752 | 2080 | IRRKRL 2085 |
| LONG FORM TRANSCRIPTION FACTOR C-MAF | 753 | 291 | QKRRTLKN 298 |
| Usher syndrome type IIa protein | 754 | 1285 | MRRLRS 1290 |
| | 755 | 1285 | MRRLRS 1290 |
| MSin3A associated polypeptied p30 | 756 | 95 | QKKVKI 100 |
| | 757 | 124 | NRRKRK 129 |
| | 758 | 158 | LRRYKR 163 |
| | 759 | 95 | QKKVKI 100 |
| | 760 | 124 | NRRKRK 129 |
| | 761 | 158 | LRRYKR 163 |
| Ig delta chain C region | 762 | 142 | KKKEKE 147 |
| | 763 | 142 | KKKEKE 147 |
| THYROID HORMONE RECEPTOR-ASSOCIATED PROTEIN COMPLEX COMPONENT TRAP100 | 764 | 383 | AKRKADRE 390 |
| | 765 | 833 | KKRHRE 838 |
| | 766 | 833 | KKRHRE 838 |
| P60 katanin | 767 | 369 | LRRRLEKR 376 |
| | 768 | 326 | SRRVKA 331 |
| | 769 | 326 | SRRVKA 331 |
| Transcription factor jun-D | 770 | 286 | RKRKLERI 293 |
| | 771 | 273 | RKRLRN 278 |
| | 772 | 285 | CRKKL 290 |
| | 773 | 273 | RKRLRN 278 |
| | 774 | 285 | CRKKL 290 |
| Sterol/retinol dehydrogenase | 775 | 152 | VRKARG 157 |
| | 776 | 152 | VRKARG 157 |
| Glycogen [starch] synthase liver | 777 | 554 | DRRFRS 559 |
| | 778 | 578 | SRRQRI 583 |
| | 779 | 554 | DRRFRS 559 |
| | 780 | 578 | SRRQRI 583 |
| Estrogen-related receptor gamma | 781 | 173 | TKRRRK 178 |
| | 782 | 353 | VKYKS 358 |
| | 783 | 173 | TKRRRK 178 |
| | 784 | 353 | VKYKS 358 |
| Neural retina-specific leucine zipper protein | 785 | 162 | QRRRTLKN 169 |
| Cytosolic phospholipase A2-gamma | 786 | 514 | NKKKILRE 521 |
| | 787 | 31 | LKKLRI 36 |
| | 788 | 218 | FKKGRL 223 |
| | 789 | 428 | CRRHKI 433 |
| | 790 | 31 | LKKLRI 36 |
| Cytosolic phospholipase A2-gamma | 791 | 218 | FKKGRL 223 |
| | 792 | 428 | CRRHKI 433 |

TABLE 3-continued

| | SEQ ID NO: | | |
|---|---|---|---|
| GLE1 | 793 | 415 | AKKIKM 420 |
| | 794 | 415 | AKKIKM 420 |
| Multiple exostoses type II protein EAXT.2 | 795 | 296 | VRKRCHKH 303 |
| | 796 | 659 | RKKFKC 664 |
| | 797 | 659 | RKKFKC 664 |
| Cyclic-AMP-dependent transcription factor ATF-7 | 798 | 86 | EKKARS 91 |
| | 799 | 332 | GRRRRT 337 |
| | 800 | 344 | ERRQRF 349 |
| | 801 | 86 | EKKARS 91 |
| | 802 | 332 | GRRRRT 337 |
| | 803 | 344 | ERRQRF 349 |
| Protein kinase/ endoribonulcease | 804 | 886 | LRKFRT 891 |
| | 805 | 886 | LRKFRT 891 |
| Transcription factor E2F6 | 806 | 23 | RRRCRD 28 |
| | 807 | 59 | VKRPRF 64 |
| | 808 | 98 | VKRRRV 103 |
| | 809 | 117 | EKKSKN 122 |
| | 810 | 23 | RRRCRD 28 |
| | 811 | 59 | VKRPRF 64 |
| | 812 | 98 | VKRRRV 103 |
| | 813 | 117 | EKKSKN 122 |
| MAP kinase-activating death domain protein | 814 | 1333 | IRKKVRRL 1340 |
| | 815 | 160 | KRRAKA 165 |
| | 816 | 943 | MKKVRR 948 |
| | 817 | 1034 | DKRKRS 1039 |
| | 818 | 1334 | RKKVRR 1339 |
| | 819 | 1453 | TKKCRE 1458 |
| | 820 | 160 | KRRAKA 165 |
| | 821 | 943 | MKKVRR 948 |
| | 822 | 1034 | DKRKRS 1039 |
| | 823 | 1334 | RKKVRR 1339 |
| | 824 | 1453 | TKKCRE 1458 |
| Orphan nuclear receptor PXR | 825 | 126 | KRKKSERT 133 |
| | 826 | 87 | TRKTRR 92 |
| | 827 | 125 | IKRKKS 130 |
| | 828 | 87 | TRKTRR 92 |
| | 829 | 125 | IKRKKS 130 |
| LENS EPITHELIUM-DERIVED GROWTH FACTOR | 830 | 149 | RKRKAEKQ 156 |
| | 831 | 286 | KKRKGGRN 293 |
| | 832 | 145 | ARRGRK 150 |
| | 833 | 178 | PKRGRP 183 |
| | 834 | 285 | EKKRKG 290 |
| | 835 | 313 | DRKRKQ 318 |
| | 836 | 400 | LKKIRR 405 |
| | 837 | 337 | VKKVEKKRE 345 |
| | 838 | 145 | ARRGRK 150 |
| | 839 | 178 | PKRGRP 183 |
| | 840 | 285 | EKKRKG 290 |
| | 841 | 313 | DRKRKQ 318 |
| | 842 | 400 | LKKIRR 405 |
| LIM homeobox protein cofactor | 843 | 255 | TKRRKRKN 262 |
| | 844 | 255 | TKRRKR 260 |
| | 845 | 255 | TKRRKR 260 |
| MULTIPLE MEMBRANE SPANNING RECEPTOR TRC8 | 846 | 229 | WKRIRF 234 |
| | 847 | 229 | WKRIRF 234 |
| Transcription factor SUPT3H | 848 | 172 | DKKKLRRL 179 |
| | 849 | 169 | MRKDKK 174 |
| | 850 | 213 | NKRQKI 218 |
| | 851 | 169 | MRKDKK 174 |
| | 852 | 213 | NKRQKI 218 |
| GEMININ | 853 | 50 | KRKHFN 55 |
| | 854 | 104 | EKRRKA 109 |
| | 855 | 50 | KRKHRN 55 |
| | 856 | 104 | EKRRKA 109 |

TABLE 3-continued

| | SEQ ID NO: | | |
|---|---|---|---|
| Cell cycle-regulated factor p78 | 857 | 165 | EKKKVSKA 172 |
| | 858 | 124 | IKRKKF 129 |
| | 859 | 188 | TKRVKK 193 |
| | 860 | 381 | DRRQKR 386 |
| | 861 | 124 | IKRKKF 129 |
| | 862 | 188 | TKRVKK 193 |
| | 863 | 381 | DRRQKR 386 |
| lymphocyte antigen 6 complex, locus D | 864 | 61 | QRKGRK 66 |
| | 865 | 85 | ARRLRA 90 |
| | 866 | 61 | QRKGRK 66 |
| | 867 | 85 | ARRLRA 90 |
| Delta 1-pyrroline-5-carboxylate synthetase | 868 | 455 | LRRTRI 460 |
| | 869 | 455 | LRRTRI 460 |
| B CELL LINKER PROTEIN BLINK | 870 | 36 | IKKLKV 41 |
| | 871 | 36 | IKKLKV 41 |
| B CELL LINKER PROTEIN BLINK-S | 872 | 36 | IKKLKV 41 |
| | 873 | 36 | IKKLKV 41 |
| fetal Alzheimer antigen | 874 | 5 | ARRRKRR 12 |
| | 875 | 16 | PRRRRRT 23 |
| | 876 | 93 | WKKKTSRP 100 |
| | 877 | 5 | ARRRRK 10 |
| | 878 | 16 | PRRRRR 21 |
| | 879 | 26 | PRRPRI 31 |
| | 880 | 35 | TRRMRW 40 |
| | 881 | 5 | ARRRRK 10 |
| | 882 | 16 | PRRRRR 21 |
| | 883 | 26 | PRRPRI 31 |
| | 884 | 35 | TRRMRW 40 |
| Transient receptor potential channel zeta splice variant | 885 | 505 | CKKKMRRK 512 |
| | 886 | 506 | KKKMRR 511 |
| | 887 | 676 | HRRSKQ 681 |
| | 888 | 506 | KKKNRR 511 |
| | 889 | 676 | HRRSKQ 681 |
| Myofibrillogenesis regulator MR-2 | 890 | 65 | RKRGKN 70 |
| | 891 | 65 | RKRGKN 70 |
| SH2 domain-containing phosphatase anchor protein 2c | 892 | 269 | IKKRSLRS 276 |
| immunoglobulin super-family, member 3 | 893 | 394 | SKRPKN 399 |
| | 894 | 394 | SKRPKN 399 |
| Meis (mouse) homolog 3 | 895 | 112 | PRRSRR 117 |
| | 896 | 120 | WRRTRG 125 |
| | 897 | 112 | PRRSRR 117 |
| | 898 | 120 | WRRTRG 125 |
| Deleted in azoospermia 2 | 899 | 105 | GKKLKL 110 |
| | 900 | 114 | IRKQKL 119 |
| | 901 | 105 | GKKLKL 110 |
| | 902 | 114 | IRKQKL 119 |
| Centaurin gamma3 | 903 | 543 | NRKKHRRK 550 |
| | 904 | 544 | RKHHRR 549 |
| | 905 | 544 | RKHHRR 549 |
| Pre-B-cell leukemia transcription factor-1 | 906 | 233 | ARRKRR 238 |
| | 907 | 286 | NKRIRY 291 |
| | 908 | 233 | ARRKRR 238 |
| | 909 | 286 | NKRIRY 291 |
| 60S ribosomal protein L13a | 910 | 112 | DKKKRM 117 |
| | 911 | 158 | KRKEKA 163 |
| | 912 | 167 | YRKKQ 172 |
| | 913 | 112 | DKKKRM 117 |
| | 914 | 158 | KRKEKA 163 |
| | 915 | 167 | YRKKQ 172 |

TABLE 3-continued

| | SEQ ID NO: | | |
|---|---|---|---|
| WD40- and FYVE-domain containing protein 3 | 916 | 388 | IKRLKI 393 |
| | 917 | 388 | IKRLKI 393 |
| LENG1 protein | 918 | 34 | RKRRGLRS 41 |
| | 919 | 84 | SRKKTRRM 91 |
| | 920 | 1 | MRRSRA 6 |
| | 921 | 33 | ERKRRG 38 |
| | 922 | 85 | RKKTRR 90 |
| | 923 | 1 | MRRSRA 6 |
| | 924 | 33 | ERKRRG 38 |
| | 925 | 85 | RKKTRR 90 |
| MRIP2 | 926 | 375 | NKKHLKK 382 |
| G protein-coupled receptor | 927 | 430 | EKKKLKRH 437 |
| | 928 | 290 | WKKKRA 295 |
| | 929 | 395 | RKKAKF 400 |
| | 930 | 431 | KKKLKR 436 |
| | 931 | 290 | WKKKRA 295 |
| | 932 | 395 | RKKAKF 400 |
| | 933 | 431 | KKKLKR 436 |
| | 934 | 143 | LKKFRQ 148 |
| | 935 | 228 | LRKIRT 233 |
| | 936 | 143 | LKKFRQ 148 |
| | 937 | 228 | LRKIRT 233 |
| | 938 | 232 | QKRRHRA 239 |
| | 939 | 232 | QKRRH 237 |
| | 940 | 232 | QKRRH 237 |
| Sperm ion channel | 941 | 402 | QKRKTGRL 409 |
| A-kinase anchoring protein | 942 | 2232 | KRKKLVRD 2239 |
| | 943 | 2601 | EKRRRERE 2608 |
| | 944 | 2788 | EKKKKNKT 2795 |
| | 945 | 370 | RKKNKG 375 |
| | 946 | 1763 | SKKSKE 1768 |
| | 947 | 2200 | EKKVRL 2205 |
| | 948 | 2231 | LKRKKL 2236 |
| | 949 | 2601 | EKRRRE 2606 |
| | 950 | 2785 | EKKEKK 2790 |
| | 951 | 1992 | QKKDVVKRQ 2000 |
| | 952 | 370 | RKKNKG 375 |
| | 953 | 1763 | SKKSKE 1768 |
| | 954 | 2200 | EKKVRL 2205 |
| | 955 | 2231 | LKRKKL 2236 |
| | 956 | 2601 | EKRRRE 2606 |
| | 957 | 2785 | EKKEKK 2790 |
| Lymphocyte-specific protein LSP1 | 958 | 315 | GKRYKF 320 |
| | 959 | 315 | GKRYKF 320 |
| similar to signaling lymphocytic activation molecule (*H. sapiens*) | 960 | 261 | RRRGKT 266 |
| | 961 | 261 | RRRGKT 266 |
| Dermatan-4-sulfotransferase-1 | 962 | 242 | VRRYRA 247 |
| | 963 | 242 | VRRYRA 247 |
| Moesin | 964 | 291 | MRRRKP 296 |
| | 965 | 325 | EKKKRE 330 |
| | 966 | 291 | MRRRKP 296 |
| | 967 | 325 | EKKKRE 330 |
| A-Raf proto-oncogene serine/threonine-protein kinase | 968 | 288 | KKKVKN 293 |
| | 969 | 358 | LRKTRH 363 |
| | 970 | 288 | KKKVKN 293 |
| | 971 | 358 | LRKTRH 363 |
| Cytochrome P450 2C18 | 972 | 117 | GKRWKE 122 |
| | 973 | 117 | GKRWKE 122 |
| | 974 | 117 | GKRWKE 122 |
| | 975 | 156 | LRKTKA 161 |
| | 976 | 117 | GKRWKE 122 |
| | 977 | 156 | LRKTKA 161 |

TABLE 3-continued

| | SEQ ID NO: | | |
|---|---|---|---|
| Protein tyrosine phosphatase non-receptor type 3 | 978 | 594 | IRRRAVRS 601 |
| | 979 | 263 | FKRKKF 268 |
| | 980 | 388 | IRKPRH 393 |
| | 981 | 874 | VRKMRD 879 |
| | 982 | 263 | FKRKKF 268 |
| | 983 | 388 | IRKPRH 393 |
| | 984 | 874 | VRKMRD 879 |
| similar to kallikrein 7 (chymotryptic, stratum corneum) | 985 | 15 | VKKVRL 20 |
| | 986 | 15 | VKKVRL 20 |
| Hormone sensitive lipase | 987 | 703 | ARRLRN 708 |
| | 988 | 703 | ARRLRN 708 |
| 40S ribosomal protein S30 | 989 | 25 | KKKKTGRA 32 |
| | 990 | 23 | EKKKKK 28 |
| | 991 | 23 | EKKKKK 28 |
| Zinc finger protein 91 | 992 | 617 | LRRHKR 622 |
| | 993 | 617 | LRRHKR 622 |
| NNP-1 protein | 994 | 320 | NRKRLYKV 327 |
| | 995 | 387 | ERKSRRR 394 |
| | 996 | 432 | QRRRTPRP 439 |
| | 997 | 454 | EKKKKRRE 461 |
| | 998 | 29 | VRKLRK 34 |
| | 999 | 355 | GRRQKK 360 |
| | 1000 | 361 | TKKQKR 366 |
| | 1001 | 388 | RKRSRR 393 |
| | 1002 | 454 | EKKKKR 459 |
| | 1003 | 29 | VRKLRK 34 |
| | 1004 | 355 | GRRQKK 360 |
| | 1005 | 361 | TKKQKR 366 |
| | 1006 | 388 | RKRSRR 393 |
| | 1007 | 454 | EKKKKR 459 |
| Methionyl-tRNA synthetase | 1008 | 725 | WKRIKG 730 |
| | 1009 | 725 | WKRIKG 730 |
| ELMO2 | 1010 | 560 | NRRRQERF 567 |
| Meningioma-expressed antigen 6/11 | 1011 | 432 | RKEAKD 437 |
| | 1012 | 432 | RKRAKD 437 |
| Inositol polyphosphate 4-phosphatase type I-beta | 1013 | 375 | LRKKLHKF 382 |
| | 1014 | 829 | ARKNKN 834 |
| | 1015 | 829 | ARKNKN 834 |
| | 1016 | 815 | SKKRKN 820 |
| | 1017 | 815 | SKKRKN 820 |
| C7ORF12 | 1018 | 40 | SRRYRG 45 |
| | 1019 | 338 | HRKNKP 343 |
| | 1020 | 40 | SRRYRG 45 |
| | 1021 | 338 | HRKNKP 343 |
| Rap guanine nucleotide exchange factor | 1022 | 138 | SRRRFRKI 145 |
| | 1023 | 1071 | QRKKRWRS 1078 |
| | 1024 | 1099 | HKKRARRS 1106 |
| | 1025 | 139 | RRRFRK 144 |
| | 1026 | 661 | SKKVKA 666 |
| | 1027 | 930 | LKRMKI 935 |
| | 1028 | 1071 | QRKKRW 1076 |
| | 1029 | 1100 | KKRARR 1105 |
| | 1030 | 1121 | ARKVKQ 1126 |
| | 1031 | 139 | RRRFRK 144 |
| | 1032 | 661 | SKKVKA 666 |
| | 1033 | 930 | LKRMKI 935 |
| | 1034 | 1071 | QRKKRW 1076 |
| | 1035 | 1100 | KKRARR 1105 |
| | 1036 | 1121 | ARKVKQ 1126 |

TABLE 3-continued

| | SEQ ID NO: | | |
|---|---|---|---|
| Sigma 1C adaptin | 1037 | 27 | ERKKITRE 34 |
| Alsin | 1038 | 883 | GRKRKE 888 |
| | 1039 | 883 | GRKRKE 888 |
| NOPAR2 | 1040 | 14 | LKRPRL 19 |
| | 1041 | 720 | VKREKP 725 |
| | 1042 | 14 | LKRPRL 19 |
| | 1043 | 720 | VKREKP 725 |
| AT-binding transcription factor 1 | 1044 | 294 | SKRPKT 299 |
| | 1045 | 961 | EKKNKL 966 |
| | 1046 | 1231 | NKRPRT 1236 |
| | 1047 | 1727 | DKRLRT 1732 |
| | 1048 | 2032 | QKRFRT 2037 |
| | 1049 | 2087 | EKKSKL 2092 |
| | 1050 | 2317 | QRKDKD 2322 |
| | 1051 | 2343 | PKKEKG 2348 |
| | 1052 | 294 | SKRPKT 299 |
| | 1053 | 961 | EKKNKL 966 |
| | 1054 | 1231 | NKRPRT 1236 |
| | 1055 | 1727 | DKRLRT 1732 |
| | 1056 | 2032 | QKRFRT 2037 |
| | 1057 | 2087 | EKKSKL 2092 |
| | 1058 | 2317 | QRKDKD 2322 |
| | 1059 | 2343 | PKKEKG 2348 |
| Suppressin | 1060 | 232 | YKRRKK 237 |
| | 1061 | 232 | YKRRKK 237 |
| Midline 1 protein | 1062 | 100 | TRRERA 105 |
| | 1063 | 494 | HRKLKV 499 |
| | 1064 | 100 | TRRERA 105 |
| | 1065 | 494 | HRKLKV 499 |
| High mobility group protein 2a | 1066 | 6 | PKKPKG 11 |
| | 1067 | 84 | GKKKD 89 |
| | 1068 | 6 | PKKPKG 11 |
| | 1069 | 84 | GKKKD 89 |

This application claims priority to A 1952/2003 filed on Dec. 4, 2003, the entirety of which is hereby incorporated by reference.

---

The invention claimed is:

1. A method of making modified human Interleukin-8 (IL-8) protein, wherein the method comprises:
   substituting one or more amino acids in SEQ ID NO. 16 of human IL-8, wherein the amino acid substitutions are selected from the group consisting of:
   (A) Arg, Lys or His substitution at position 70, and
   (B) Arg, Lys or His substitution at position 71.

2. The method of making modified human IL-8 according to claim 1, wherein the amino acid substitutions are:
   (A) Arg, Lys or His substitution at position 70, and
   (B) Arg, Lys or His substitution at position 71.

3. The method of making modified human IL-8 according to claim 1, wherein the amino acid substitutions are selected from the group consisting of:
   (C) Arg, Lys or His substitution at position 17, and
   (D) Arg, Lys or His substitution at position 21.

4. The method of making modified human IL-8 according to claim 2, wherein the amino acid substitutions are selected from the group consisting of:
(C) Arg, Lys or His substitution at position 17, and
(D) Arg, Lys or His substitution at position 21.

5. The method of making modified human IL-8 according to claim 1, wherein the amino acid substitutions are:
(A) Arg, Lys or His substitution at position 17, and
(B) Arg, Lys or His substitution at position 21.

6. The method of making modified human IL-8 according to claim 2, wherein the amino acid substitutions are:
(A) Arg, Lys or His substitution at position 17, and
(B) Arg, Lys or His substitution at position 21.

7. The method of making modified human IL-8 according to claim 1, wherein the modified human IL-8 is further modified by deleting amino acids at positions 1 through 6 of SEQ ID NO: 16.

8. The method of making modified human IL-8 according to claim 2, wherein the modified human IL-8 is further modified by deleting amino acids at positions 1 through 6 of SEQ ID NO: 16.

9. A method of making modified human Interleukin-8 (IL-8) protein, wherein the method comprises:
(I) substituting one or more amino acids in SEQ ID NO. 16 of human IL-8, wherein the amino acid substitutions are selected from the group consisting of:
(A) Arg, Lys or His substitution at position 70,
(B) Arg, Lys or His substitution at position 71,
(C) Arg, Lys or His substitution at position 17, and
(D) Arg, Lys or His substitution at position 21;
and
(II) deleting amino acids at positions 1 through 6 of SEQ ID NO. 16.

10. The method of making modified human IL-8 according to claim 9, wherein the amino acid substitutions are:
(A) Arg, Lys or His substitution at position 70, and
(B) Arg, Lys or His substitution at position 71.

11. The method of making modified human IL-8 according to claim 9, wherein the amino acid substitutions are:
(A) Arg, Lys or His substitution at position 70,
(B) Arg, Lys or His substitution at position 71, and
(C) Arg, Lys or His substitution at position 17.

12. The method of making modified human IL-8 according to claim 9, wherein the amino acid substitutions are:
(A) Arg, Lys or His substitution at position 70,
(B) Arg, Lys or His substitution at position 71, and
(C) Arg, Lys or His substitution at position 21.

13. A method of making modified human Interleukin-8 (IL-8) protein, wherein the method comprises:
substituting one or more amino acids in SEQ ID NO. 16 of human IL-8, wherein the amino acid substitutions are:
(A) Arg, Lys or His substitution at position 70,
(B) Arg, Lys or His substitution at position 71,
(C) Arg, Lys or His substitution at position 17, and
(D) Arg, Lys or His substitution at position 21.

14. The method of making modified human IL-8 according to claim 13, wherein the modified human Interleukin-8 is further modified by deleting amino acids at positions 1 through 6 of SEQ ID NO: 16.

15. A method of making modified human Interleukin-8 (IL-8) protein, wherein the method comprises:
substituting one or more amino acids in SEQ ID NO. 16 of human IL-8, wherein the amino acid substitutions are:
(A) Arg, Lys or His substitution at position 70, and
at least one selected from the group consisting of:
(B) Arg, Lys or His substitution at position 17, and
(C) Arg, Lys or His substitution at position 21.

16. A method of making modified human Interleukin-8 (IL-8) protein, wherein the method comprises:
substituting one or more amino acids in SEQ ID NO. 16 of human IL-8, wherein the amino acid substitutions are:
(A) Arg, Lys or His substitution at position 71,
and at least one selected from the group consisting of:
(B) Arg, Lys or His substitution at position 17, and
(C) Arg, Lys or His substitution at position 21.

* * * * *

SEQUENCE LISTING

```
<160> NUMBER OF SEQ ID NOS: 1074

<210> SEQ ID NO 1
<211> LENGTH: 6
<212> TYPE: PRT
<213> ORGANISM: Homo sapiens

<400> SEQUENCE: 1

Lys Ser Leu Ser Leu Ser
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser Lys Ser Lys Lys Leu Ser
1               5

<210> SEQ ID NO 3
<211> LENGTH: 6
<212> TYPE: PRT
<213> ORGANISM: Homo sapiens

<400> SEQUENCE: 3

Trp Ile Ala Ser His Thr
1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 4

Trp Lys Ala Lys His Lys
1               5

<210> SEQ ID NO 5
<211> LENGTH: 8
<212> TYPE: PRT
<213> ORGANISM: Homo sapiens

<400> SEQUENCE: 5

Met Leu Asp Ala Glu Arg Leu Lys
1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Met Lys Lys Ala Lys Arg Leu Lys
1               5

<210> SEQ ID NO 7
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
caccatgtgt cagtgtataa agacatactc c                              31

<210> SEQ ID NO 8
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
caccatgtgt cagtgtataa agacatactc caaacctagg caccccaaaa ggata     55

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ttatgaattc ctagccctct t                                         21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 10
ttatgaattc ttagccctct t                                              21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ttatgacttc tcagccctct t                                              21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ttatgacttc ttagccctct t                                              21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ttatgacttc ctagccctct t                                              21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ttatgacctc ttagccctct t                                              21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ttatgacctc ctagccctct t                                              21

<210> SEQ ID NO 16
<211> LENGTH: 72
<212> TYPE: PRT
<213> ORGANISM: Homo sapiens
```

-continued

```
<400> SEQUENCE: 16

Ser Ala Lys Glu Leu Arg Cys Gln Cys Ile Lys Thr Tyr Ser Lys Pro
1               5                   10                  15

Phe His Pro Lys Phe Ile Lys Glu Leu Arg Val Ile Glu Ser Gly Pro
                20                  25                  30

His Cys Ala Asn Thr Glu Ile Ile Val Lys Leu Ser Asp Gly Arg Glu
            35                  40                  45

Leu Cys Leu Asp Pro Lys Glu Asn Trp Val Gln Arg Val Val Glu Lys
        50                  55                  60

Phe Leu Lys Arg Ala Glu Asn Ser
65                  70

<210> SEQ ID NO 17
<211> LENGTH: 73
<212> TYPE: PRT
<213> ORGANISM: Homo sapiens

<400> SEQUENCE: 17

Ala Ser Val Ala Thr Glu Leu Arg Cys Gln Cys Leu Gln Thr Leu Gln
1               5                   10                  15

Gly Ile His Pro Lys Asn Ile Gln Ser Val Asn Val Lys Ser Pro Gly
                20                  25                  30

Pro His Cys Ala Gln Thr Glu Val Ile Ala Thr Leu Lys Asn Gly Arg
            35                  40                  45

Lys Ala Cys Leu Asn Pro Ala Ser Pro Ile Val Lys Lys Ile Ile Glu
        50                  55                  60

Lys Met Leu Asn Ser Asp Lys Ser Asn
65                  70

<210> SEQ ID NO 18
<211> LENGTH: 73
<212> TYPE: PRT
<213> ORGANISM: Homo sapiens

<400> SEQUENCE: 18

Ala Pro Leu Ala Thr Glu Leu Arg Cys Gln Cys Leu Gln Thr Leu Gln
1               5                   10                  15

Gly Ile His Leu Lys Asn Ile Gln Ser Val Lys Val Lys Ser Pro Gly
                20                  25                  30

Pro His Cys Ala Gln Thr Glu Val Ile Ala Thr Leu Lys Asn Gly Gln
            35                  40                  45

Lys Ala Cys Leu Asn Pro Ala Ser Pro Met Val Lys Lys Ile Ile Glu
        50                  55                  60

Lys Met Leu Lys Asn Gly Lys Ser Asn
65                  70

<210> SEQ ID NO 19
<211> LENGTH: 70
<212> TYPE: PRT
<213> ORGANISM: Homo sapiens

<400> SEQUENCE: 19

Ala Glu Leu Arg Cys Leu Cys Ile Lys Thr Thr Ser Gly Ile His Pro
1               5                   10                  15

Lys Asn Ile Gln Ser Leu Glu Val Ile Gly Lys Gly Thr His Cys Asn
                20                  25                  30

Gln Val Glu Val Ile Ala Thr Leu Lys Asp Gly Arg Lys Ile Cys Leu
            35                  40                  45
```

```
Asp Pro Asp Ala Pro Arg Ile Lys Lys Ile Val Gln Lys Lys Leu Ala
    50                  55                  60

Gly Asp Glu Ser Ala Asp
65                  70

<210> SEQ ID NO 20
<211> LENGTH: 70
<212> TYPE: PRT
<213> ORGANISM: Homo sapiens

<400> SEQUENCE: 20

Glu Ala Glu Glu Asp Gly Asp Leu Gln Cys Leu Cys Val Lys Thr Thr
1               5                   10                  15

Ser Gln Val Arg Pro Arg His Ile Thr Ser Leu Glu Val Ile Lys Ala
                20                  25                  30

Gly Pro His Cys Pro Thr Ala Gln Leu Ile Ala Thr Leu Lys Asn Gly
            35                  40                  45

Arg Lys Ile Cys Leu Asp Leu Gln Ala Pro Leu Tyr Lys Lys Ile Ile
        50                  55                  60

Lys Lys Leu Leu Glu Ser
65                  70

<210> SEQ ID NO 21
<211> LENGTH: 67
<212> TYPE: PRT
<213> ORGANISM: Homo sapiens

<400> SEQUENCE: 21

Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
                20                  25                  30

Asn Cys Ala Leu Gln Ile Val Ala Arg Leu Lys Asn Asn Asn Arg Gln
            35                  40                  45

Val Cys Ile Asp Pro Lys Leu Lys Trp Ile Gln Glu Tyr Leu Glu Lys
        50                  55                  60

Ala Leu Asn
65

<210> SEQ ID NO 22
<211> LENGTH: 68
<212> TYPE: PRT
<213> ORGANISM: Homo sapiens

<400> SEQUENCE: 22

Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
                20                  25                  30

Lys Cys Ser Asn Pro Ala Val Val Phe Val Thr Arg Lys Asn Arg Gln
            35                  40                  45

Val Cys Ala Asn Pro Glu Lys Lys Trp Val Arg Glu Tyr Ile Asn Ser
        50                  55                  60

Leu Glu Met Ser
65
```

```
<210> SEQ ID NO 23
<211> LENGTH: 76
<212> TYPE: PRT
<213> ORGANISM: Homo sapiens

<400> SEQUENCE: 23

Gln Pro Asp Ser Val Ser Ile Pro Ile Thr Cys Cys Phe Asn Val Ile
1               5                   10                  15

Asn Arg Lys Ile Pro Ile Gln Arg Leu Glu Ser Tyr Thr Arg Ile Thr
            20                  25                  30

Asn Ile Gln Cys Pro Lys Glu Ala Val Ile Phe Lys Thr Lys Arg Gly
        35                  40                  45

Lys Glu Val Cys Ala Asp Pro Lys Glu Arg Trp Val Arg Asp Ser Met
    50                  55                  60

Lys His Leu Asp Gln Ile Phe Gln Asn Leu Lys Pro
65                  70                  75

<210> SEQ ID NO 24
<211> LENGTH: 76
<212> TYPE: PRT
<213> ORGANISM: Homo sapiens

<400> SEQUENCE: 24

Gln Pro Val Gly Ile Asn Thr Ser Thr Thr Cys Cys Tyr Arg Phe Ile
1               5                   10                  15

Asn Lys Lys Ile Pro Lys Gln Arg Leu Glu Ser Tyr Arg Arg Thr Thr
            20                  25                  30

Ser Ser His Cys Pro Arg Glu Ala Val Ile Phe Lys Thr Lys Leu Asp
        35                  40                  45

Lys Glu Ile Cys Ala Asp Pro Thr Gln Lys Trp Val Gln Asp Phe Met
    50                  55                  60

Lys His Leu Asp Lys Lys Thr Gln Thr Pro Lys Leu
65                  70                  75

<210> SEQ ID NO 25
<211> LENGTH: 69
<212> TYPE: PRT
<213> ORGANISM: Homo sapiens

<400> SEQUENCE: 25

Ser Leu Ala Ala Asp Thr Pro Thr Ala Cys Cys Phe Ser Tyr Thr Ser
1               5                   10                  15

Arg Gln Ile Pro Gln Asn Phe Ile Ala Asp Tyr Phe Glu Thr Ser Ser
            20                  25                  30

Gln Cys Ser Lys Pro Gly Val Ile Phe Leu Thr Lys Arg Ser Arg Gln
        35                  40                  45

Val Cys Ala Asp Pro Ser Glu Glu Trp Val Gln Lys Tyr Val Ser Asp
    50                  55                  60

Leu Glu Leu Ser Ala
65

<210> SEQ ID NO 26
<211> LENGTH: 69
<212> TYPE: PRT
<213> ORGANISM: Homo sapiens
```

-continued

<400> SEQUENCE: 26

Ala Pro Met Gly Ser Asp Pro Pro Thr Ala Cys Cys Phe Ser Tyr Thr
1               5                   10                  15

Ala Arg Lys Leu Pro Arg Asn Phe Val Val Asp Tyr Tyr Glu Thr Ser
            20                  25                  30

Ser Leu Cys Ser Gln Pro Ala Val Val Phe Gln Thr Lys Arg Ser Lys
        35                  40                  45

Gln Val Cys Ala Asp Pro Ser Glu Ser Trp Val Gln Glu Tyr Val Tyr
    50                  55                  60

Asp Leu Glu Leu Asn
65

<210> SEQ ID NO 27
<211> LENGTH: 77
<212> TYPE: PRT
<213> ORGANISM: Homo sapiens

<400> SEQUENCE: 27

Met Asp Arg Phe His Ala Thr Ser Ala Asp Cys Cys Ile Ser Tyr Thr
1               5                   10                  15

Pro Arg Ser Ile Pro Cys Ser Leu Leu Glu Ser Tyr Phe Glu Thr Asn
            20                  25                  30

Ser Glu Cys Ser Lys Pro Gly Val Ile Phe Leu Thr Lys Lys Gly Arg
        35                  40                  45

Arg Phe Cys Ala Asn Pro Ser Asp Lys Gln Val Gln Val Cys Met Arg
    50                  55                  60

Met Leu Lys Leu Asp Thr Arg Ile Lys Thr Arg Lys Asn
65                  70                  75

<210> SEQ ID NO 28
<211> LENGTH: 66
<212> TYPE: PRT
<213> ORGANISM: Homo sapiens

<400> SEQUENCE: 28

His Phe Ala Ala Asp Cys Cys Thr Ser Tyr Ile Ser Gln Ser Ile Pro
1               5                   10                  15

Cys Ser Leu Met Lys Ser Tyr Phe Glu Thr Ser Ser Glu Cys Ser Lys
            20                  25                  30

Pro Gly Val Ile Phe Leu Thr Lys Lys Gly Arg Gln Val Cys Ala Lys
        35                  40                  45

Pro Ser Gly Pro Gly Val Gln Asp Cys Met Lys Lys Leu Lys Pro Tyr
    50                  55                  60

Ser Ile
65

<210> SEQ ID NO 29
<211> LENGTH: 6
<212> TYPE: PRT
<213> ORGANISM: Homo sapiens

<400> SEQUENCE: 29

Thr Arg Arg Ala Lys Glu
1               5

<210> SEQ ID NO 30
<211> LENGTH: 6
<212> TYPE: PRT
<213> ORGANISM: Homo sapiens

```
<400> SEQUENCE: 30

Gln Lys Lys Ile Arg Ser
1               5

<210> SEQ ID NO 31
<211> LENGTH: 6
<212> TYPE: PRT
<213> ORGANISM: Homo sapiens

<400> SEQUENCE: 31

Pro Lys Arg Arg Lys Asn
1               5

<210> SEQ ID NO 32
<211> LENGTH: 6
<212> TYPE: PRT
<213> ORGANISM: Homo sapiens

<400> SEQUENCE: 32

Thr Arg Arg Ala Lys Glu
1               5

<210> SEQ ID NO 33
<211> LENGTH: 6
<212> TYPE: PRT
<213> ORGANISM: Homo sapiens

<400> SEQUENCE: 33

Gln Lys Lys Ile Arg Ser
1               5

<210> SEQ ID NO 34
<211> LENGTH: 6
<212> TYPE: PRT
<213> ORGANISM: Homo sapiens

<400> SEQUENCE: 34

Pro Lys Arg Arg Lys Asn
1               5

<210> SEQ ID NO 35
<211> LENGTH: 8
<212> TYPE: PRT
<213> ORGANISM: Homo sapiens

<400> SEQUENCE: 35

Ser Lys Arg Arg Gly Lys Lys Val
1               5

<210> SEQ ID NO 36
<211> LENGTH: 6
<212> TYPE: PRT
<213> ORGANISM: Homo sapiens

<400> SEQUENCE: 36

Glu Arg Arg Leu Lys Met
1               5

<210> SEQ ID NO 37
<211> LENGTH: 6
<212> TYPE: PRT
<213> ORGANISM: Homo sapiens
```

```
<400> SEQUENCE: 37

Lys Arg Arg Gly Lys Lys
1               5

<210> SEQ ID NO 38
<211> LENGTH: 6
<212> TYPE: PRT
<213> ORGANISM: Homo sapiens

<400> SEQUENCE: 38

Glu Arg Arg Leu Lys Met
1               5

<210> SEQ ID NO 39
<211> LENGTH: 6
<212> TYPE: PRT
<213> ORGANISM: Homo sapiens

<400> SEQUENCE: 39

Lys Arg Arg Gly Lys Lys
1               5

<210> SEQ ID NO 40
<211> LENGTH: 8
<212> TYPE: PRT
<213> ORGANISM: Homo sapiens

<400> SEQUENCE: 40

Glu Lys Arg Arg Arg Ala Arg Ile
1               5

<210> SEQ ID NO 41
<211> LENGTH: 6
<212> TYPE: PRT
<213> ORGANISM: Homo sapiens

<400> SEQUENCE: 41

Glu Lys Arg Arg Arg Ala
1               5

<210> SEQ ID NO 42
<211> LENGTH: 6
<212> TYPE: PRT
<213> ORGANISM: Homo sapiens

<400> SEQUENCE: 42

Glu Lys Arg Arg Arg Ala
1               5

<210> SEQ ID NO 43
<211> LENGTH: 8
<212> TYPE: PRT
<213> ORGANISM: Homo sapiens

<400> SEQUENCE: 43

Met Lys Lys Lys Lys Lys Lys Lys
1               5

<210> SEQ ID NO 44
<211> LENGTH: 6
<212> TYPE: PRT
<213> ORGANISM: Homo sapiens
```

```
<400> SEQUENCE: 44

Met Lys Lys Lys Lys Lys
1               5

<210> SEQ ID NO 45
<211> LENGTH: 6
<212> TYPE: PRT
<213> ORGANISM: Homo sapiens

<400> SEQUENCE: 45

Met Lys Lys Lys Lys Lys
1               5

<210> SEQ ID NO 46
<211> LENGTH: 8
<212> TYPE: PRT
<213> ORGANISM: Homo sapiens

<400> SEQUENCE: 46

Met Lys Lys Lys Lys Lys Lys Lys
1               5

<210> SEQ ID NO 47
<211> LENGTH: 6
<212> TYPE: PRT
<213> ORGANISM: Homo sapiens

<400> SEQUENCE: 47

Met Lys Lys Lys Lys Lys
1               5

<210> SEQ ID NO 48
<211> LENGTH: 6
<212> TYPE: PRT
<213> ORGANISM: Homo sapiens

<400> SEQUENCE: 48

Met Lys Lys Lys Lys Lys
1               5

<210> SEQ ID NO 49
<211> LENGTH: 6
<212> TYPE: PRT
<213> ORGANISM: Homo sapiens

<400> SEQUENCE: 49

Arg Arg Arg Leu Arg Ser
1               5

<210> SEQ ID NO 50
<211> LENGTH: 6
<212> TYPE: PRT
<213> ORGANISM: Homo sapiens

<400> SEQUENCE: 50

Val Arg Lys Leu Lys Gly
1               5

<210> SEQ ID NO 51
<211> LENGTH: 6
<212> TYPE: PRT
<213> ORGANISM: Homo sapiens
```

```
<400> SEQUENCE: 51

Leu Arg Lys Ala Arg Asp
1               5

<210> SEQ ID NO 52
<211> LENGTH: 6
<212> TYPE: PRT
<213> ORGANISM: Homo sapiens

<400> SEQUENCE: 52

Arg Arg Lys Leu Arg Glu
1               5

<210> SEQ ID NO 53
<211> LENGTH: 6
<212> TYPE: PRT
<213> ORGANISM: Homo sapiens

<400> SEQUENCE: 53

Ala Lys Lys Gly Lys Gly
1               5

<210> SEQ ID NO 54
<211> LENGTH: 6
<212> TYPE: PRT
<213> ORGANISM: Homo sapiens

<400> SEQUENCE: 54

Ala Lys Lys Leu Arg Glu
1               5

<210> SEQ ID NO 55
<211> LENGTH: 6
<212> TYPE: PRT
<213> ORGANISM: Homo sapiens

<400> SEQUENCE: 55

Arg Arg Arg Leu Arg Ser
1               5

<210> SEQ ID NO 56
<211> LENGTH: 6
<212> TYPE: PRT
<213> ORGANISM: Homo sapiens

<400> SEQUENCE: 56

Val Arg Lys Leu Lys Gly
1               5

<210> SEQ ID NO 57
<211> LENGTH: 6
<212> TYPE: PRT
<213> ORGANISM: Homo sapiens

<400> SEQUENCE: 57

Leu Arg Lys Ala Arg Asp
1               5

<210> SEQ ID NO 58
<211> LENGTH: 6
<212> TYPE: PRT
<213> ORGANISM: Homo sapiens
```

```
<400> SEQUENCE: 58

Arg Arg Lys Leu Arg Glu
1               5

<210> SEQ ID NO 59
<211> LENGTH: 6
<212> TYPE: PRT
<213> ORGANISM: Homo sapiens

<400> SEQUENCE: 59

Ala Lys Lys Gly Lys Gly
1               5

<210> SEQ ID NO 60
<211> LENGTH: 6
<212> TYPE: PRT
<213> ORGANISM: Homo sapiens

<400> SEQUENCE: 60

Ala Lys Lys Leu Arg Glu
1               5

<210> SEQ ID NO 61
<211> LENGTH: 6
<212> TYPE: PRT
<213> ORGANISM: Homo sapiens

<400> SEQUENCE: 61

Glu Lys Arg Thr Lys Asp
1               5

<210> SEQ ID NO 62
<211> LENGTH: 6
<212> TYPE: PRT
<213> ORGANISM: Homo sapiens

<400> SEQUENCE: 62

Thr Lys Arg Lys Arg Val
1               5

<210> SEQ ID NO 63
<211> LENGTH: 6
<212> TYPE: PRT
<213> ORGANISM: Homo sapiens

<400> SEQUENCE: 63

Trp Lys Lys Lys Lys Val
1               5

<210> SEQ ID NO 64
<211> LENGTH: 6
<212> TYPE: PRT
<213> ORGANISM: Homo sapiens

<400> SEQUENCE: 64

Glu Lys Arg Thr Lys Asp
1               5

<210> SEQ ID NO 65
<211> LENGTH: 6
<212> TYPE: PRT
<213> ORGANISM: Homo sapiens
```

```
<400> SEQUENCE: 65

Thr Lys Arg Lys Arg Val
1               5

<210> SEQ ID NO 66
<211> LENGTH: 6
<212> TYPE: PRT
<213> ORGANISM: Homo sapiens

<400> SEQUENCE: 66

Trp Lys Lys Lys Lys Val
1               5

<210> SEQ ID NO 67
<211> LENGTH: 6
<212> TYPE: PRT
<213> ORGANISM: Homo sapiens

<400> SEQUENCE: 67

Pro Arg Arg Ile Lys Ala
1               5

<210> SEQ ID NO 68
<211> LENGTH: 6
<212> TYPE: PRT
<213> ORGANISM: Homo sapiens

<400> SEQUENCE: 68

Lys Arg Arg Thr Arg Val
1               5

<210> SEQ ID NO 69
<211> LENGTH: 6
<212> TYPE: PRT
<213> ORGANISM: Homo sapiens

<400> SEQUENCE: 69

Pro Arg Arg Ile Lys Ala
1               5

<210> SEQ ID NO 70
<211> LENGTH: 6
<212> TYPE: PRT
<213> ORGANISM: Homo sapiens

<400> SEQUENCE: 70

Lys Arg Arg Thr Arg Val
1               5

<210> SEQ ID NO 71
<211> LENGTH: 8
<212> TYPE: PRT
<213> ORGANISM: Homo sapiens

<400> SEQUENCE: 71

Thr Lys Lys Lys Thr Arg Arg Arg
1               5

<210> SEQ ID NO 72
<211> LENGTH: 8
<212> TYPE: PRT
<213> ORGANISM: Homo sapiens
```

<400> SEQUENCE: 72

Gly Lys Arg Arg Arg Arg Gly
1               5

<210> SEQ ID NO 73
<211> LENGTH: 6
<212> TYPE: PRT
<213> ORGANISM: Homo sapiens

<400> SEQUENCE: 73

Ala Arg Lys Gly Lys Arg
1               5

<210> SEQ ID NO 74
<211> LENGTH: 6
<212> TYPE: PRT
<213> ORGANISM: Homo sapiens

<400> SEQUENCE: 74

Gly Lys Lys Thr Lys Lys
1               5

<210> SEQ ID NO 75
<211> LENGTH: 6
<212> TYPE: PRT
<213> ORGANISM: Homo sapiens

<400> SEQUENCE: 75

Thr Arg Arg Arg Arg Ala
1               5

<210> SEQ ID NO 76
<211> LENGTH: 6
<212> TYPE: PRT
<213> ORGANISM: Homo sapiens

<400> SEQUENCE: 76

Gly Lys Arg Arg Arg Arg
1               5

<210> SEQ ID NO 77
<211> LENGTH: 6
<212> TYPE: PRT
<213> ORGANISM: Homo sapiens

<400> SEQUENCE: 77

Ala Arg Lys Gly Lys Arg
1               5

<210> SEQ ID NO 78
<211> LENGTH: 6
<212> TYPE: PRT
<213> ORGANISM: Homo sapiens

<400> SEQUENCE: 78

Gly Lys Lys Thr Lys Lys
1               5

<210> SEQ ID NO 79
<211> LENGTH: 6
<212> TYPE: PRT
<213> ORGANISM: Homo sapiens

```
<400> SEQUENCE: 79

Thr Arg Arg Arg Arg Ala
1               5

<210> SEQ ID NO 80
<211> LENGTH: 6
<212> TYPE: PRT
<213> ORGANISM: Homo sapiens

<400> SEQUENCE: 80

Gly Lys Arg Arg Arg Arg
1               5

<210> SEQ ID NO 81
<211> LENGTH: 6
<212> TYPE: PRT
<213> ORGANISM: Homo sapiens

<400> SEQUENCE: 81

Ala Arg Lys Gln Lys Ala
1               5

<210> SEQ ID NO 82
<211> LENGTH: 6
<212> TYPE: PRT
<213> ORGANISM: Homo sapiens

<400> SEQUENCE: 82

Lys Lys Lys Ile Lys Glu
1               5

<210> SEQ ID NO 83
<211> LENGTH: 6
<212> TYPE: PRT
<213> ORGANISM: Homo sapiens

<400> SEQUENCE: 83

Ala Arg Lys Gln Lys Ala
1               5

<210> SEQ ID NO 84
<211> LENGTH: 6
<212> TYPE: PRT
<213> ORGANISM: Homo sapiens

<400> SEQUENCE: 84

Lys Lys Lys Ile Lys Glu
1               5

<210> SEQ ID NO 85
<211> LENGTH: 6
<212> TYPE: PRT
<213> ORGANISM: Homo sapiens

<400> SEQUENCE: 85

Val Arg Arg Cys Lys Ile
1               5

<210> SEQ ID NO 86
<211> LENGTH: 6
<212> TYPE: PRT
<213> ORGANISM: Homo sapiens
```

```
<400> SEQUENCE: 86

Val Arg Arg Cys Lys Ile
1               5

<210> SEQ ID NO 87
<211> LENGTH: 6
<212> TYPE: PRT
<213> ORGANISM: Homo sapiens

<400> SEQUENCE: 87

Glu Arg Arg Ala Arg Leu
1               5

<210> SEQ ID NO 88
<211> LENGTH: 6
<212> TYPE: PRT
<213> ORGANISM: Homo sapiens

<400> SEQUENCE: 88

Glu Arg Arg Ala Arg Leu
1               5

<210> SEQ ID NO 89
<211> LENGTH: 6
<212> TYPE: PRT
<213> ORGANISM: Homo sapiens

<400> SEQUENCE: 89

Met Lys Arg Leu Lys Val
1               5

<210> SEQ ID NO 90
<211> LENGTH: 6
<212> TYPE: PRT
<213> ORGANISM: Homo sapiens

<400> SEQUENCE: 90

Leu Lys Arg Pro Lys Asp
1               5

<210> SEQ ID NO 91
<211> LENGTH: 6
<212> TYPE: PRT
<213> ORGANISM: Homo sapiens

<400> SEQUENCE: 91

Met Lys Arg Leu Lys Val
1               5

<210> SEQ ID NO 92
<211> LENGTH: 6
<212> TYPE: PRT
<213> ORGANISM: Homo sapiens

<400> SEQUENCE: 92

Leu Lys Arg Pro Lys Asp
1               5

<210> SEQ ID NO 93
<211> LENGTH: 6
<212> TYPE: PRT
<213> ORGANISM: Homo sapiens
```

<400> SEQUENCE: 93

Gln Arg Lys Ser Lys Pro
1               5

<210> SEQ ID NO 94
<211> LENGTH: 6
<212> TYPE: PRT
<213> ORGANISM: Homo sapiens

<400> SEQUENCE: 94

Gln Arg Lys Ser Lys Pro
1               5

<210> SEQ ID NO 95
<211> LENGTH: 8
<212> TYPE: PRT
<213> ORGANISM: Homo sapiens

<400> SEQUENCE: 95

Leu Lys Arg Lys Met Phe Lys Met
1               5

<210> SEQ ID NO 96
<211> LENGTH: 6
<212> TYPE: PRT
<213> ORGANISM: Homo sapiens

<400> SEQUENCE: 96

Leu Lys Lys Leu Lys Thr
1               5

<210> SEQ ID NO 97
<211> LENGTH: 6
<212> TYPE: PRT
<213> ORGANISM: Homo sapiens

<400> SEQUENCE: 97

Val Lys Lys Glu Lys Leu
1               5

<210> SEQ ID NO 98
<211> LENGTH: 6
<212> TYPE: PRT
<213> ORGANISM: Homo sapiens

<400> SEQUENCE: 98

Leu Lys Lys Leu Lys Thr
1               5

<210> SEQ ID NO 99
<211> LENGTH: 6
<212> TYPE: PRT
<213> ORGANISM: Homo sapiens

<400> SEQUENCE: 99

Val Lys Lys Glu Lys Leu
1               5

<210> SEQ ID NO 100
<211> LENGTH: 6
<212> TYPE: PRT
<213> ORGANISM: Homo sapiens

<400> SEQUENCE: 100

Glu Lys Arg Glu Arg Thr
1               5

<210> SEQ ID NO 101
<211> LENGTH: 6
<212> TYPE: PRT
<213> ORGANISM: Homo sapiens

<400> SEQUENCE: 101

Glu Lys Arg Glu Arg Thr
1               5

<210> SEQ ID NO 102
<211> LENGTH: 6
<212> TYPE: PRT
<213> ORGANISM: Homo sapiens

<400> SEQUENCE: 102

Leu Lys Arg Val Arg Glu
1               5

<210> SEQ ID NO 103
<211> LENGTH: 6
<212> TYPE: PRT
<213> ORGANISM: Homo sapiens

<400> SEQUENCE: 103

Val Arg Arg Gly Arg Ile
1               5

<210> SEQ ID NO 104
<211> LENGTH: 6
<212> TYPE: PRT
<213> ORGANISM: Homo sapiens

<400> SEQUENCE: 104

Leu Lys Arg Val Arg Glu
1               5

<210> SEQ ID NO 105
<211> LENGTH: 6
<212> TYPE: PRT
<213> ORGANISM: Homo sapiens

<400> SEQUENCE: 105

Val Arg Arg Gly Arg Ile
1               5

<210> SEQ ID NO 106
<211> LENGTH: 6
<212> TYPE: PRT
<213> ORGANISM: Homo sapiens

<400> SEQUENCE: 106

Leu Lys Lys Pro Arg Lys
1               5

<210> SEQ ID NO 107
<211> LENGTH: 6
<212> TYPE: PRT
<213> ORGANISM: Homo sapiens

<400> SEQUENCE: 107

Asn Arg Arg Thr Lys Trp
1               5

<210> SEQ ID NO 108
<211> LENGTH: 6
<212> TYPE: PRT
<213> ORGANISM: Homo sapiens

<400> SEQUENCE: 108

Leu Lys Lys Pro Arg Lys
1               5

<210> SEQ ID NO 109
<211> LENGTH: 6
<212> TYPE: PRT
<213> ORGANISM: Homo sapiens

<400> SEQUENCE: 109

Asn Arg Arg Thr Lys Trp
1               5

<210> SEQ ID NO 110
<211> LENGTH: 8
<212> TYPE: PRT
<213> ORGANISM: Homo sapiens

<400> SEQUENCE: 110

Ser Arg Lys Lys Arg Glu Arg Asp
1               5

<210> SEQ ID NO 111
<211> LENGTH: 8
<212> TYPE: PRT
<213> ORGANISM: Homo sapiens

<400> SEQUENCE: 111

Gly Lys Arg Lys Ala Gly Lys Lys
1               5

<210> SEQ ID NO 112
<211> LENGTH: 6
<212> TYPE: PRT
<213> ORGANISM: Homo sapiens

<400> SEQUENCE: 112

Met Arg Lys Val Lys Phe
1               5

<210> SEQ ID NO 113
<211> LENGTH: 6
<212> TYPE: PRT
<213> ORGANISM: Homo sapiens

<400> SEQUENCE: 113

Ile Lys Arg Gln Lys Gln
1               5

<210> SEQ ID NO 114
<211> LENGTH: 6
<212> TYPE: PRT
<213> ORGANISM: Homo sapiens

<400> SEQUENCE: 114

Ala Arg Arg Lys Arg Met
1               5

```
<210> SEQ ID NO 115
<211> LENGTH: 6
<212> TYPE: PRT
<213> ORGANISM: Homo sapiens

<400> SEQUENCE: 115

Ser Arg Lys Lys Arg Glu
1               5

<210> SEQ ID NO 116
<211> LENGTH: 6
<212> TYPE: PRT
<213> ORGANISM: Homo sapiens

<400> SEQUENCE: 116

Lys Lys Lys Leu Lys Ile
1               5

<210> SEQ ID NO 117
<211> LENGTH: 6
<212> TYPE: PRT
<213> ORGANISM: Homo sapiens

<400> SEQUENCE: 117

Ala Arg Arg Ser Arg Ser
1               5

<210> SEQ ID NO 118
<211> LENGTH: 6
<212> TYPE: PRT
<213> ORGANISM: Homo sapiens

<400> SEQUENCE: 118

Thr Arg Lys Arg Lys Arg
1               5

<210> SEQ ID NO 119
<211> LENGTH: 6
<212> TYPE: PRT
<213> ORGANISM: Homo sapiens

<400> SEQUENCE: 119

Val Lys Lys Ala Lys Thr
1               5

<210> SEQ ID NO 120
<211> LENGTH: 6
<212> TYPE: PRT
<213> ORGANISM: Homo sapiens

<400> SEQUENCE: 120

Gly Lys Lys Asp Arg Arg
1               5

<210> SEQ ID NO 121
<211> LENGTH: 6
<212> TYPE: PRT
<213> ORGANISM: Homo sapiens

<400> SEQUENCE: 121

Met Arg Lys Val Lys Phe
1               5

<210> SEQ ID NO 122
<211> LENGTH: 6
```

```
<212> TYPE: PRT
<213> ORGANISM: Homo sapiens

<400> SEQUENCE: 122

Ile Lys Arg Gln Lys Gln
1               5

<210> SEQ ID NO 123
<211> LENGTH: 6
<212> TYPE: PRT
<213> ORGANISM: Homo sapiens

<400> SEQUENCE: 123

Ala Arg Arg Lys Arg Met
1               5

<210> SEQ ID NO 124
<211> LENGTH: 6
<212> TYPE: PRT
<213> ORGANISM: Homo sapiens

<400> SEQUENCE: 124

Ser Arg Lys Lys Arg Glu
1               5

<210> SEQ ID NO 125
<211> LENGTH: 6
<212> TYPE: PRT
<213> ORGANISM: Homo sapiens

<400> SEQUENCE: 125

Lys Lys Lys Leu Lys Ile
1               5

<210> SEQ ID NO 126
<211> LENGTH: 6
<212> TYPE: PRT
<213> ORGANISM: Homo sapiens

<400> SEQUENCE: 126

Ala Arg Arg Ser Arg Ser
1               5

<210> SEQ ID NO 127
<211> LENGTH: 6
<212> TYPE: PRT
<213> ORGANISM: Homo sapiens

<400> SEQUENCE: 127

Thr Arg Lys Arg Lys Arg
1               5

<210> SEQ ID NO 128
<211> LENGTH: 6
<212> TYPE: PRT
<213> ORGANISM: Homo sapiens

<400> SEQUENCE: 128

Val Lys Lys Ala Lys Thr
1               5

<210> SEQ ID NO 129
<211> LENGTH: 6
<212> TYPE: PRT
<213> ORGANISM: Homo sapiens
```

```
<400> SEQUENCE: 129

Gly Lys Lys Asp Arg Arg
1               5

<210> SEQ ID NO 130
<211> LENGTH: 6
<212> TYPE: PRT
<213> ORGANISM: Homo sapiens

<400> SEQUENCE: 130

Arg Arg Arg Pro Lys Thr
1               5

<210> SEQ ID NO 131
<211> LENGTH: 6
<212> TYPE: PRT
<213> ORGANISM: Homo sapiens

<400> SEQUENCE: 131

Glu Arg Lys Arg Lys Ala
1               5

<210> SEQ ID NO 132
<211> LENGTH: 6
<212> TYPE: PRT
<213> ORGANISM: Homo sapiens

<400> SEQUENCE: 132

Arg Arg Arg Pro Lys Thr
1               5

<210> SEQ ID NO 133
<211> LENGTH: 6
<212> TYPE: PRT
<213> ORGANISM: Homo sapiens

<400> SEQUENCE: 133

Glu Arg Lys Arg Lys Ala
1               5

<210> SEQ ID NO 134
<211> LENGTH: 6
<212> TYPE: PRT
<213> ORGANISM: Homo sapiens

<400> SEQUENCE: 134

Pro Lys Lys Ser Lys Ser
1               5

<210> SEQ ID NO 135
<211> LENGTH: 6
<212> TYPE: PRT
<213> ORGANISM: Homo sapiens

<400> SEQUENCE: 135

Pro Lys Lys Ser Lys Ser
1               5

<210> SEQ ID NO 136
<211> LENGTH: 6
<212> TYPE: PRT
<213> ORGANISM: Homo sapiens

<400> SEQUENCE: 136
```

```
Glu Lys Lys Pro Arg Arg
1               5

<210> SEQ ID NO 137
<211> LENGTH: 6
<212> TYPE: PRT
<213> ORGANISM: Homo sapiens

<400> SEQUENCE: 137

Glu Lys Lys Pro Arg Arg
1               5

<210> SEQ ID NO 138
<211> LENGTH: 6
<212> TYPE: PRT
<213> ORGANISM: Homo sapiens

<400> SEQUENCE: 138

Glu Lys Lys Gly Arg Lys
1               5

<210> SEQ ID NO 139
<211> LENGTH: 6
<212> TYPE: PRT
<213> ORGANISM: Homo sapiens

<400> SEQUENCE: 139

Glu Arg Lys Phe Lys Ala
1               5

<210> SEQ ID NO 140
<211> LENGTH: 6
<212> TYPE: PRT
<213> ORGANISM: Homo sapiens

<400> SEQUENCE: 140

Val Lys Lys Asn Lys Gln
1               5

<210> SEQ ID NO 141
<211> LENGTH: 6
<212> TYPE: PRT
<213> ORGANISM: Homo sapiens

<400> SEQUENCE: 141

Glu Lys Lys Gly Arg Lys
1               5

<210> SEQ ID NO 142
<211> LENGTH: 6
<212> TYPE: PRT
<213> ORGANISM: Homo sapiens

<400> SEQUENCE: 142

Glu Arg Lys Phe Lys Ala
1               5

<210> SEQ ID NO 143
<211> LENGTH: 6
<212> TYPE: PRT
<213> ORGANISM: Homo sapiens

<400> SEQUENCE: 143

Val Lys Lys Asn Lys Gln
```

```
1               5

<210> SEQ ID NO 144
<211> LENGTH: 6
<212> TYPE: PRT
<213> ORGANISM: Homo sapiens

<400> SEQUENCE: 144

Val Arg Arg Asp Arg Val
1               5

<210> SEQ ID NO 145
<211> LENGTH: 6
<212> TYPE: PRT
<213> ORGANISM: Homo sapiens

<400> SEQUENCE: 145

Val Arg Arg Asp Arg Val
1               5

<210> SEQ ID NO 146
<211> LENGTH: 6
<212> TYPE: PRT
<213> ORGANISM: Homo sapiens

<400> SEQUENCE: 146

Pro Arg Lys Val Lys Ser
1               5

<210> SEQ ID NO 147
<211> LENGTH: 6
<212> TYPE: PRT
<213> ORGANISM: Homo sapiens

<400> SEQUENCE: 147

Val Arg Lys Asp Lys Leu
1               5

<210> SEQ ID NO 148
<211> LENGTH: 6
<212> TYPE: PRT
<213> ORGANISM: Homo sapiens

<400> SEQUENCE: 148

Pro Arg Lys Val Lys Ser
1               5

<210> SEQ ID NO 149
<211> LENGTH: 6
<212> TYPE: PRT
<213> ORGANISM: Homo sapiens

<400> SEQUENCE: 149

Val Arg Lys Asp Lys Leu
1               5

<210> SEQ ID NO 150
<211> LENGTH: 8
<212> TYPE: PRT
<213> ORGANISM: Homo sapiens

<400> SEQUENCE: 150

Gly Arg Lys Lys Cys Glu Arg Tyr
1               5
```

<210> SEQ ID NO 151
<211> LENGTH: 6
<212> TYPE: PRT
<213> ORGANISM: Homo sapiens

<400> SEQUENCE: 151

Val Lys Lys Asn Arg Tyr
1               5

<210> SEQ ID NO 152
<211> LENGTH: 6
<212> TYPE: PRT
<213> ORGANISM: Homo sapiens

<400> SEQUENCE: 152

Val Lys Lys Asn Arg Tyr
1               5

<210> SEQ ID NO 153
<211> LENGTH: 6
<212> TYPE: PRT
<213> ORGANISM: Homo sapiens

<400> SEQUENCE: 153

Val Arg Lys Ile Arg Phe
1               5

<210> SEQ ID NO 154
<211> LENGTH: 6
<212> TYPE: PRT
<213> ORGANISM: Homo sapiens

<400> SEQUENCE: 154

Val Arg Lys Ile Arg Phe
1               5

<210> SEQ ID NO 155
<211> LENGTH: 8
<212> TYPE: PRT
<213> ORGANISM: Homo sapiens

<400> SEQUENCE: 155

Ser Arg Lys Arg Gln Thr Arg Arg
1               5

<210> SEQ ID NO 156
<211> LENGTH: 6
<212> TYPE: PRT
<213> ORGANISM: Homo sapiens

<400> SEQUENCE: 156

Thr Arg Arg Arg Arg Asn
1               5

<210> SEQ ID NO 157
<211> LENGTH: 6
<212> TYPE: PRT
<213> ORGANISM: Homo sapiens

<400> SEQUENCE: 157

Thr Arg Arg Arg Arg Asn
1               5

<210> SEQ ID NO 158

```
<211> LENGTH: 8
<212> TYPE: PRT
<213> ORGANISM: Homo sapiens

<400> SEQUENCE: 158

Ala Arg Arg Lys Gly Arg Arg Gly
1               5

<210> SEQ ID NO 159
<211> LENGTH: 8
<212> TYPE: PRT
<213> ORGANISM: Homo sapiens

<400> SEQUENCE: 159

Glu Lys Lys Arg His Ser Lys Val
1               5

<210> SEQ ID NO 160
<211> LENGTH: 6
<212> TYPE: PRT
<213> ORGANISM: Homo sapiens

<400> SEQUENCE: 160

Arg Arg Lys Gly Arg Arg
1               5

<210> SEQ ID NO 161
<211> LENGTH: 6
<212> TYPE: PRT
<213> ORGANISM: Homo sapiens

<400> SEQUENCE: 161

Arg Arg Lys Gly Arg Arg
1               5

<210> SEQ ID NO 162
<211> LENGTH: 8
<212> TYPE: PRT
<213> ORGANISM: Homo sapiens

<400> SEQUENCE: 162

Pro Lys Arg Lys Asn Lys Lys Ser
1               5

<210> SEQ ID NO 163
<211> LENGTH: 6
<212> TYPE: PRT
<213> ORGANISM: Homo sapiens

<400> SEQUENCE: 163

Asp Lys Lys Leu Arg Glu
1               5

<210> SEQ ID NO 164
<211> LENGTH: 6
<212> TYPE: PRT
<213> ORGANISM: Homo sapiens

<400> SEQUENCE: 164

Lys Arg Lys Asn Lys Lys
1               5

<210> SEQ ID NO 165
<211> LENGTH: 6
<212> TYPE: PRT
```

<213> ORGANISM: Homo sapiens

<400> SEQUENCE: 165

Val Lys Arg Leu Lys Ser
1               5

<210> SEQ ID NO 166
<211> LENGTH: 6
<212> TYPE: PRT
<213> ORGANISM: Homo sapiens

<400> SEQUENCE: 166

Asp Lys Lys Leu Arg Glu
1               5

<210> SEQ ID NO 167
<211> LENGTH: 6
<212> TYPE: PRT
<213> ORGANISM: Homo sapiens

<400> SEQUENCE: 167

Lys Arg Lys Asn Lys Lys
1               5

<210> SEQ ID NO 168
<211> LENGTH: 6
<212> TYPE: PRT
<213> ORGANISM: Homo sapiens

<400> SEQUENCE: 168

Val Lys Arg Leu Lys Ser
1               5

<210> SEQ ID NO 169
<211> LENGTH: 8
<212> TYPE: PRT
<213> ORGANISM: Homo sapiens

<400> SEQUENCE: 169

Ala Lys Lys Lys Thr Lys Lys Arg
1               5

<210> SEQ ID NO 170
<211> LENGTH: 6
<212> TYPE: PRT
<213> ORGANISM: Homo sapiens

<400> SEQUENCE: 170

Lys Lys Lys Thr Lys Lys
1               5

<210> SEQ ID NO 171
<211> LENGTH: 6
<212> TYPE: PRT
<213> ORGANISM: Homo sapiens

<400> SEQUENCE: 171

Glu Arg Arg Arg Arg Glu
1               5

<210> SEQ ID NO 172
<211> LENGTH: 6
<212> TYPE: PRT
<213> ORGANISM: Homo sapiens

```
<400> SEQUENCE: 172

Arg Lys Arg Gln Arg Glu
1               5

<210> SEQ ID NO 173
<211> LENGTH: 6
<212> TYPE: PRT
<213> ORGANISM: Homo sapiens

<400> SEQUENCE: 173

Arg Arg Lys Trp Lys Glu
1               5

<210> SEQ ID NO 174
<211> LENGTH: 6
<212> TYPE: PRT
<213> ORGANISM: Homo sapiens

<400> SEQUENCE: 174

Glu Lys Arg Lys Arg Lys
1               5

<210> SEQ ID NO 175
<211> LENGTH: 6
<212> TYPE: PRT
<213> ORGANISM: Homo sapiens

<400> SEQUENCE: 175

Asp Lys Arg Glu Lys Ala
1               5

<210> SEQ ID NO 176
<211> LENGTH: 6
<212> TYPE: PRT
<213> ORGANISM: Homo sapiens

<400> SEQUENCE: 176

Arg Arg Arg Gln Lys Glu
1               5

<210> SEQ ID NO 177
<211> LENGTH: 6
<212> TYPE: PRT
<213> ORGANISM: Homo sapiens

<400> SEQUENCE: 177

Met Lys Lys Glu Lys Asp
1               5

<210> SEQ ID NO 178
<211> LENGTH: 6
<212> TYPE: PRT
<213> ORGANISM: Homo sapiens

<400> SEQUENCE: 178

Val Lys Arg Asp Arg Ile
1               5

<210> SEQ ID NO 179
<211> LENGTH: 9
<212> TYPE: PRT
<213> ORGANISM: Homo sapiens

<400> SEQUENCE: 179
```

Ala Lys Lys Lys Thr Lys Lys Arg Asp
1               5

<210> SEQ ID NO 180
<211> LENGTH: 6
<212> TYPE: PRT
<213> ORGANISM: Homo sapiens

<400> SEQUENCE: 180

Lys Lys Lys Thr Lys Lys
1               5

<210> SEQ ID NO 181
<211> LENGTH: 6
<212> TYPE: PRT
<213> ORGANISM: Homo sapiens

<400> SEQUENCE: 181

Glu Arg Arg Arg Arg Glu
1               5

<210> SEQ ID NO 182
<211> LENGTH: 6
<212> TYPE: PRT
<213> ORGANISM: Homo sapiens

<400> SEQUENCE: 182

Arg Lys Arg Gln Arg Glu
1               5

<210> SEQ ID NO 183
<211> LENGTH: 6
<212> TYPE: PRT
<213> ORGANISM: Homo sapiens

<400> SEQUENCE: 183

Arg Arg Lys Trp Lys Glu
1               5

<210> SEQ ID NO 184
<211> LENGTH: 6
<212> TYPE: PRT
<213> ORGANISM: Homo sapiens

<400> SEQUENCE: 184

Glu Lys Arg Lys Arg Lys
1               5

<210> SEQ ID NO 185
<211> LENGTH: 6
<212> TYPE: PRT
<213> ORGANISM: Homo sapiens

<400> SEQUENCE: 185

Asp Lys Arg Glu Lys Ala
1               5

<210> SEQ ID NO 186
<211> LENGTH: 6
<212> TYPE: PRT
<213> ORGANISM: Homo sapiens

<400> SEQUENCE: 186

Arg Arg Arg Gln Lys Glu
1               5

```
<210> SEQ ID NO 187
<211> LENGTH: 6
<212> TYPE: PRT
<213> ORGANISM: Homo sapiens

<400> SEQUENCE: 187

Met Lys Lys Glu Lys Asp
1               5

<210> SEQ ID NO 188
<211> LENGTH: 6
<212> TYPE: PRT
<213> ORGANISM: Homo sapiens

<400> SEQUENCE: 188

Val Lys Arg Asp Arg Ile
1               5

<210> SEQ ID NO 189
<211> LENGTH: 6
<212> TYPE: PRT
<213> ORGANISM: Homo sapiens

<400> SEQUENCE: 189

Ala Arg Arg Thr Arg Ser
1               5

<210> SEQ ID NO 190
<211> LENGTH: 6
<212> TYPE: PRT
<213> ORGANISM: Homo sapiens

<400> SEQUENCE: 190

Ala Arg Arg Thr Arg Ser
1               5

<210> SEQ ID NO 191
<211> LENGTH: 6
<212> TYPE: PRT
<213> ORGANISM: Homo sapiens

<400> SEQUENCE: 191

Lys Arg Lys Ile Arg Asp
1               5

<210> SEQ ID NO 192
<211> LENGTH: 6
<212> TYPE: PRT
<213> ORGANISM: Homo sapiens

<400> SEQUENCE: 192

Lys Arg Lys Ile Arg Asp
1               5

<210> SEQ ID NO 193
<211> LENGTH: 6
<212> TYPE: PRT
<213> ORGANISM: Homo sapiens

<400> SEQUENCE: 193

Glu Lys Lys Ala Arg Lys
1               5
```

```
<210> SEQ ID NO 194
<211> LENGTH: 6
<212> TYPE: PRT
<213> ORGANISM: Homo sapiens

<400> SEQUENCE: 194

Ile Arg Lys Ser Lys Asn
1               5

<210> SEQ ID NO 195
<211> LENGTH: 6
<212> TYPE: PRT
<213> ORGANISM: Homo sapiens

<400> SEQUENCE: 195

Glu Lys Lys Ala Arg Lys
1               5

<210> SEQ ID NO 196
<211> LENGTH: 6
<212> TYPE: PRT
<213> ORGANISM: Homo sapiens

<400> SEQUENCE: 196

Ile Arg Lys Ser Lys Asn
1               5

<210> SEQ ID NO 197
<211> LENGTH: 6
<212> TYPE: PRT
<213> ORGANISM: Homo sapiens

<400> SEQUENCE: 197

Ala Arg Lys Glu Arg Glu
1               5

<210> SEQ ID NO 198
<211> LENGTH: 6
<212> TYPE: PRT
<213> ORGANISM: Homo sapiens

<400> SEQUENCE: 198

Ala Arg Lys Glu Arg Glu
1               5

<210> SEQ ID NO 199
<211> LENGTH: 6
<212> TYPE: PRT
<213> ORGANISM: Homo sapiens

<400> SEQUENCE: 199

Leu Lys Arg Asp Arg Phe
1               5

<210> SEQ ID NO 200
<211> LENGTH: 6
<212> TYPE: PRT
<213> ORGANISM: Homo sapiens

<400> SEQUENCE: 200

Leu Lys Arg Asp Arg Phe
1               5

<210> SEQ ID NO 201
<211> LENGTH: 6
```

<212> TYPE: PRT
<213> ORGANISM: Homo sapiens

<400> SEQUENCE: 201

His Arg Arg Pro Arg Glu
1               5

<210> SEQ ID NO 202
<211> LENGTH: 6
<212> TYPE: PRT
<213> ORGANISM: Homo sapiens

<400> SEQUENCE: 202

Pro Arg Lys Lys Arg Pro
1               5

<210> SEQ ID NO 203
<211> LENGTH: 6
<212> TYPE: PRT
<213> ORGANISM: Homo sapiens

<400> SEQUENCE: 203

Asp Arg Lys Gln Lys Val
1               5

<210> SEQ ID NO 204
<211> LENGTH: 6
<212> TYPE: PRT
<213> ORGANISM: Homo sapiens

<400> SEQUENCE: 204

His Arg Arg Pro Arg Glu
1               5

<210> SEQ ID NO 205
<211> LENGTH: 6
<212> TYPE: PRT
<213> ORGANISM: Homo sapiens

<400> SEQUENCE: 205

Pro Arg Lys Lys Arg Pro
1               5

<210> SEQ ID NO 206
<211> LENGTH: 6
<212> TYPE: PRT
<213> ORGANISM: Homo sapiens

<400> SEQUENCE: 206

Asp Arg Lys Gln Lys Val
1               5

<210> SEQ ID NO 207
<211> LENGTH: 8
<212> TYPE: PRT
<213> ORGANISM: Homo sapiens

<400> SEQUENCE: 207

Ser Arg Arg Lys Arg Leu Arg His
1               5

<210> SEQ ID NO 208
<211> LENGTH: 6
<212> TYPE: PRT
<213> ORGANISM: Homo sapiens

```
<400> SEQUENCE: 208

Ser Arg Arg Lys Arg Leu
1               5

<210> SEQ ID NO 209
<211> LENGTH: 6
<212> TYPE: PRT
<213> ORGANISM: Homo sapiens

<400> SEQUENCE: 209

Ser Arg Arg Lys Arg Leu
1               5

<210> SEQ ID NO 210
<211> LENGTH: 6
<212> TYPE: PRT
<213> ORGANISM: Homo sapiens

<400> SEQUENCE: 210

Gly Lys Lys Val Arg Val
1               5

<210> SEQ ID NO 211
<211> LENGTH: 6
<212> TYPE: PRT
<213> ORGANISM: Homo sapiens

<400> SEQUENCE: 211

Gly Lys Lys Val Arg Val
1               5

<210> SEQ ID NO 212
<211> LENGTH: 6
<212> TYPE: PRT
<213> ORGANISM: Homo sapiens

<400> SEQUENCE: 212

Ala Arg Lys Arg Arg Leu
1               5

<210> SEQ ID NO 213
<211> LENGTH: 6
<212> TYPE: PRT
<213> ORGANISM: Homo sapiens

<400> SEQUENCE: 213

Ala Arg Lys Arg Arg Leu
1               5

<210> SEQ ID NO 214
<211> LENGTH: 6
<212> TYPE: PRT
<213> ORGANISM: Homo sapiens

<400> SEQUENCE: 214

Gly Lys Arg Met Arg Thr
1               5

<210> SEQ ID NO 215
<211> LENGTH: 6
<212> TYPE: PRT
<213> ORGANISM: Homo sapiens

<400> SEQUENCE: 215
```

Asn Arg Arg Val Lys His
1               5

<210> SEQ ID NO 216
<211> LENGTH: 6
<212> TYPE: PRT
<213> ORGANISM: Homo sapiens

<400> SEQUENCE: 216

Gly Lys Arg Met Arg Thr
1               5

<210> SEQ ID NO 217
<211> LENGTH: 6
<212> TYPE: PRT
<213> ORGANISM: Homo sapiens

<400> SEQUENCE: 217

Asn Arg Arg Val Lys His
1               5

<210> SEQ ID NO 218
<211> LENGTH: 6
<212> TYPE: PRT
<213> ORGANISM: Homo sapiens

<400> SEQUENCE: 218

Ala Arg Arg Met Lys Glu
1               5

<210> SEQ ID NO 219
<211> LENGTH: 6
<212> TYPE: PRT
<213> ORGANISM: Homo sapiens

<400> SEQUENCE: 219

His Arg Lys Lys Arg Leu
1               5

<210> SEQ ID NO 220
<211> LENGTH: 6
<212> TYPE: PRT
<213> ORGANISM: Homo sapiens

<400> SEQUENCE: 220

Ala Arg Arg Met Lys Glu
1               5

<210> SEQ ID NO 221
<211> LENGTH: 6
<212> TYPE: PRT
<213> ORGANISM: Homo sapiens

<400> SEQUENCE: 221

His Arg Lys Lys Arg Leu
1               5

<210> SEQ ID NO 222
<211> LENGTH: 6
<212> TYPE: PRT
<213> ORGANISM: Homo sapiens

<400> SEQUENCE: 222

Ser Lys Lys Glu Lys Val

```
<210> SEQ ID NO 223
<211> LENGTH: 6
<212> TYPE: PRT
<213> ORGANISM: Homo sapiens

<400> SEQUENCE: 223

Ser Lys Lys Glu Lys Val
1               5

<210> SEQ ID NO 224
<211> LENGTH: 6
<212> TYPE: PRT
<213> ORGANISM: Homo sapiens

<400> SEQUENCE: 224

Ser Lys Arg Cys Lys Lys
1               5

<210> SEQ ID NO 225
<211> LENGTH: 6
<212> TYPE: PRT
<213> ORGANISM: Homo sapiens

<400> SEQUENCE: 225

Ser Lys Arg Cys Lys Lys
1               5

<210> SEQ ID NO 226
<211> LENGTH: 6
<212> TYPE: PRT
<213> ORGANISM: Homo sapiens

<400> SEQUENCE: 226

Leu Lys Lys Tyr Lys Glu
1               5

<210> SEQ ID NO 227
<211> LENGTH: 6
<212> TYPE: PRT
<213> ORGANISM: Homo sapiens

<400> SEQUENCE: 227

Ile Lys Arg Leu Lys Glu
1               5

<210> SEQ ID NO 228
<211> LENGTH: 9
<212> TYPE: PRT
<213> ORGANISM: Homo sapiens

<400> SEQUENCE: 228

Leu Lys Lys Tyr Lys Glu Lys Arg Thr
1               5

<210> SEQ ID NO 229
<211> LENGTH: 6
<212> TYPE: PRT
<213> ORGANISM: Homo sapiens

<400> SEQUENCE: 229

Leu Lys Lys Tyr Lys Glu
1               5
```

```
<210> SEQ ID NO 230
<211> LENGTH: 6
<212> TYPE: PRT
<213> ORGANISM: Homo sapiens

<400> SEQUENCE: 230

Ile Lys Arg Leu Lys Glu
1               5

<210> SEQ ID NO 231
<211> LENGTH: 6
<212> TYPE: PRT
<213> ORGANISM: Homo sapiens

<400> SEQUENCE: 231

Ala Arg Lys Ile Arg Thr
1               5

<210> SEQ ID NO 232
<211> LENGTH: 6
<212> TYPE: PRT
<213> ORGANISM: Homo sapiens

<400> SEQUENCE: 232

Asp Arg Arg Val Arg Ser
1               5

<210> SEQ ID NO 233
<211> LENGTH: 6
<212> TYPE: PRT
<213> ORGANISM: Homo sapiens

<400> SEQUENCE: 233

Pro Arg Lys Cys Arg Gln
1               5

<210> SEQ ID NO 234
<211> LENGTH: 6
<212> TYPE: PRT
<213> ORGANISM: Homo sapiens

<400> SEQUENCE: 234

Ala Arg Lys Ile Arg Thr
1               5

<210> SEQ ID NO 235
<211> LENGTH: 6
<212> TYPE: PRT
<213> ORGANISM: Homo sapiens

<400> SEQUENCE: 235

Asp Arg Arg Val Arg Ser
1               5

<210> SEQ ID NO 236
<211> LENGTH: 6
<212> TYPE: PRT
<213> ORGANISM: Homo sapiens

<400> SEQUENCE: 236

Pro Arg Lys Cys Arg Gln
1               5

<210> SEQ ID NO 237
```

```
<211> LENGTH: 6
<212> TYPE: PRT
<213> ORGANISM: Homo sapiens

<400> SEQUENCE: 237

His Arg Arg His Arg His
1               5

<210> SEQ ID NO 238
<211> LENGTH: 6
<212> TYPE: PRT
<213> ORGANISM: Homo sapiens

<400> SEQUENCE: 238

Arg Lys Arg Asp Arg Glu
1               5

<210> SEQ ID NO 239
<211> LENGTH: 6
<212> TYPE: PRT
<213> ORGANISM: Homo sapiens

<400> SEQUENCE: 239

Ser Lys Lys Lys Lys Leu
1               5

<210> SEQ ID NO 240
<211> LENGTH: 6
<212> TYPE: PRT
<213> ORGANISM: Homo sapiens

<400> SEQUENCE: 240

His Arg Arg His Arg His
1               5

<210> SEQ ID NO 241
<211> LENGTH: 6
<212> TYPE: PRT
<213> ORGANISM: Homo sapiens

<400> SEQUENCE: 241

Arg Lys Arg Asp Arg Glu
1               5

<210> SEQ ID NO 242
<211> LENGTH: 6
<212> TYPE: PRT
<213> ORGANISM: Homo sapiens

<400> SEQUENCE: 242

Ser Lys Lys Lys Lys Leu
1               5

<210> SEQ ID NO 243
<211> LENGTH: 8
<212> TYPE: PRT
<213> ORGANISM: Homo sapiens

<400> SEQUENCE: 243

Leu Lys Lys Lys Glu Glu Arg Leu
1               5

<210> SEQ ID NO 244
<211> LENGTH: 6
<212> TYPE: PRT
```

<213> ORGANISM: Homo sapiens

<400> SEQUENCE: 244

Glu Lys Lys Gln Arg Arg
1               5

<210> SEQ ID NO 245
<211> LENGTH: 6
<212> TYPE: PRT
<213> ORGANISM: Homo sapiens

<400> SEQUENCE: 245

Ala Lys Lys Met Arg Pro
1               5

<210> SEQ ID NO 246
<211> LENGTH: 6
<212> TYPE: PRT
<213> ORGANISM: Homo sapiens

<400> SEQUENCE: 246

Glu Lys Lys Gln Arg Arg
1               5

<210> SEQ ID NO 247
<211> LENGTH: 6
<212> TYPE: PRT
<213> ORGANISM: Homo sapiens

<400> SEQUENCE: 247

Ala Lys Lys Met Arg Pro
1               5

<210> SEQ ID NO 248
<211> LENGTH: 6
<212> TYPE: PRT
<213> ORGANISM: Homo sapiens

<400> SEQUENCE: 248

Met Arg Lys Gly Lys Gln
1               5

<210> SEQ ID NO 249
<211> LENGTH: 6
<212> TYPE: PRT
<213> ORGANISM: Homo sapiens

<400> SEQUENCE: 249

Met Arg Lys Gly Lys Gln
1               5

<210> SEQ ID NO 250
<211> LENGTH: 8
<212> TYPE: PRT
<213> ORGANISM: Homo sapiens

<400> SEQUENCE: 250

Glu Arg Arg Arg Arg Pro Arg Asp
1               5

<210> SEQ ID NO 251
<211> LENGTH: 6
<212> TYPE: PRT
<213> ORGANISM: Homo sapiens

```
<400> SEQUENCE: 251

Ser Arg Lys Trp Arg Pro
1               5

<210> SEQ ID NO 252
<211> LENGTH: 6
<212> TYPE: PRT
<213> ORGANISM: Homo sapiens

<400> SEQUENCE: 252

Glu Arg Arg Arg Arg Pro
1               5

<210> SEQ ID NO 253
<211> LENGTH: 6
<212> TYPE: PRT
<213> ORGANISM: Homo sapiens

<400> SEQUENCE: 253

Ser Arg Lys Trp Arg Pro
1               5

<210> SEQ ID NO 254
<211> LENGTH: 6
<212> TYPE: PRT
<213> ORGANISM: Homo sapiens

<400> SEQUENCE: 254

Glu Arg Arg Arg Arg Pro
1               5

<210> SEQ ID NO 255
<211> LENGTH: 8
<212> TYPE: PRT
<213> ORGANISM: Homo sapiens

<400> SEQUENCE: 255

Gly Lys Lys Lys Lys Arg Lys Arg
1               5

<210> SEQ ID NO 256
<211> LENGTH: 6
<212> TYPE: PRT
<213> ORGANISM: Homo sapiens

<400> SEQUENCE: 256

Ala Arg Lys Glu Arg Gln
1               5

<210> SEQ ID NO 257
<211> LENGTH: 6
<212> TYPE: PRT
<213> ORGANISM: Homo sapiens

<400> SEQUENCE: 257

Gly Lys Lys Lys Lys Arg
1               5

<210> SEQ ID NO 258
<211> LENGTH: 9
<212> TYPE: PRT
<213> ORGANISM: Homo sapiens

<400> SEQUENCE: 258
```

```
Gly Lys Lys Lys Arg Lys Arg Glu
1               5

<210> SEQ ID NO 259
<211> LENGTH: 6
<212> TYPE: PRT
<213> ORGANISM: Homo sapiens

<400> SEQUENCE: 259

Ala Arg Lys Glu Arg Gln
1               5

<210> SEQ ID NO 260
<211> LENGTH: 6
<212> TYPE: PRT
<213> ORGANISM: Homo sapiens

<400> SEQUENCE: 260

Gly Lys Lys Lys Lys Arg
1               5

<210> SEQ ID NO 261
<211> LENGTH: 6
<212> TYPE: PRT
<213> ORGANISM: Homo sapiens

<400> SEQUENCE: 261

Val Arg Arg Tyr Arg Glu
1               5

<210> SEQ ID NO 262
<211> LENGTH: 6
<212> TYPE: PRT
<213> ORGANISM: Homo sapiens

<400> SEQUENCE: 262

Val Arg Arg Tyr Arg Glu
1               5

<210> SEQ ID NO 263
<211> LENGTH: 6
<212> TYPE: PRT
<213> ORGANISM: Homo sapiens

<400> SEQUENCE: 263

Asn Lys Lys Glu Lys Met
1               5

<210> SEQ ID NO 264
<211> LENGTH: 6
<212> TYPE: PRT
<213> ORGANISM: Homo sapiens

<400> SEQUENCE: 264

Asn Lys Lys Glu Lys Met
1               5

<210> SEQ ID NO 265
<211> LENGTH: 6
<212> TYPE: PRT
<213> ORGANISM: Homo sapiens

<400> SEQUENCE: 265

Lys Lys Arg Glu Lys Glu
1               5
```

<210> SEQ ID NO 266
<211> LENGTH: 6
<212> TYPE: PRT
<213> ORGANISM: Homo sapiens

<400> SEQUENCE: 266

Lys Lys Lys Phe Lys Leu
1               5

<210> SEQ ID NO 267
<211> LENGTH: 6
<212> TYPE: PRT
<213> ORGANISM: Homo sapiens

<400> SEQUENCE: 267

Leu Lys Lys Leu Lys Lys
1               5

<210> SEQ ID NO 268
<211> LENGTH: 6
<212> TYPE: PRT
<213> ORGANISM: Homo sapiens

<400> SEQUENCE: 268

Arg Lys Lys Phe Lys Tyr
1               5

<210> SEQ ID NO 269
<211> LENGTH: 6
<212> TYPE: PRT
<213> ORGANISM: Homo sapiens

<400> SEQUENCE: 269

Lys Lys Arg Glu Lys Glu
1               5

<210> SEQ ID NO 270
<211> LENGTH: 6
<212> TYPE: PRT
<213> ORGANISM: Homo sapiens

<400> SEQUENCE: 270

Lys Lys Lys Phe Lys Leu
1               5

<210> SEQ ID NO 271
<211> LENGTH: 6
<212> TYPE: PRT
<213> ORGANISM: Homo sapiens

<400> SEQUENCE: 271

Leu Lys Lys Leu Lys Lys
1               5

<210> SEQ ID NO 272
<211> LENGTH: 6
<212> TYPE: PRT
<213> ORGANISM: Homo sapiens

<400> SEQUENCE: 272

Arg Lys Lys Phe Lys Tyr
1               5

```
<210> SEQ ID NO 273
<211> LENGTH: 6
<212> TYPE: PRT
<213> ORGANISM: Homo sapiens

<400> SEQUENCE: 273

Gly Lys Lys Gln Lys Thr
1               5

<210> SEQ ID NO 274
<211> LENGTH: 6
<212> TYPE: PRT
<213> ORGANISM: Homo sapiens

<400> SEQUENCE: 274

Gly Lys Lys Gln Lys Thr
1               5

<210> SEQ ID NO 275
<211> LENGTH: 8
<212> TYPE: PRT
<213> ORGANISM: Homo sapiens

<400> SEQUENCE: 275

Leu Arg Arg Arg Lys Gly Lys Arg
1               5

<210> SEQ ID NO 276
<211> LENGTH: 6
<212> TYPE: PRT
<213> ORGANISM: Homo sapiens

<400> SEQUENCE: 276

Leu Arg Arg Trp Arg Arg
1               5

<210> SEQ ID NO 277
<211> LENGTH: 6
<212> TYPE: PRT
<213> ORGANISM: Homo sapiens

<400> SEQUENCE: 277

Leu Arg Arg Arg Lys Gly
1               5

<210> SEQ ID NO 278
<211> LENGTH: 6
<212> TYPE: PRT
<213> ORGANISM: Homo sapiens

<400> SEQUENCE: 278

Leu Arg Arg Trp Arg Arg
1               5

<210> SEQ ID NO 279
<211> LENGTH: 6
<212> TYPE: PRT
<213> ORGANISM: Homo sapiens

<400> SEQUENCE: 279

Leu Arg Arg Arg Lys Gly
1               5

<210> SEQ ID NO 280
<211> LENGTH: 6
```

```
<212> TYPE: PRT
<213> ORGANISM: Homo sapiens

<400> SEQUENCE: 280

Asp Lys Lys Ala Lys Tyr
1               5

<210> SEQ ID NO 281
<211> LENGTH: 6
<212> TYPE: PRT
<213> ORGANISM: Homo sapiens

<400> SEQUENCE: 281

Gly Arg Arg Glu Lys Arg
1               5

<210> SEQ ID NO 282
<211> LENGTH: 6
<212> TYPE: PRT
<213> ORGANISM: Homo sapiens

<400> SEQUENCE: 282

Asp Lys Lys Ala Lys Tyr
1               5

<210> SEQ ID NO 283
<211> LENGTH: 6
<212> TYPE: PRT
<213> ORGANISM: Homo sapiens

<400> SEQUENCE: 283

Gly Arg Arg Glu Lys Arg
1               5

<210> SEQ ID NO 284
<211> LENGTH: 6
<212> TYPE: PRT
<213> ORGANISM: Homo sapiens

<400> SEQUENCE: 284

Ala Lys Arg Gln Arg Leu
1               5

<210> SEQ ID NO 285
<211> LENGTH: 6
<212> TYPE: PRT
<213> ORGANISM: Homo sapiens

<400> SEQUENCE: 285

Glu Lys Arg Ala Arg Ile
1               5

<210> SEQ ID NO 286
<211> LENGTH: 6
<212> TYPE: PRT
<213> ORGANISM: Homo sapiens

<400> SEQUENCE: 286

Arg Lys Lys Ala Lys Ile
1               5

<210> SEQ ID NO 287
<211> LENGTH: 6
<212> TYPE: PRT
<213> ORGANISM: Homo sapiens
```

```
<400> SEQUENCE: 287

Ala Lys Arg Gln Arg Leu
1               5

<210> SEQ ID NO 288
<211> LENGTH: 6
<212> TYPE: PRT
<213> ORGANISM: Homo sapiens

<400> SEQUENCE: 288

Glu Lys Arg Ala Arg Ile
1               5

<210> SEQ ID NO 289
<211> LENGTH: 6
<212> TYPE: PRT
<213> ORGANISM: Homo sapiens

<400> SEQUENCE: 289

Arg Lys Lys Ala Lys Ile
1               5

<210> SEQ ID NO 290
<211> LENGTH: 6
<212> TYPE: PRT
<213> ORGANISM: Homo sapiens

<400> SEQUENCE: 290

Val Arg Arg Ile Arg Asp
1               5

<210> SEQ ID NO 291
<211> LENGTH: 6
<212> TYPE: PRT
<213> ORGANISM: Homo sapiens

<400> SEQUENCE: 291

Val Arg Arg Ile Arg Asp
1               5

<210> SEQ ID NO 292
<211> LENGTH: 6
<212> TYPE: PRT
<213> ORGANISM: Homo sapiens

<400> SEQUENCE: 292

Leu Arg Lys Arg Arg Lys
1               5

<210> SEQ ID NO 293
<211> LENGTH: 6
<212> TYPE: PRT
<213> ORGANISM: Homo sapiens

<400> SEQUENCE: 293

Leu Arg Lys Arg Arg Lys
1               5

<210> SEQ ID NO 294
<211> LENGTH: 6
<212> TYPE: PRT
<213> ORGANISM: Homo sapiens

<400> SEQUENCE: 294
```

```
Asp Arg Arg Glu Arg Glu
1               5

<210> SEQ ID NO 295
<211> LENGTH: 6
<212> TYPE: PRT
<213> ORGANISM: Homo sapiens

<400> SEQUENCE: 295

Asp Arg Arg Glu Arg Glu
1               5

<210> SEQ ID NO 296
<211> LENGTH: 8
<212> TYPE: PRT
<213> ORGANISM: Homo sapiens

<400> SEQUENCE: 296

Lys Lys Lys Lys Ser Ser Arg Leu
1               5

<210> SEQ ID NO 297
<211> LENGTH: 6
<212> TYPE: PRT
<213> ORGANISM: Homo sapiens

<400> SEQUENCE: 297

Thr Lys Lys Lys Lys Ser
1               5

<210> SEQ ID NO 298
<211> LENGTH: 6
<212> TYPE: PRT
<213> ORGANISM: Homo sapiens

<400> SEQUENCE: 298

Gln Lys Arg Val Lys Glu
1               5

<210> SEQ ID NO 299
<211> LENGTH: 6
<212> TYPE: PRT
<213> ORGANISM: Homo sapiens

<400> SEQUENCE: 299

Gly Lys Arg Ser Arg Thr
1               5

<210> SEQ ID NO 300
<211> LENGTH: 6
<212> TYPE: PRT
<213> ORGANISM: Homo sapiens

<400> SEQUENCE: 300

Pro Lys Arg Lys Lys Ala
1               5

<210> SEQ ID NO 301
<211> LENGTH: 6
<212> TYPE: PRT
<213> ORGANISM: Homo sapiens

<400> SEQUENCE: 301

Gly Lys Arg Glu Lys Ser
```

```
1               5

<210> SEQ ID NO 302
<211> LENGTH: 6
<212> TYPE: PRT
<213> ORGANISM: Homo sapiens

<400> SEQUENCE: 302

His Lys Lys His Lys Lys
1               5

<210> SEQ ID NO 303
<211> LENGTH: 6
<212> TYPE: PRT
<213> ORGANISM: Homo sapiens

<400> SEQUENCE: 303

Lys Lys Lys Val Lys Asp
1               5

<210> SEQ ID NO 304
<211> LENGTH: 6
<212> TYPE: PRT
<213> ORGANISM: Homo sapiens

<400> SEQUENCE: 304

Thr Lys Lys Lys Lys Ser
1               5

<210> SEQ ID NO 305
<211> LENGTH: 6
<212> TYPE: PRT
<213> ORGANISM: Homo sapiens

<400> SEQUENCE: 305

Gln Lys Arg Val Lys Glu
1               5

<210> SEQ ID NO 306
<211> LENGTH: 6
<212> TYPE: PRT
<213> ORGANISM: Homo sapiens

<400> SEQUENCE: 306

Gly Lys Arg Ser Arg Thr
1               5

<210> SEQ ID NO 307
<211> LENGTH: 6
<212> TYPE: PRT
<213> ORGANISM: Homo sapiens

<400> SEQUENCE: 307

Pro Lys Arg Lys Lys Ala
1               5

<210> SEQ ID NO 308
<211> LENGTH: 6
<212> TYPE: PRT
<213> ORGANISM: Homo sapiens

<400> SEQUENCE: 308

Gly Lys Arg Glu Lys Ser
1               5
```

```
<210> SEQ ID NO 309
<211> LENGTH: 6
<212> TYPE: PRT
<213> ORGANISM: Homo sapiens

<400> SEQUENCE: 309

His Lys Lys His Lys Lys
1               5

<210> SEQ ID NO 310
<211> LENGTH: 6
<212> TYPE: PRT
<213> ORGANISM: Homo sapiens

<400> SEQUENCE: 310

Lys Lys Lys Val Lys Asp
1               5

<210> SEQ ID NO 311
<211> LENGTH: 6
<212> TYPE: PRT
<213> ORGANISM: Homo sapiens

<400> SEQUENCE: 311

Glu Arg Lys Glu Arg Glu
1               5

<210> SEQ ID NO 312
<211> LENGTH: 6
<212> TYPE: PRT
<213> ORGANISM: Homo sapiens

<400> SEQUENCE: 312

Glu Arg Lys Glu Arg Glu
1               5

<210> SEQ ID NO 313
<211> LENGTH: 6
<212> TYPE: PRT
<213> ORGANISM: Homo sapiens

<400> SEQUENCE: 313

Ser Arg Lys Asn Arg Thr
1               5

<210> SEQ ID NO 314
<211> LENGTH: 6
<212> TYPE: PRT
<213> ORGANISM: Homo sapiens

<400> SEQUENCE: 314

Ser Arg Lys Asn Arg Thr
1               5

<210> SEQ ID NO 315
<211> LENGTH: 6
<212> TYPE: PRT
<213> ORGANISM: Homo sapiens

<400> SEQUENCE: 315

Gly Arg Arg Lys Arg Asn
1               5

<210> SEQ ID NO 316
```

```
<211> LENGTH: 6
<212> TYPE: PRT
<213> ORGANISM: Homo sapiens

<400> SEQUENCE: 316

Ala Arg Arg Gln Arg Arg
1               5

<210> SEQ ID NO 317
<211> LENGTH: 6
<212> TYPE: PRT
<213> ORGANISM: Homo sapiens

<400> SEQUENCE: 317

Gly Arg Arg Lys Arg Asn
1               5

<210> SEQ ID NO 318
<211> LENGTH: 6
<212> TYPE: PRT
<213> ORGANISM: Homo sapiens

<400> SEQUENCE: 318

Ala Arg Arg Gln Arg Arg
1               5

<210> SEQ ID NO 319
<211> LENGTH: 6
<212> TYPE: PRT
<213> ORGANISM: Homo sapiens

<400> SEQUENCE: 319

Cys Lys Arg Leu Lys Ser
1               5

<210> SEQ ID NO 320
<211> LENGTH: 6
<212> TYPE: PRT
<213> ORGANISM: Homo sapiens

<400> SEQUENCE: 320

Cys Lys Arg Leu Lys Ser
1               5

<210> SEQ ID NO 321
<211> LENGTH: 6
<212> TYPE: PRT
<213> ORGANISM: Homo sapiens

<400> SEQUENCE: 321

His Lys Arg Leu Arg Gln
1               5

<210> SEQ ID NO 322
<211> LENGTH: 6
<212> TYPE: PRT
<213> ORGANISM: Homo sapiens

<400> SEQUENCE: 322

His Lys Arg Leu Arg Gln
1               5

<210> SEQ ID NO 323
<211> LENGTH: 8
<212> TYPE: PRT
```

<213> ORGANISM: Homo sapiens

<400> SEQUENCE: 323

Pro Arg Lys Arg Leu Thr Lys Gly
1               5

<210> SEQ ID NO 324
<211> LENGTH: 8
<212> TYPE: PRT
<213> ORGANISM: Homo sapiens

<400> SEQUENCE: 324

Arg Lys Arg Arg Lys Glu Lys Ser
1               5

<210> SEQ ID NO 325
<211> LENGTH: 8
<212> TYPE: PRT
<213> ORGANISM: Homo sapiens

<400> SEQUENCE: 325

Pro Lys Lys Lys Arg Leu Arg Leu
1               5

<210> SEQ ID NO 326
<211> LENGTH: 6
<212> TYPE: PRT
<213> ORGANISM: Homo sapiens

<400> SEQUENCE: 326

His Lys Lys Glu Arg Lys
1               5

<210> SEQ ID NO 327
<211> LENGTH: 6
<212> TYPE: PRT
<213> ORGANISM: Homo sapiens

<400> SEQUENCE: 327

Thr Lys Lys Thr Lys Lys
1               5

<210> SEQ ID NO 328
<211> LENGTH: 6
<212> TYPE: PRT
<213> ORGANISM: Homo sapiens

<400> SEQUENCE: 328

Leu Arg Lys Arg Arg Lys
1               5

<210> SEQ ID NO 329
<211> LENGTH: 6
<212> TYPE: PRT
<213> ORGANISM: Homo sapiens

<400> SEQUENCE: 329

Pro Lys Lys Lys Arg Leu
1               5

<210> SEQ ID NO 330
<211> LENGTH: 6
<212> TYPE: PRT
<213> ORGANISM: Homo sapiens

```
<400> SEQUENCE: 330

Gln Lys Arg Val Lys Glu
1               5

<210> SEQ ID NO 331
<211> LENGTH: 6
<212> TYPE: PRT
<213> ORGANISM: Homo sapiens

<400> SEQUENCE: 331

Ser Arg Lys Pro Arg Met
1               5

<210> SEQ ID NO 332
<211> LENGTH: 6
<212> TYPE: PRT
<213> ORGANISM: Homo sapiens

<400> SEQUENCE: 332

His Lys Lys Glu Arg Lys
1               5

<210> SEQ ID NO 333
<211> LENGTH: 6
<212> TYPE: PRT
<213> ORGANISM: Homo sapiens

<400> SEQUENCE: 333

Thr Lys Lys Thr Lys Lys
1               5

<210> SEQ ID NO 334
<211> LENGTH: 6
<212> TYPE: PRT
<213> ORGANISM: Homo sapiens

<400> SEQUENCE: 334

Leu Arg Lys Arg Arg Lys
1               5

<210> SEQ ID NO 335
<211> LENGTH: 6
<212> TYPE: PRT
<213> ORGANISM: Homo sapiens

<400> SEQUENCE: 335

Pro Lys Lys Lys Arg Leu
1               5

<210> SEQ ID NO 336
<211> LENGTH: 6
<212> TYPE: PRT
<213> ORGANISM: Homo sapiens

<400> SEQUENCE: 336

Gln Lys Arg Val Lys Glu
1               5

<210> SEQ ID NO 337
<211> LENGTH: 6
<212> TYPE: PRT
<213> ORGANISM: Homo sapiens

<400> SEQUENCE: 337
```

```
Ser Arg Lys Pro Arg Met
1               5

<210> SEQ ID NO 338
<211> LENGTH: 6
<212> TYPE: PRT
<213> ORGANISM: Homo sapiens

<400> SEQUENCE: 338

Ser Lys Arg Lys Lys Ala
1               5

<210> SEQ ID NO 339
<211> LENGTH: 6
<212> TYPE: PRT
<213> ORGANISM: Homo sapiens

<400> SEQUENCE: 339

Ile Lys Lys Ala Arg Ala
1               5

<210> SEQ ID NO 340
<211> LENGTH: 6
<212> TYPE: PRT
<213> ORGANISM: Homo sapiens

<400> SEQUENCE: 340

Ser Lys Arg Lys Lys Ala
1               5

<210> SEQ ID NO 341
<211> LENGTH: 6
<212> TYPE: PRT
<213> ORGANISM: Homo sapiens

<400> SEQUENCE: 341

Ile Lys Lys Ala Arg Ala
1               5

<210> SEQ ID NO 342
<211> LENGTH: 8
<212> TYPE: PRT
<213> ORGANISM: Homo sapiens

<400> SEQUENCE: 342

Arg Lys Lys Arg Ser Gln Arg Pro
1               5

<210> SEQ ID NO 343
<211> LENGTH: 6
<212> TYPE: PRT
<213> ORGANISM: Homo sapiens

<400> SEQUENCE: 343

Phe Arg Lys Lys Arg Ser
1               5

<210> SEQ ID NO 344
<211> LENGTH: 6
<212> TYPE: PRT
<213> ORGANISM: Homo sapiens

<400> SEQUENCE: 344

Phe Arg Lys Lys Arg Ser
1               5
```

```
<210> SEQ ID NO 345
<211> LENGTH: 8
<212> TYPE: PRT
<213> ORGANISM: Homo sapiens

<400> SEQUENCE: 345

Leu Lys Arg Lys Leu Ile Arg Leu
1               5

<210> SEQ ID NO 346
<211> LENGTH: 8
<212> TYPE: PRT
<213> ORGANISM: Homo sapiens

<400> SEQUENCE: 346

Arg Lys Lys Arg Arg Ala Arg Leu
1               5

<210> SEQ ID NO 347
<211> LENGTH: 6
<212> TYPE: PRT
<213> ORGANISM: Homo sapiens

<400> SEQUENCE: 347

Ala Arg Arg Leu Arg Glu
1               5

<210> SEQ ID NO 348
<211> LENGTH: 6
<212> TYPE: PRT
<213> ORGANISM: Homo sapiens

<400> SEQUENCE: 348

Glu Arg Lys Lys Arg Arg
1               5

<210> SEQ ID NO 349
<211> LENGTH: 6
<212> TYPE: PRT
<213> ORGANISM: Homo sapiens

<400> SEQUENCE: 349

Cys Lys Lys Ser Arg Lys
1               5

<210> SEQ ID NO 350
<211> LENGTH: 6
<212> TYPE: PRT
<213> ORGANISM: Homo sapiens

<400> SEQUENCE: 350

Ala Arg Arg Leu Arg Glu
1               5

<210> SEQ ID NO 351
<211> LENGTH: 6
<212> TYPE: PRT
<213> ORGANISM: Homo sapiens

<400> SEQUENCE: 351

Glu Arg Lys Lys Arg Arg
1               5
```

```
<210> SEQ ID NO 352
<211> LENGTH: 6
<212> TYPE: PRT
<213> ORGANISM: Homo sapiens

<400> SEQUENCE: 352

Cys Lys Lys Ser Arg Lys
1               5

<210> SEQ ID NO 353
<211> LENGTH: 6
<212> TYPE: PRT
<213> ORGANISM: Homo sapiens

<400> SEQUENCE: 353

His Lys Arg Met Lys Val
1               5

<210> SEQ ID NO 354
<211> LENGTH: 6
<212> TYPE: PRT
<213> ORGANISM: Homo sapiens

<400> SEQUENCE: 354

Leu Lys Arg Phe Lys Tyr
1               5

<210> SEQ ID NO 355
<211> LENGTH: 6
<212> TYPE: PRT
<213> ORGANISM: Homo sapiens

<400> SEQUENCE: 355

His Lys Arg Met Lys Val
1               5

<210> SEQ ID NO 356
<211> LENGTH: 6
<212> TYPE: PRT
<213> ORGANISM: Homo sapiens

<400> SEQUENCE: 356

Leu Lys Arg Phe Lys Tyr
1               5

<210> SEQ ID NO 357
<211> LENGTH: 6
<212> TYPE: PRT
<213> ORGANISM: Homo sapiens

<400> SEQUENCE: 357

His Arg Lys Pro Lys Leu
1               5

<210> SEQ ID NO 358
<211> LENGTH: 6
<212> TYPE: PRT
<213> ORGANISM: Homo sapiens

<400> SEQUENCE: 358

His Arg Lys Pro Lys Leu
1               5

<210> SEQ ID NO 359
<211> LENGTH: 6
```

```
<212> TYPE: PRT
<213> ORGANISM: Homo sapiens

<400> SEQUENCE: 359

Leu Lys Arg Ser Arg Pro
1               5

<210> SEQ ID NO 360
<211> LENGTH: 6
<212> TYPE: PRT
<213> ORGANISM: Homo sapiens

<400> SEQUENCE: 360

Pro Arg Lys Ser Arg Arg
1               5

<210> SEQ ID NO 361
<211> LENGTH: 6
<212> TYPE: PRT
<213> ORGANISM: Homo sapiens

<400> SEQUENCE: 361

Leu Lys Arg Ser Arg Pro
1               5

<210> SEQ ID NO 362
<211> LENGTH: 6
<212> TYPE: PRT
<213> ORGANISM: Homo sapiens

<400> SEQUENCE: 362

Pro Arg Lys Ser Arg Arg
1               5

<210> SEQ ID NO 363
<211> LENGTH: 6
<212> TYPE: PRT
<213> ORGANISM: Homo sapiens

<400> SEQUENCE: 363

Asp Arg Arg Thr Arg Leu
1               5

<210> SEQ ID NO 364
<211> LENGTH: 6
<212> TYPE: PRT
<213> ORGANISM: Homo sapiens

<400> SEQUENCE: 364

Asp Arg Arg Thr Arg Leu
1               5

<210> SEQ ID NO 365
<211> LENGTH: 8
<212> TYPE: PRT
<213> ORGANISM: Homo sapiens

<400> SEQUENCE: 365

Gly Arg Arg Lys Ser Glu Arg Gln
1               5

<210> SEQ ID NO 366
<211> LENGTH: 6
<212> TYPE: PRT
<213> ORGANISM: Homo sapiens
```

```
<400> SEQUENCE: 366

Ser Arg Arg Phe Arg Cys
1               5

<210> SEQ ID NO 367
<211> LENGTH: 6
<212> TYPE: PRT
<213> ORGANISM: Homo sapiens

<400> SEQUENCE: 367

Asn Lys Lys Arg Arg Gln
1               5

<210> SEQ ID NO 368
<211> LENGTH: 6
<212> TYPE: PRT
<213> ORGANISM: Homo sapiens

<400> SEQUENCE: 368

Ser Arg Arg Phe Arg Cys
1               5

<210> SEQ ID NO 369
<211> LENGTH: 6
<212> TYPE: PRT
<213> ORGANISM: Homo sapiens

<400> SEQUENCE: 369

Asn Lys Lys Arg Arg Gln
1               5

<210> SEQ ID NO 370
<211> LENGTH: 6
<212> TYPE: PRT
<213> ORGANISM: Homo sapiens

<400> SEQUENCE: 370

Glu Lys Arg Pro Arg Asp
1               5

<210> SEQ ID NO 371
<211> LENGTH: 6
<212> TYPE: PRT
<213> ORGANISM: Homo sapiens

<400> SEQUENCE: 371

Ala Arg Arg Leu Lys Lys
1               5

<210> SEQ ID NO 372
<211> LENGTH: 6
<212> TYPE: PRT
<213> ORGANISM: Homo sapiens

<400> SEQUENCE: 372

Glu Lys Arg Pro Arg Asp
1               5

<210> SEQ ID NO 373
<211> LENGTH: 6
<212> TYPE: PRT
<213> ORGANISM: Homo sapiens

<400> SEQUENCE: 373
```

```
Ala Arg Arg Leu Lys Lys
1               5

<210> SEQ ID NO 374
<211> LENGTH: 6
<212> TYPE: PRT
<213> ORGANISM: Homo sapiens

<400> SEQUENCE: 374

Gln Lys Lys Ile Arg Ile
1               5

<210> SEQ ID NO 375
<211> LENGTH: 6
<212> TYPE: PRT
<213> ORGANISM: Homo sapiens

<400> SEQUENCE: 375

Gln Lys Lys Ile Arg Ile
1               5

<210> SEQ ID NO 376
<211> LENGTH: 6
<212> TYPE: PRT
<213> ORGANISM: Homo sapiens

<400> SEQUENCE: 376

Phe Arg Lys Ala Arg Ser
1               5

<210> SEQ ID NO 377
<211> LENGTH: 6
<212> TYPE: PRT
<213> ORGANISM: Homo sapiens

<400> SEQUENCE: 377

Phe Arg Lys Ala Arg Ser
1               5

<210> SEQ ID NO 378
<211> LENGTH: 6
<212> TYPE: PRT
<213> ORGANISM: Homo sapiens

<400> SEQUENCE: 378

Glu Arg Lys Ala Lys Leu
1               5

<210> SEQ ID NO 379
<211> LENGTH: 6
<212> TYPE: PRT
<213> ORGANISM: Homo sapiens

<400> SEQUENCE: 379

Glu Arg Lys Ala Lys Leu
1               5

<210> SEQ ID NO 380
<211> LENGTH: 8
<212> TYPE: PRT
<213> ORGANISM: Homo sapiens

<400> SEQUENCE: 380

Glu Lys Lys Lys Lys Lys Lys Lys
```

-continued

```
1               5

<210> SEQ ID NO 381
<211> LENGTH: 6
<212> TYPE: PRT
<213> ORGANISM: Homo sapiens

<400> SEQUENCE: 381

Leu Arg Lys His Arg His
1               5

<210> SEQ ID NO 382
<211> LENGTH: 6
<212> TYPE: PRT
<213> ORGANISM: Homo sapiens

<400> SEQUENCE: 382

Leu Lys Lys Phe Lys Thr
1               5

<210> SEQ ID NO 383
<211> LENGTH: 6
<212> TYPE: PRT
<213> ORGANISM: Homo sapiens

<400> SEQUENCE: 383

Asp Lys Lys Lys Lys Glu
1               5

<210> SEQ ID NO 384
<211> LENGTH: 6
<212> TYPE: PRT
<213> ORGANISM: Homo sapiens

<400> SEQUENCE: 384

Glu Lys Lys Lys Lys Lys
1               5

<210> SEQ ID NO 385
<211> LENGTH: 6
<212> TYPE: PRT
<213> ORGANISM: Homo sapiens

<400> SEQUENCE: 385

Leu Arg Lys His Arg His
1               5

<210> SEQ ID NO 386
<211> LENGTH: 6
<212> TYPE: PRT
<213> ORGANISM: Homo sapiens

<400> SEQUENCE: 386

Leu Lys Lys Phe Lys Thr
1               5

<210> SEQ ID NO 387
<211> LENGTH: 6
<212> TYPE: PRT
<213> ORGANISM: Homo sapiens

<400> SEQUENCE: 387

Asp Lys Lys Lys Lys Glu
1               5
```

```
<210> SEQ ID NO 388
<211> LENGTH: 6
<212> TYPE: PRT
<213> ORGANISM: Homo sapiens

<400> SEQUENCE: 388

Glu Lys Lys Lys Lys Lys
1               5

<210> SEQ ID NO 389
<211> LENGTH: 6
<212> TYPE: PRT
<213> ORGANISM: Homo sapiens

<400> SEQUENCE: 389

Tyr Lys Arg Tyr Lys Val
1               5

<210> SEQ ID NO 390
<211> LENGTH: 6
<212> TYPE: PRT
<213> ORGANISM: Homo sapiens

<400> SEQUENCE: 390

Glu Lys Lys Lys Arg Glu
1               5

<210> SEQ ID NO 391
<211> LENGTH: 6
<212> TYPE: PRT
<213> ORGANISM: Homo sapiens

<400> SEQUENCE: 391

Leu Lys Arg Ile Arg Glu
1               5

<210> SEQ ID NO 392
<211> LENGTH: 6
<212> TYPE: PRT
<213> ORGANISM: Homo sapiens

<400> SEQUENCE: 392

Leu Lys Lys Thr Lys Cys
1               5

<210> SEQ ID NO 393
<211> LENGTH: 6
<212> TYPE: PRT
<213> ORGANISM: Homo sapiens

<400> SEQUENCE: 393

Tyr Lys Arg Tyr Lys Val
1               5

<210> SEQ ID NO 394
<211> LENGTH: 6
<212> TYPE: PRT
<213> ORGANISM: Homo sapiens

<400> SEQUENCE: 394

Glu Lys Lys Lys Arg Glu
1               5

<210> SEQ ID NO 395
```

```
<211> LENGTH: 6
<212> TYPE: PRT
<213> ORGANISM: Homo sapiens

<400> SEQUENCE: 395

Leu Lys Arg Ile Arg Glu
1               5

<210> SEQ ID NO 396
<211> LENGTH: 6
<212> TYPE: PRT
<213> ORGANISM: Homo sapiens

<400> SEQUENCE: 396

Leu Lys Lys Thr Lys Cys
1               5

<210> SEQ ID NO 397
<211> LENGTH: 8
<212> TYPE: PRT
<213> ORGANISM: Homo sapiens

<400> SEQUENCE: 397

Arg Lys Arg Lys Ser Val Arg Gly
1               5

<210> SEQ ID NO 398
<211> LENGTH: 6
<212> TYPE: PRT
<213> ORGANISM: Homo sapiens

<400> SEQUENCE: 398

Glu Arg Lys Arg Lys Ser
1               5

<210> SEQ ID NO 399
<211> LENGTH: 6
<212> TYPE: PRT
<213> ORGANISM: Homo sapiens

<400> SEQUENCE: 399

Glu Arg Lys Arg Lys Ser
1               5

<210> SEQ ID NO 400
<211> LENGTH: 6
<212> TYPE: PRT
<213> ORGANISM: Homo sapiens

<400> SEQUENCE: 400

Arg Arg Lys Ser Arg Phe
1               5

<210> SEQ ID NO 401
<211> LENGTH: 6
<212> TYPE: PRT
<213> ORGANISM: Homo sapiens

<400> SEQUENCE: 401

Phe Lys Arg Pro Lys Ala
1               5

<210> SEQ ID NO 402
<211> LENGTH: 6
<212> TYPE: PRT
```

<213> ORGANISM: Homo sapiens

<400> SEQUENCE: 402

Arg Arg Lys Ser Arg Phe
1               5

<210> SEQ ID NO 403
<211> LENGTH: 6
<212> TYPE: PRT
<213> ORGANISM: Homo sapiens

<400> SEQUENCE: 403

Phe Lys Arg Pro Lys Ala
1               5

<210> SEQ ID NO 404
<211> LENGTH: 6
<212> TYPE: PRT
<213> ORGANISM: Homo sapiens

<400> SEQUENCE: 404

Ala Arg Lys Val Lys Ser
1               5

<210> SEQ ID NO 405
<211> LENGTH: 6
<212> TYPE: PRT
<213> ORGANISM: Homo sapiens

<400> SEQUENCE: 405

Ala Arg Lys Val Lys Ser
1               5

<210> SEQ ID NO 406
<211> LENGTH: 6
<212> TYPE: PRT
<213> ORGANISM: Homo sapiens

<400> SEQUENCE: 406

Phe Lys Lys Thr Arg Tyr
1               5

<210> SEQ ID NO 407
<211> LENGTH: 6
<212> TYPE: PRT
<213> ORGANISM: Homo sapiens

<400> SEQUENCE: 407

Phe Lys Lys Thr Arg Tyr
1               5

<210> SEQ ID NO 408
<211> LENGTH: 8
<212> TYPE: PRT
<213> ORGANISM: Homo sapiens

<400> SEQUENCE: 408

Pro Lys Lys Lys Gly Ile Lys Ser
1               5

<210> SEQ ID NO 409
<211> LENGTH: 6
<212> TYPE: PRT
<213> ORGANISM: Homo sapiens

```
<400> SEQUENCE: 409

Ile Arg Arg Pro Arg Arg
1               5

<210> SEQ ID NO 410
<211> LENGTH: 6
<212> TYPE: PRT
<213> ORGANISM: Homo sapiens

<400> SEQUENCE: 410

Leu Arg Lys His Arg Arg
1               5

<210> SEQ ID NO 411
<211> LENGTH: 6
<212> TYPE: PRT
<213> ORGANISM: Homo sapiens

<400> SEQUENCE: 411

Gly Lys Lys Glu Lys Ala
1               5

<210> SEQ ID NO 412
<211> LENGTH: 6
<212> TYPE: PRT
<213> ORGANISM: Homo sapiens

<400> SEQUENCE: 412

Asp Arg Arg Leu Lys Lys
1               5

<210> SEQ ID NO 413
<211> LENGTH: 6
<212> TYPE: PRT
<213> ORGANISM: Homo sapiens

<400> SEQUENCE: 413

Ile Arg Arg Pro Arg Arg
1               5

<210> SEQ ID NO 414
<211> LENGTH: 6
<212> TYPE: PRT
<213> ORGANISM: Homo sapiens

<400> SEQUENCE: 414

Leu Arg Lys His Arg Arg
1               5

<210> SEQ ID NO 415
<211> LENGTH: 6
<212> TYPE: PRT
<213> ORGANISM: Homo sapiens

<400> SEQUENCE: 415

Gly Lys Lys Glu Lys Ala
1               5

<210> SEQ ID NO 416
<211> LENGTH: 6
<212> TYPE: PRT
<213> ORGANISM: Homo sapiens

<400> SEQUENCE: 416
```

```
Asp Arg Arg Leu Lys Lys
1               5

<210> SEQ ID NO 417
<211> LENGTH: 8
<212> TYPE: PRT
<213> ORGANISM: Homo sapiens

<400> SEQUENCE: 417

Asp Lys Arg Lys Cys Glu Arg Leu
1               5

<210> SEQ ID NO 418
<211> LENGTH: 8
<212> TYPE: PRT
<213> ORGANISM: Homo sapiens

<400> SEQUENCE: 418

Pro Arg Lys Lys Arg Leu Lys Ser
1               5

<210> SEQ ID NO 419
<211> LENGTH: 6
<212> TYPE: PRT
<213> ORGANISM: Homo sapiens

<400> SEQUENCE: 419

Asn Lys Lys Gly Lys Ala
1               5

<210> SEQ ID NO 420
<211> LENGTH: 6
<212> TYPE: PRT
<213> ORGANISM: Homo sapiens

<400> SEQUENCE: 420

Pro Arg Lys Lys Arg Leu
1               5

<210> SEQ ID NO 421
<211> LENGTH: 6
<212> TYPE: PRT
<213> ORGANISM: Homo sapiens

<400> SEQUENCE: 421

Asn Lys Lys Gly Lys Ala
1               5

<210> SEQ ID NO 422
<211> LENGTH: 6
<212> TYPE: PRT
<213> ORGANISM: Homo sapiens

<400> SEQUENCE: 422

Pro Arg Lys Lys Arg Leu
1               5

<210> SEQ ID NO 423
<211> LENGTH: 6
<212> TYPE: PRT
<213> ORGANISM: Homo sapiens

<400> SEQUENCE: 423

Gln Arg Arg Asn Lys Arg
1               5
```

```
<210> SEQ ID NO 424
<211> LENGTH: 6
<212> TYPE: PRT
<213> ORGANISM: Homo sapiens

<400> SEQUENCE: 424

Gln Arg Arg Asn Lys Arg
1               5

<210> SEQ ID NO 425
<211> LENGTH: 6
<212> TYPE: PRT
<213> ORGANISM: Homo sapiens

<400> SEQUENCE: 425

Tyr Arg Lys Ile Lys Leu
1               5

<210> SEQ ID NO 426
<211> LENGTH: 6
<212> TYPE: PRT
<213> ORGANISM: Homo sapiens

<400> SEQUENCE: 426

Tyr Arg Lys Ile Lys Leu
1               5

<210> SEQ ID NO 427
<211> LENGTH: 6
<212> TYPE: PRT
<213> ORGANISM: Homo sapiens

<400> SEQUENCE: 427

Val Arg Arg His Arg Asn
1               5

<210> SEQ ID NO 428
<211> LENGTH: 6
<212> TYPE: PRT
<213> ORGANISM: Homo sapiens

<400> SEQUENCE: 428

Trp Lys Arg Leu Lys Asp
1               5

<210> SEQ ID NO 429
<211> LENGTH: 6
<212> TYPE: PRT
<213> ORGANISM: Homo sapiens

<400> SEQUENCE: 429

Val Arg Arg His Arg Asn
1               5

<210> SEQ ID NO 430
<211> LENGTH: 6
<212> TYPE: PRT
<213> ORGANISM: Homo sapiens

<400> SEQUENCE: 430

Trp Lys Arg Leu Lys Asp
1               5
```

```
<210> SEQ ID NO 431
<211> LENGTH: 8
<212> TYPE: PRT
<213> ORGANISM: Homo sapiens

<400> SEQUENCE: 431

Leu Arg Arg Arg Arg Gly Arg Glu
1               5

<210> SEQ ID NO 432
<211> LENGTH: 8
<212> TYPE: PRT
<213> ORGANISM: Homo sapiens

<400> SEQUENCE: 432

Leu Lys Lys Arg Ser Gly Lys Lys
1               5

<210> SEQ ID NO 433
<211> LENGTH: 6
<212> TYPE: PRT
<213> ORGANISM: Homo sapiens

<400> SEQUENCE: 433

Leu Arg Arg Arg Arg Gly
1               5

<210> SEQ ID NO 434
<211> LENGTH: 6
<212> TYPE: PRT
<213> ORGANISM: Homo sapiens

<400> SEQUENCE: 434

Gly Lys Lys Asp Lys His
1               5

<210> SEQ ID NO 435
<211> LENGTH: 6
<212> TYPE: PRT
<213> ORGANISM: Homo sapiens

<400> SEQUENCE: 435

Leu Arg Arg Arg Arg Gly
1               5

<210> SEQ ID NO 436
<211> LENGTH: 6
<212> TYPE: PRT
<213> ORGANISM: Homo sapiens

<400> SEQUENCE: 436

Gly Lys Lys Asp Lys His
1               5

<210> SEQ ID NO 437
<211> LENGTH: 6
<212> TYPE: PRT
<213> ORGANISM: Homo sapiens

<400> SEQUENCE: 437

Leu Lys Lys Lys Lys Lys
1               5

<210> SEQ ID NO 438
<211> LENGTH: 6
```

```
<212> TYPE: PRT
<213> ORGANISM: Homo sapiens

<400> SEQUENCE: 438

Leu Lys Lys Lys Lys Lys
1               5

<210> SEQ ID NO 439
<211> LENGTH: 6
<212> TYPE: PRT
<213> ORGANISM: Homo sapiens

<400> SEQUENCE: 439

Ala Arg Lys Arg Lys Arg
1               5

<210> SEQ ID NO 440
<211> LENGTH: 6
<212> TYPE: PRT
<213> ORGANISM: Homo sapiens

<400> SEQUENCE: 440

Ala Arg Lys Arg Lys Arg
1               5

<210> SEQ ID NO 441
<211> LENGTH: 6
<212> TYPE: PRT
<213> ORGANISM: Homo sapiens

<400> SEQUENCE: 441

Pro Lys Lys Lys Arg Leu
1               5

<210> SEQ ID NO 442
<211> LENGTH: 6
<212> TYPE: PRT
<213> ORGANISM: Homo sapiens

<400> SEQUENCE: 442

Ser Lys Arg Asn Arg Arg
1               5

<210> SEQ ID NO 443
<211> LENGTH: 6
<212> TYPE: PRT
<213> ORGANISM: Homo sapiens

<400> SEQUENCE: 443

Ile Arg Arg Asn Lys Gly
1               5

<210> SEQ ID NO 444
<211> LENGTH: 6
<212> TYPE: PRT
<213> ORGANISM: Homo sapiens

<400> SEQUENCE: 444

Gly Lys Lys Glu Lys Glu
1               5

<210> SEQ ID NO 445
<211> LENGTH: 6
<212> TYPE: PRT
<213> ORGANISM: Homo sapiens
```

```
<400> SEQUENCE: 445

Pro Lys Lys Lys Arg Leu
1               5

<210> SEQ ID NO 446
<211> LENGTH: 6
<212> TYPE: PRT
<213> ORGANISM: Homo sapiens

<400> SEQUENCE: 446

Ser Lys Arg Asn Arg Arg
1               5

<210> SEQ ID NO 447
<211> LENGTH: 6
<212> TYPE: PRT
<213> ORGANISM: Homo sapiens

<400> SEQUENCE: 447

Ile Arg Arg Asn Lys Gly
1               5

<210> SEQ ID NO 448
<211> LENGTH: 6
<212> TYPE: PRT
<213> ORGANISM: Homo sapiens

<400> SEQUENCE: 448

Gly Lys Lys Glu Lys Glu
1               5

<210> SEQ ID NO 449
<211> LENGTH: 6
<212> TYPE: PRT
<213> ORGANISM: Homo sapiens

<400> SEQUENCE: 449

Thr Arg Arg Ser Arg Ala
1               5

<210> SEQ ID NO 450
<211> LENGTH: 6
<212> TYPE: PRT
<213> ORGANISM: Homo sapiens

<400> SEQUENCE: 450

Thr Arg Arg Ser Arg Ala
1               5

<210> SEQ ID NO 451
<211> LENGTH: 8
<212> TYPE: PRT
<213> ORGANISM: Homo sapiens

<400> SEQUENCE: 451

Ile Arg Arg Arg Phe Glu Lys Arg
1               5

<210> SEQ ID NO 452
<211> LENGTH: 6
<212> TYPE: PRT
<213> ORGANISM: Homo sapiens

<400> SEQUENCE: 452
```

```
Ala Arg Arg Ile Lys Thr
1               5

<210> SEQ ID NO 453
<211> LENGTH: 6
<212> TYPE: PRT
<213> ORGANISM: Homo sapiens

<400> SEQUENCE: 453

Phe Lys Lys Val Arg Gly
1               5

<210> SEQ ID NO 454
<211> LENGTH: 6
<212> TYPE: PRT
<213> ORGANISM: Homo sapiens

<400> SEQUENCE: 454

Ala Arg Arg Ile Lys Thr
1               5

<210> SEQ ID NO 455
<211> LENGTH: 6
<212> TYPE: PRT
<213> ORGANISM: Homo sapiens

<400> SEQUENCE: 455

Phe Lys Lys Val Arg Gly
1               5

<210> SEQ ID NO 456
<211> LENGTH: 8
<212> TYPE: PRT
<213> ORGANISM: Homo sapiens

<400> SEQUENCE: 456

His Arg Lys Arg Ser Arg Arg Val
1               5

<210> SEQ ID NO 457
<211> LENGTH: 6
<212> TYPE: PRT
<213> ORGANISM: Homo sapiens

<400> SEQUENCE: 457

Arg Lys Arg Ser Arg Arg
1               5

<210> SEQ ID NO 458
<211> LENGTH: 6
<212> TYPE: PRT
<213> ORGANISM: Homo sapiens

<400> SEQUENCE: 458

Arg Lys Arg Ser Arg Arg
1               5

<210> SEQ ID NO 459
<211> LENGTH: 8
<212> TYPE: PRT
<213> ORGANISM: Homo sapiens

<400> SEQUENCE: 459

Thr Lys Arg Lys Lys Arg Arg Glu
```

```
1               5

<210> SEQ ID NO 460
<211> LENGTH: 6
<212> TYPE: PRT
<213> ORGANISM: Homo sapiens

<400> SEQUENCE: 460

Thr Lys Arg Lys Lys Arg
1               5

<210> SEQ ID NO 461
<211> LENGTH: 6
<212> TYPE: PRT
<213> ORGANISM: Homo sapiens

<400> SEQUENCE: 461

Thr Lys Arg Lys Lys Arg
1               5

<210> SEQ ID NO 462
<211> LENGTH: 6
<212> TYPE: PRT
<213> ORGANISM: Homo sapiens

<400> SEQUENCE: 462

Thr Arg Arg Lys Arg His
1               5

<210> SEQ ID NO 463
<211> LENGTH: 6
<212> TYPE: PRT
<213> ORGANISM: Homo sapiens

<400> SEQUENCE: 463

Thr Arg Arg Lys Arg His
1               5

<210> SEQ ID NO 464
<211> LENGTH: 6
<212> TYPE: PRT
<213> ORGANISM: Homo sapiens

<400> SEQUENCE: 464

Pro Lys Lys Gly Arg Val
1               5

<210> SEQ ID NO 465
<211> LENGTH: 6
<212> TYPE: PRT
<213> ORGANISM: Homo sapiens

<400> SEQUENCE: 465

Arg Arg Arg His Arg Thr
1               5

<210> SEQ ID NO 466
<211> LENGTH: 6
<212> TYPE: PRT
<213> ORGANISM: Homo sapiens

<400> SEQUENCE: 466

Asn Arg Arg Ala Lys Gln
1               5
```

```
<210> SEQ ID NO 467
<211> LENGTH: 6
<212> TYPE: PRT
<213> ORGANISM: Homo sapiens

<400> SEQUENCE: 467

Pro Lys Lys Gly Arg Val
1               5

<210> SEQ ID NO 468
<211> LENGTH: 6
<212> TYPE: PRT
<213> ORGANISM: Homo sapiens

<400> SEQUENCE: 468

Arg Arg Arg His Arg Thr
1               5

<210> SEQ ID NO 469
<211> LENGTH: 6
<212> TYPE: PRT
<213> ORGANISM: Homo sapiens

<400> SEQUENCE: 469

Asn Arg Arg Ala Lys Gln
1               5

<210> SEQ ID NO 470
<211> LENGTH: 8
<212> TYPE: PRT
<213> ORGANISM: Homo sapiens

<400> SEQUENCE: 470

Tyr Arg Arg Arg Glu Ser Lys Arg
1               5

<210> SEQ ID NO 471
<211> LENGTH: 8
<212> TYPE: PRT
<213> ORGANISM: Homo sapiens

<400> SEQUENCE: 471

Met Arg Lys Arg Arg Leu Arg Glu
1               5

<210> SEQ ID NO 472
<211> LENGTH: 6
<212> TYPE: PRT
<213> ORGANISM: Homo sapiens

<400> SEQUENCE: 472

Ser Lys Arg Lys Lys Ser
1               5

<210> SEQ ID NO 473
<211> LENGTH: 6
<212> TYPE: PRT
<213> ORGANISM: Homo sapiens

<400> SEQUENCE: 473

Met Arg Lys Arg Arg Leu
1               5

<210> SEQ ID NO 474
```

```
<211> LENGTH: 6
<212> TYPE: PRT
<213> ORGANISM: Homo sapiens

<400> SEQUENCE: 474

Ser Lys Arg Lys Lys Ser
1               5

<210> SEQ ID NO 475
<211> LENGTH: 6
<212> TYPE: PRT
<213> ORGANISM: Homo sapiens

<400> SEQUENCE: 475

Met Arg Lys Arg Arg Leu
1               5

<210> SEQ ID NO 476
<211> LENGTH: 8
<212> TYPE: PRT
<213> ORGANISM: Homo sapiens

<400> SEQUENCE: 476

Leu Lys Lys Lys Gln Arg Arg Gln
1               5

<210> SEQ ID NO 477
<211> LENGTH: 6
<212> TYPE: PRT
<213> ORGANISM: Homo sapiens

<400> SEQUENCE: 477

Lys Lys Lys Gln Arg Arg
1               5

<210> SEQ ID NO 478
<211> LENGTH: 6
<212> TYPE: PRT
<213> ORGANISM: Homo sapiens

<400> SEQUENCE: 478

Asn Arg Arg Ala Lys Trp
1               5

<210> SEQ ID NO 479
<211> LENGTH: 6
<212> TYPE: PRT
<213> ORGANISM: Homo sapiens

<400> SEQUENCE: 479

Arg Lys Arg Glu Arg Ser
1               5

<210> SEQ ID NO 480
<211> LENGTH: 6
<212> TYPE: PRT
<213> ORGANISM: Homo sapiens

<400> SEQUENCE: 480

Lys Lys Lys Gln Arg Arg
1               5

<210> SEQ ID NO 481
<211> LENGTH: 6
<212> TYPE: PRT
```

```
<213> ORGANISM: Homo sapiens

<400> SEQUENCE: 481

Asn Arg Arg Ala Lys Trp
1               5

<210> SEQ ID NO 482
<211> LENGTH: 6
<212> TYPE: PRT
<213> ORGANISM: Homo sapiens

<400> SEQUENCE: 482

Arg Lys Arg Glu Arg Ser
1               5

<210> SEQ ID NO 483
<211> LENGTH: 6
<212> TYPE: PRT
<213> ORGANISM: Homo sapiens

<400> SEQUENCE: 483

Lys Arg Arg Gly Arg Ile
1               5

<210> SEQ ID NO 484
<211> LENGTH: 6
<212> TYPE: PRT
<213> ORGANISM: Homo sapiens

<400> SEQUENCE: 484

Lys Arg Arg Gly Arg Ile
1               5

<210> SEQ ID NO 485
<211> LENGTH: 6
<212> TYPE: PRT
<213> ORGANISM: Homo sapiens

<400> SEQUENCE: 485

Met Lys Lys Glu Lys Gly
1               5

<210> SEQ ID NO 486
<211> LENGTH: 6
<212> TYPE: PRT
<213> ORGANISM: Homo sapiens

<400> SEQUENCE: 486

Met Lys Lys Glu Lys Gly
1               5

<210> SEQ ID NO 487
<211> LENGTH: 6
<212> TYPE: PRT
<213> ORGANISM: Homo sapiens

<400> SEQUENCE: 487

Gly Arg Arg Ala Arg Pro
1               5

<210> SEQ ID NO 488
<211> LENGTH: 6
<212> TYPE: PRT
<213> ORGANISM: Homo sapiens
```

```
<400> SEQUENCE: 488

Leu Lys Lys Gln Arg Ser
1               5

<210> SEQ ID NO 489
<211> LENGTH: 6
<212> TYPE: PRT
<213> ORGANISM: Homo sapiens

<400> SEQUENCE: 489

Gly Arg Arg Ala Arg Pro
1               5

<210> SEQ ID NO 490
<211> LENGTH: 6
<212> TYPE: PRT
<213> ORGANISM: Homo sapiens

<400> SEQUENCE: 490

Leu Lys Lys Gln Arg Ser
1               5

<210> SEQ ID NO 491
<211> LENGTH: 8
<212> TYPE: PRT
<213> ORGANISM: Homo sapiens

<400> SEQUENCE: 491

Gly Lys Lys Lys Ser Thr Lys Thr
1               5

<210> SEQ ID NO 492
<211> LENGTH: 8
<212> TYPE: PRT
<213> ORGANISM: Homo sapiens

<400> SEQUENCE: 492

Ala Lys Lys Arg Gly Ser Lys Gly
1               5

<210> SEQ ID NO 493
<211> LENGTH: 6
<212> TYPE: PRT
<213> ORGANISM: Homo sapiens

<400> SEQUENCE: 493

Asn Lys Lys Gly Arg Val
1               5

<210> SEQ ID NO 494
<211> LENGTH: 6
<212> TYPE: PRT
<213> ORGANISM: Homo sapiens

<400> SEQUENCE: 494

Ala Lys Lys Ala Lys Ser
1               5

<210> SEQ ID NO 495
<211> LENGTH: 6
<212> TYPE: PRT
<213> ORGANISM: Homo sapiens

<400> SEQUENCE: 495
```

Ala Arg Lys Ser Lys Lys
1               5

<210> SEQ ID NO 496
<211> LENGTH: 6
<212> TYPE: PRT
<213> ORGANISM: Homo sapiens

<400> SEQUENCE: 496

Asp Lys Lys Leu Lys Ser
1               5

<210> SEQ ID NO 497
<211> LENGTH: 6
<212> TYPE: PRT
<213> ORGANISM: Homo sapiens

<400> SEQUENCE: 497

Asn Lys Lys Gly Arg Val
1               5

<210> SEQ ID NO 498
<211> LENGTH: 6
<212> TYPE: PRT
<213> ORGANISM: Homo sapiens

<400> SEQUENCE: 498

Ala Lys Lys Ala Lys Ser
1               5

<210> SEQ ID NO 499
<211> LENGTH: 6
<212> TYPE: PRT
<213> ORGANISM: Homo sapiens

<400> SEQUENCE: 499

Ala Arg Lys Ser Lys Lys
1               5

<210> SEQ ID NO 500
<211> LENGTH: 6
<212> TYPE: PRT
<213> ORGANISM: Homo sapiens

<400> SEQUENCE: 500

Asp Lys Lys Leu Lys Ser
1               5

<210> SEQ ID NO 501
<211> LENGTH: 8
<212> TYPE: PRT
<213> ORGANISM: Homo sapiens

<400> SEQUENCE: 501

Lys Arg Arg Arg Asn Gln Lys Leu
1               5

<210> SEQ ID NO 502
<211> LENGTH: 6
<212> TYPE: PRT
<213> ORGANISM: Homo sapiens

<400> SEQUENCE: 502

Glu Lys Arg Arg Arg Asn
1               5

```
<210> SEQ ID NO 503
<211> LENGTH: 6
<212> TYPE: PRT
<213> ORGANISM: Homo sapiens

<400> SEQUENCE: 503

Glu Lys Arg Arg Arg Asn
1               5

<210> SEQ ID NO 504
<211> LENGTH: 6
<212> TYPE: PRT
<213> ORGANISM: Homo sapiens

<400> SEQUENCE: 504

Pro Lys Lys Ala Arg Ala
1               5

<210> SEQ ID NO 505
<211> LENGTH: 6
<212> TYPE: PRT
<213> ORGANISM: Homo sapiens

<400> SEQUENCE: 505

Ala Arg Arg Ala Lys Val
1               5

<210> SEQ ID NO 506
<211> LENGTH: 6
<212> TYPE: PRT
<213> ORGANISM: Homo sapiens

<400> SEQUENCE: 506

Pro Lys Lys Ala Arg Ala
1               5

<210> SEQ ID NO 507
<211> LENGTH: 6
<212> TYPE: PRT
<213> ORGANISM: Homo sapiens

<400> SEQUENCE: 507

Ala Arg Arg Ala Lys Val
1               5

<210> SEQ ID NO 508
<211> LENGTH: 6
<212> TYPE: PRT
<213> ORGANISM: Homo sapiens

<400> SEQUENCE: 508

Leu Lys Lys Phe Lys Asp
1               5

<210> SEQ ID NO 509
<211> LENGTH: 6
<212> TYPE: PRT
<213> ORGANISM: Homo sapiens

<400> SEQUENCE: 509

Leu Lys Lys Phe Lys Asp
1               5
```

```
<210> SEQ ID NO 510
<211> LENGTH: 6
<212> TYPE: PRT
<213> ORGANISM: Homo sapiens

<400> SEQUENCE: 510

Ser Lys Arg Pro Arg Leu
1               5

<210> SEQ ID NO 511
<211> LENGTH: 6
<212> TYPE: PRT
<213> ORGANISM: Homo sapiens

<400> SEQUENCE: 511

Ala Arg Lys Gln Arg Glu
1               5

<210> SEQ ID NO 512
<211> LENGTH: 6
<212> TYPE: PRT
<213> ORGANISM: Homo sapiens

<400> SEQUENCE: 512

Arg Arg Lys Ala Lys Glu
1               5

<210> SEQ ID NO 513
<211> LENGTH: 6
<212> TYPE: PRT
<213> ORGANISM: Homo sapiens

<400> SEQUENCE: 513

Ile Arg Lys Gln Arg Glu
1               5

<210> SEQ ID NO 514
<211> LENGTH: 6
<212> TYPE: PRT
<213> ORGANISM: Homo sapiens

<400> SEQUENCE: 514

Gln Arg Arg Val Lys Phe
1               5

<210> SEQ ID NO 515
<211> LENGTH: 6
<212> TYPE: PRT
<213> ORGANISM: Homo sapiens

<400> SEQUENCE: 515

Lys Arg Arg Gly Arg Asn
1               5

<210> SEQ ID NO 516
<211> LENGTH: 6
<212> TYPE: PRT
<213> ORGANISM: Homo sapiens

<400> SEQUENCE: 516

Arg Arg Lys Gly Arg Ile
1               5

<210> SEQ ID NO 517
<211> LENGTH: 6
```

```
<212> TYPE: PRT
<213> ORGANISM: Homo sapiens

<400> SEQUENCE: 517

Ser Arg Lys Pro Arg Glu
1               5

<210> SEQ ID NO 518
<211> LENGTH: 6
<212> TYPE: PRT
<213> ORGANISM: Homo sapiens

<400> SEQUENCE: 518

Ser Arg Lys Ser Lys Ser
1               5

<210> SEQ ID NO 519
<211> LENGTH: 6
<212> TYPE: PRT
<213> ORGANISM: Homo sapiens

<400> SEQUENCE: 519

Ser Lys Arg Pro Arg Leu
1               5

<210> SEQ ID NO 520
<211> LENGTH: 6
<212> TYPE: PRT
<213> ORGANISM: Homo sapiens

<400> SEQUENCE: 520

Ala Arg Lys Gln Arg Glu
1               5

<210> SEQ ID NO 521
<211> LENGTH: 6
<212> TYPE: PRT
<213> ORGANISM: Homo sapiens

<400> SEQUENCE: 521

Arg Arg Lys Ala Lys Glu
1               5

<210> SEQ ID NO 522
<211> LENGTH: 6
<212> TYPE: PRT
<213> ORGANISM: Homo sapiens

<400> SEQUENCE: 522

Ile Arg Lys Gln Arg Glu
1               5

<210> SEQ ID NO 523
<211> LENGTH: 6
<212> TYPE: PRT
<213> ORGANISM: Homo sapiens

<400> SEQUENCE: 523

Gln Arg Arg Val Lys Phe
1               5

<210> SEQ ID NO 524
<211> LENGTH: 6
<212> TYPE: PRT
<213> ORGANISM: Homo sapiens
```

```
<400> SEQUENCE: 524

Lys Arg Arg Gly Arg Asn
1               5

<210> SEQ ID NO 525
<211> LENGTH: 6
<212> TYPE: PRT
<213> ORGANISM: Homo sapiens

<400> SEQUENCE: 525

Arg Arg Lys Gly Arg Ile
1               5

<210> SEQ ID NO 526
<211> LENGTH: 6
<212> TYPE: PRT
<213> ORGANISM: Homo sapiens

<400> SEQUENCE: 526

Ser Arg Lys Pro Arg Glu
1               5

<210> SEQ ID NO 527
<211> LENGTH: 6
<212> TYPE: PRT
<213> ORGANISM: Homo sapiens

<400> SEQUENCE: 527

Ser Arg Lys Ser Lys Ser
1               5

<210> SEQ ID NO 528
<211> LENGTH: 6
<212> TYPE: PRT
<213> ORGANISM: Homo sapiens

<400> SEQUENCE: 528

Lys Arg Arg Val Lys Ser
1               5

<210> SEQ ID NO 529
<211> LENGTH: 6
<212> TYPE: PRT
<213> ORGANISM: Homo sapiens

<400> SEQUENCE: 529

Lys Arg Arg Val Lys Ser
1               5

<210> SEQ ID NO 530
<211> LENGTH: 6
<212> TYPE: PRT
<213> ORGANISM: Homo sapiens

<400> SEQUENCE: 530

Thr Lys Lys Ile Lys Leu
1               5

<210> SEQ ID NO 531
<211> LENGTH: 6
<212> TYPE: PRT
<213> ORGANISM: Homo sapiens

<400> SEQUENCE: 531
```

```
Thr Lys Lys Ile Lys Leu
1               5

<210> SEQ ID NO 532
<211> LENGTH: 8
<212> TYPE: PRT
<213> ORGANISM: Homo sapiens

<400> SEQUENCE: 532

Phe Arg Lys Arg Met Glu Lys Glu
1               5

<210> SEQ ID NO 533
<211> LENGTH: 6
<212> TYPE: PRT
<213> ORGANISM: Homo sapiens

<400> SEQUENCE: 533

Arg Arg Lys Ala Arg Glu
1               5

<210> SEQ ID NO 534
<211> LENGTH: 6
<212> TYPE: PRT
<213> ORGANISM: Homo sapiens

<400> SEQUENCE: 534

Lys Arg Lys Leu Lys Glu
1               5

<210> SEQ ID NO 535
<211> LENGTH: 6
<212> TYPE: PRT
<213> ORGANISM: Homo sapiens

<400> SEQUENCE: 535

Lys Lys Arg Leu Arg Gln
1               5

<210> SEQ ID NO 536
<211> LENGTH: 6
<212> TYPE: PRT
<213> ORGANISM: Homo sapiens

<400> SEQUENCE: 536

Arg Arg Lys Ala Arg Glu
1               5

<210> SEQ ID NO 537
<211> LENGTH: 6
<212> TYPE: PRT
<213> ORGANISM: Homo sapiens

<400> SEQUENCE: 537

Lys Arg Lys Leu Lys Glu
1               5

<210> SEQ ID NO 538
<211> LENGTH: 6
<212> TYPE: PRT
<213> ORGANISM: Homo sapiens

<400> SEQUENCE: 538

Lys Lys Arg Leu Arg Gln
```

```
<210> SEQ ID NO 539
<211> LENGTH: 6
<212> TYPE: PRT
<213> ORGANISM: Homo sapiens

<400> SEQUENCE: 539

Ser Lys Lys Tyr Arg Gln
1               5

<210> SEQ ID NO 540
<211> LENGTH: 6
<212> TYPE: PRT
<213> ORGANISM: Homo sapiens

<400> SEQUENCE: 540

Ser Lys Lys Tyr Arg Gln
1               5

<210> SEQ ID NO 541
<211> LENGTH: 6
<212> TYPE: PRT
<213> ORGANISM: Homo sapiens

<400> SEQUENCE: 541

Val Arg Lys Phe Arg Thr
1               5

<210> SEQ ID NO 542
<211> LENGTH: 6
<212> TYPE: PRT
<213> ORGANISM: Homo sapiens

<400> SEQUENCE: 542

Gly Lys Lys Leu Lys Lys
1               5

<210> SEQ ID NO 543
<211> LENGTH: 6
<212> TYPE: PRT
<213> ORGANISM: Homo sapiens

<400> SEQUENCE: 543

Glu Lys Arg Ala Lys Tyr
1               5

<210> SEQ ID NO 544
<211> LENGTH: 6
<212> TYPE: PRT
<213> ORGANISM: Homo sapiens

<400> SEQUENCE: 544

Ser Lys Lys Tyr Lys Glu
1               5

<210> SEQ ID NO 545
<211> LENGTH: 6
<212> TYPE: PRT
<213> ORGANISM: Homo sapiens

<400> SEQUENCE: 545

Lys Lys Lys Met Lys Tyr
1               5
```

```
<210> SEQ ID NO 546
<211> LENGTH: 6
<212> TYPE: PRT
<213> ORGANISM: Homo sapiens

<400> SEQUENCE: 546

Lys Lys Arg Leu Lys Trp
1               5

<210> SEQ ID NO 547
<211> LENGTH: 6
<212> TYPE: PRT
<213> ORGANISM: Homo sapiens

<400> SEQUENCE: 547

Lys Lys Lys Ala Lys Tyr
1               5

<210> SEQ ID NO 548
<211> LENGTH: 6
<212> TYPE: PRT
<213> ORGANISM: Homo sapiens

<400> SEQUENCE: 548

Glu Lys Lys Glu Lys Leu
1               5

<210> SEQ ID NO 549
<211> LENGTH: 6
<212> TYPE: PRT
<213> ORGANISM: Homo sapiens

<400> SEQUENCE: 549

Ser Lys Lys Met Lys Phe
1               5

<210> SEQ ID NO 550
<211> LENGTH: 6
<212> TYPE: PRT
<213> ORGANISM: Homo sapiens

<400> SEQUENCE: 550

Val Arg Lys Phe Arg Thr
1               5

<210> SEQ ID NO 551
<211> LENGTH: 6
<212> TYPE: PRT
<213> ORGANISM: Homo sapiens

<400> SEQUENCE: 551

Gly Lys Lys Leu Lys Lys
1               5

<210> SEQ ID NO 552
<211> LENGTH: 6
<212> TYPE: PRT
<213> ORGANISM: Homo sapiens

<400> SEQUENCE: 552

Glu Lys Arg Ala Lys Tyr
1               5

<210> SEQ ID NO 553
```

```
<211> LENGTH: 6
<212> TYPE: PRT
<213> ORGANISM: Homo sapiens

<400> SEQUENCE: 553

Ser Lys Lys Tyr Lys Glu
1               5

<210> SEQ ID NO 554
<211> LENGTH: 6
<212> TYPE: PRT
<213> ORGANISM: Homo sapiens

<400> SEQUENCE: 554

Lys Lys Lys Met Lys Tyr
1               5

<210> SEQ ID NO 555
<211> LENGTH: 6
<212> TYPE: PRT
<213> ORGANISM: Homo sapiens

<400> SEQUENCE: 555

Lys Lys Arg Leu Lys Trp
1               5

<210> SEQ ID NO 556
<211> LENGTH: 6
<212> TYPE: PRT
<213> ORGANISM: Homo sapiens

<400> SEQUENCE: 556

Lys Lys Lys Ala Lys Tyr
1               5

<210> SEQ ID NO 557
<211> LENGTH: 6
<212> TYPE: PRT
<213> ORGANISM: Homo sapiens

<400> SEQUENCE: 557

Glu Lys Lys Glu Lys Leu
1               5

<210> SEQ ID NO 558
<211> LENGTH: 6
<212> TYPE: PRT
<213> ORGANISM: Homo sapiens

<400> SEQUENCE: 558

Ser Lys Lys Met Lys Phe
1               5

<210> SEQ ID NO 559
<211> LENGTH: 8
<212> TYPE: PRT
<213> ORGANISM: Homo sapiens

<400> SEQUENCE: 559

Phe Arg Arg Arg Gly Ala Arg Ala
1               5

<210> SEQ ID NO 560
<211> LENGTH: 8
<212> TYPE: PRT
```

```
<213> ORGANISM: Homo sapiens

<400> SEQUENCE: 560

Gln Lys Arg Arg Tyr Ser Lys Gly
1               5

<210> SEQ ID NO 561
<211> LENGTH: 8
<212> TYPE: PRT
<213> ORGANISM: Homo sapiens

<400> SEQUENCE: 561

Tyr Arg Lys Lys Pro His Arg Pro
1               5

<210> SEQ ID NO 562
<211> LENGTH: 6
<212> TYPE: PRT
<213> ORGANISM: Homo sapiens

<400> SEQUENCE: 562

Glu Arg Arg Leu Lys Met
1               5

<210> SEQ ID NO 563
<211> LENGTH: 6
<212> TYPE: PRT
<213> ORGANISM: Homo sapiens

<400> SEQUENCE: 563

Glu Arg Arg Leu Lys Met
1               5

<210> SEQ ID NO 564
<211> LENGTH: 6
<212> TYPE: PRT
<213> ORGANISM: Homo sapiens

<400> SEQUENCE: 564

Asp Arg Lys Val Lys Ser
1               5

<210> SEQ ID NO 565
<211> LENGTH: 6
<212> TYPE: PRT
<213> ORGANISM: Homo sapiens

<400> SEQUENCE: 565

Ile Lys Arg Lys Arg Glu
1               5

<210> SEQ ID NO 566
<211> LENGTH: 6
<212> TYPE: PRT
<213> ORGANISM: Homo sapiens

<400> SEQUENCE: 566

Asp Arg Lys Val Lys Ser
1               5

<210> SEQ ID NO 567
<211> LENGTH: 6
<212> TYPE: PRT
<213> ORGANISM: Homo sapiens
```

```
<400> SEQUENCE: 567

Ile Lys Arg Lys Arg Glu
1               5

<210> SEQ ID NO 568
<211> LENGTH: 6
<212> TYPE: PRT
<213> ORGANISM: Homo sapiens

<400> SEQUENCE: 568

Ser Lys Lys Gly Arg Lys
1               5

<210> SEQ ID NO 569
<211> LENGTH: 6
<212> TYPE: PRT
<213> ORGANISM: Homo sapiens

<400> SEQUENCE: 569

Ser Lys Lys Gly Arg Lys
1               5

<210> SEQ ID NO 570
<211> LENGTH: 6
<212> TYPE: PRT
<213> ORGANISM: Homo sapiens

<400> SEQUENCE: 570

His Arg Arg Pro Arg Gly
1               5

<210> SEQ ID NO 571
<211> LENGTH: 6
<212> TYPE: PRT
<213> ORGANISM: Homo sapiens

<400> SEQUENCE: 571

His Arg Arg Pro Arg Gly
1               5

<210> SEQ ID NO 572
<211> LENGTH: 6
<212> TYPE: PRT
<213> ORGANISM: Homo sapiens

<400> SEQUENCE: 572

Ala Arg Arg Pro Arg His
1               5

<210> SEQ ID NO 573
<211> LENGTH: 6
<212> TYPE: PRT
<213> ORGANISM: Homo sapiens

<400> SEQUENCE: 573

Glu Lys Arg Ile Lys Glu
1               5

<210> SEQ ID NO 574
<211> LENGTH: 6
<212> TYPE: PRT
<213> ORGANISM: Homo sapiens

<400> SEQUENCE: 574
```

```
Leu Lys Lys Ile Lys Gln
1               5

<210> SEQ ID NO 575
<211> LENGTH: 6
<212> TYPE: PRT
<213> ORGANISM: Homo sapiens

<400> SEQUENCE: 575

Ala Arg Arg Pro Arg His
1               5

<210> SEQ ID NO 576
<211> LENGTH: 6
<212> TYPE: PRT
<213> ORGANISM: Homo sapiens

<400> SEQUENCE: 576

Glu Lys Arg Ile Lys Glu
1               5

<210> SEQ ID NO 577
<211> LENGTH: 6
<212> TYPE: PRT
<213> ORGANISM: Homo sapiens

<400> SEQUENCE: 577

Leu Lys Lys Ile Lys Gln
1               5

<210> SEQ ID NO 578
<211> LENGTH: 6
<212> TYPE: PRT
<213> ORGANISM: Homo sapiens

<400> SEQUENCE: 578

Arg Arg Lys Pro Lys Pro
1               5

<210> SEQ ID NO 579
<211> LENGTH: 6
<212> TYPE: PRT
<213> ORGANISM: Homo sapiens

<400> SEQUENCE: 579

Arg Arg Lys Pro Lys Pro
1               5

<210> SEQ ID NO 580
<211> LENGTH: 6
<212> TYPE: PRT
<213> ORGANISM: Homo sapiens

<400> SEQUENCE: 580

Ala Arg Arg Lys Lys Ile
1               5

<210> SEQ ID NO 581
<211> LENGTH: 6
<212> TYPE: PRT
<213> ORGANISM: Homo sapiens

<400> SEQUENCE: 581

Ala Arg Arg Lys Lys Ile
1               5
```

<210> SEQ ID NO 582
<211> LENGTH: 6
<212> TYPE: PRT
<213> ORGANISM: Homo sapiens

<400> SEQUENCE: 582

Ala Arg Arg Lys Arg Gln
1               5

<210> SEQ ID NO 583
<211> LENGTH: 6
<212> TYPE: PRT
<213> ORGANISM: Homo sapiens

<400> SEQUENCE: 583

Gln Lys Arg Leu Lys Lys
1               5

<210> SEQ ID NO 584
<211> LENGTH: 6
<212> TYPE: PRT
<213> ORGANISM: Homo sapiens

<400> SEQUENCE: 584

Glu Lys Lys Thr Lys Arg
1               5

<210> SEQ ID NO 585
<211> LENGTH: 6
<212> TYPE: PRT
<213> ORGANISM: Homo sapiens

<400> SEQUENCE: 585

Ala Arg Arg Lys Arg Gln
1               5

<210> SEQ ID NO 586
<211> LENGTH: 6
<212> TYPE: PRT
<213> ORGANISM: Homo sapiens

<400> SEQUENCE: 586

Gln Lys Arg Leu Lys Lys
1               5

<210> SEQ ID NO 587
<211> LENGTH: 6
<212> TYPE: PRT
<213> ORGANISM: Homo sapiens

<400> SEQUENCE: 587

Glu Lys Lys Thr Lys Arg
1               5

<210> SEQ ID NO 588
<211> LENGTH: 8
<212> TYPE: PRT
<213> ORGANISM: Homo sapiens

<400> SEQUENCE: 588

Glu Lys Arg Lys Ser Glu Lys Ala
1               5

```
<210> SEQ ID NO 589
<211> LENGTH: 6
<212> TYPE: PRT
<213> ORGANISM: Homo sapiens

<400> SEQUENCE: 589

Thr Arg Lys Lys Arg Lys
1               5

<210> SEQ ID NO 590
<211> LENGTH: 6
<212> TYPE: PRT
<213> ORGANISM: Homo sapiens

<400> SEQUENCE: 590

Thr Arg Lys Lys Arg Lys
1               5

<210> SEQ ID NO 591
<211> LENGTH: 6
<212> TYPE: PRT
<213> ORGANISM: Homo sapiens

<400> SEQUENCE: 591

Ala Arg Lys Leu Lys Lys
1               5

<210> SEQ ID NO 592
<211> LENGTH: 6
<212> TYPE: PRT
<213> ORGANISM: Homo sapiens

<400> SEQUENCE: 592

Ala Arg Lys Leu Lys Lys
1               5

<210> SEQ ID NO 593
<211> LENGTH: 8
<212> TYPE: PRT
<213> ORGANISM: Homo sapiens

<400> SEQUENCE: 593

Arg Lys Arg Arg Pro Ser Arg Pro
1               5

<210> SEQ ID NO 594
<211> LENGTH: 6
<212> TYPE: PRT
<213> ORGANISM: Homo sapiens

<400> SEQUENCE: 594

Asn Lys Lys Lys Lys Glu
1               5

<210> SEQ ID NO 595
<211> LENGTH: 6
<212> TYPE: PRT
<213> ORGANISM: Homo sapiens

<400> SEQUENCE: 595

Val Arg Lys Arg Arg Pro
1               5

<210> SEQ ID NO 596
<211> LENGTH: 6
```

```
<212> TYPE: PRT
<213> ORGANISM: Homo sapiens

<400> SEQUENCE: 596

Asn Lys Lys Lys Lys Glu
1               5

<210> SEQ ID NO 597
<211> LENGTH: 6
<212> TYPE: PRT
<213> ORGANISM: Homo sapiens

<400> SEQUENCE: 597

Val Arg Lys Arg Arg Pro
1               5

<210> SEQ ID NO 598
<211> LENGTH: 8
<212> TYPE: PRT
<213> ORGANISM: Homo sapiens

<400> SEQUENCE: 598

Trp Lys Lys Lys Tyr Glu Lys Glu
1               5

<210> SEQ ID NO 599
<211> LENGTH: 6
<212> TYPE: PRT
<213> ORGANISM: Homo sapiens

<400> SEQUENCE: 599

Val Lys Arg Cys Lys Gln
1               5

<210> SEQ ID NO 600
<211> LENGTH: 6
<212> TYPE: PRT
<213> ORGANISM: Homo sapiens

<400> SEQUENCE: 600

Glu Lys Arg Leu Arg Ala
1               5

<210> SEQ ID NO 601
<211> LENGTH: 6
<212> TYPE: PRT
<213> ORGANISM: Homo sapiens

<400> SEQUENCE: 601

Val Lys Arg Cys Lys Gln
1               5

<210> SEQ ID NO 602
<211> LENGTH: 6
<212> TYPE: PRT
<213> ORGANISM: Homo sapiens

<400> SEQUENCE: 602

Glu Lys Arg Leu Arg Ala
1               5

<210> SEQ ID NO 603
<211> LENGTH: 6
<212> TYPE: PRT
<213> ORGANISM: Homo sapiens
```

```
<400> SEQUENCE: 603

Val Lys Lys Ile Lys Glu
1               5

<210> SEQ ID NO 604
<211> LENGTH: 6
<212> TYPE: PRT
<213> ORGANISM: Homo sapiens

<400> SEQUENCE: 604

Val Lys Lys Ile Lys Glu
1               5

<210> SEQ ID NO 605
<211> LENGTH: 6
<212> TYPE: PRT
<213> ORGANISM: Homo sapiens

<400> SEQUENCE: 605

Asn Lys Lys Phe Lys Met
1               5

<210> SEQ ID NO 606
<211> LENGTH: 6
<212> TYPE: PRT
<213> ORGANISM: Homo sapiens

<400> SEQUENCE: 606

Glu Arg Arg His Arg Leu
1               5

<210> SEQ ID NO 607
<211> LENGTH: 6
<212> TYPE: PRT
<213> ORGANISM: Homo sapiens

<400> SEQUENCE: 607

Asn Lys Lys Phe Lys Met
1               5

<210> SEQ ID NO 608
<211> LENGTH: 6
<212> TYPE: PRT
<213> ORGANISM: Homo sapiens

<400> SEQUENCE: 608

Glu Arg Arg His Arg Leu
1               5

<210> SEQ ID NO 609
<211> LENGTH: 6
<212> TYPE: PRT
<213> ORGANISM: Homo sapiens

<400> SEQUENCE: 609

Ser Arg Arg Pro Arg Phe
1               5

<210> SEQ ID NO 610
<211> LENGTH: 6
<212> TYPE: PRT
<213> ORGANISM: Homo sapiens

<400> SEQUENCE: 610
```

Ser Arg Arg Pro Arg Phe
1               5

<210> SEQ ID NO 611
<211> LENGTH: 8
<212> TYPE: PRT
<213> ORGANISM: Homo sapiens

<400> SEQUENCE: 611

Thr Lys Arg Lys Lys Pro Arg Arg
1               5

<210> SEQ ID NO 612
<211> LENGTH: 6
<212> TYPE: PRT
<213> ORGANISM: Homo sapiens

<400> SEQUENCE: 612

Pro Lys Lys Asp Lys Leu
1               5

<210> SEQ ID NO 613
<211> LENGTH: 6
<212> TYPE: PRT
<213> ORGANISM: Homo sapiens

<400> SEQUENCE: 613

Thr Lys Arg Lys Lys Pro
1               5

<210> SEQ ID NO 614
<211> LENGTH: 6
<212> TYPE: PRT
<213> ORGANISM: Homo sapiens

<400> SEQUENCE: 614

Asn Lys Lys Asn Arg Glu
1               5

<210> SEQ ID NO 615
<211> LENGTH: 6
<212> TYPE: PRT
<213> ORGANISM: Homo sapiens

<400> SEQUENCE: 615

Leu Lys Lys Ser Arg Ile
1               5

<210> SEQ ID NO 616
<211> LENGTH: 6
<212> TYPE: PRT
<213> ORGANISM: Homo sapiens

<400> SEQUENCE: 616

Pro Lys Lys Pro Arg Glu
1               5

<210> SEQ ID NO 617
<211> LENGTH: 6
<212> TYPE: PRT
<213> ORGANISM: Homo sapiens

<400> SEQUENCE: 617

Ser Arg Lys Gln Arg Gln

<210> SEQ ID NO 618
<211> LENGTH: 6
<212> TYPE: PRT
<213> ORGANISM: Homo sapiens

<400> SEQUENCE: 618

Val Lys Arg Lys Arg Lys
1               5

<210> SEQ ID NO 619
<211> LENGTH: 6
<212> TYPE: PRT
<213> ORGANISM: Homo sapiens

<400> SEQUENCE: 619

Pro Lys Lys Asp Lys Leu
1               5

<210> SEQ ID NO 620
<211> LENGTH: 6
<212> TYPE: PRT
<213> ORGANISM: Homo sapiens

<400> SEQUENCE: 620

Thr Lys Arg Lys Lys Pro
1               5

<210> SEQ ID NO 621
<211> LENGTH: 6
<212> TYPE: PRT
<213> ORGANISM: Homo sapiens

<400> SEQUENCE: 621

Asn Lys Lys Asn Arg Glu
1               5

<210> SEQ ID NO 622
<211> LENGTH: 6
<212> TYPE: PRT
<213> ORGANISM: Homo sapiens

<400> SEQUENCE: 622

Leu Lys Lys Ser Arg Ile
1               5

<210> SEQ ID NO 623
<211> LENGTH: 6
<212> TYPE: PRT
<213> ORGANISM: Homo sapiens

<400> SEQUENCE: 623

Pro Lys Lys Pro Arg Glu
1               5

<210> SEQ ID NO 624
<211> LENGTH: 6
<212> TYPE: PRT
<213> ORGANISM: Homo sapiens

<400> SEQUENCE: 624

Ser Arg Lys Gln Arg Gln
1               5

```
<210> SEQ ID NO 625
<211> LENGTH: 6
<212> TYPE: PRT
<213> ORGANISM: Homo sapiens

<400> SEQUENCE: 625

Val Lys Arg Lys Arg Lys
1               5

<210> SEQ ID NO 626
<211> LENGTH: 6
<212> TYPE: PRT
<213> ORGANISM: Homo sapiens

<400> SEQUENCE: 626

Ala Arg Arg Leu Arg Arg
1               5

<210> SEQ ID NO 627
<211> LENGTH: 6
<212> TYPE: PRT
<213> ORGANISM: Homo sapiens

<400> SEQUENCE: 627

Pro Arg Arg Cys Lys Trp
1               5

<210> SEQ ID NO 628
<211> LENGTH: 6
<212> TYPE: PRT
<213> ORGANISM: Homo sapiens

<400> SEQUENCE: 628

Ala Arg Arg Leu Arg Arg
1               5

<210> SEQ ID NO 629
<211> LENGTH: 6
<212> TYPE: PRT
<213> ORGANISM: Homo sapiens

<400> SEQUENCE: 629

Pro Arg Arg Cys Lys Trp
1               5

<210> SEQ ID NO 630
<211> LENGTH: 6
<212> TYPE: PRT
<213> ORGANISM: Homo sapiens

<400> SEQUENCE: 630

Met Lys Lys Pro Arg Phe
1               5

<210> SEQ ID NO 631
<211> LENGTH: 6
<212> TYPE: PRT
<213> ORGANISM: Homo sapiens

<400> SEQUENCE: 631

Met Lys Lys Pro Arg Phe
1               5

<210> SEQ ID NO 632
```

```
<211> LENGTH: 6
<212> TYPE: PRT
<213> ORGANISM: Homo sapiens

<400> SEQUENCE: 632

Arg Arg Arg Gln Arg Ala
1               5

<210> SEQ ID NO 633
<211> LENGTH: 6
<212> TYPE: PRT
<213> ORGANISM: Homo sapiens

<400> SEQUENCE: 633

Pro Arg Arg Ile Arg Lys
1               5

<210> SEQ ID NO 634
<211> LENGTH: 6
<212> TYPE: PRT
<213> ORGANISM: Homo sapiens

<400> SEQUENCE: 634

Ala Arg Arg Thr Arg Thr
1               5

<210> SEQ ID NO 635
<211> LENGTH: 6
<212> TYPE: PRT
<213> ORGANISM: Homo sapiens

<400> SEQUENCE: 635

Arg Arg Arg Gln Arg Ala
1               5

<210> SEQ ID NO 636
<211> LENGTH: 6
<212> TYPE: PRT
<213> ORGANISM: Homo sapiens

<400> SEQUENCE: 636

Pro Arg Arg Ile Arg Lys
1               5

<210> SEQ ID NO 637
<211> LENGTH: 6
<212> TYPE: PRT
<213> ORGANISM: Homo sapiens

<400> SEQUENCE: 637

Ala Arg Arg Thr Arg Thr
1               5

<210> SEQ ID NO 638
<211> LENGTH: 6
<212> TYPE: PRT
<213> ORGANISM: Homo sapiens

<400> SEQUENCE: 638

Gln Lys Arg Gly Arg Val
1               5

<210> SEQ ID NO 639
<211> LENGTH: 6
<212> TYPE: PRT
```

```
<213> ORGANISM: Homo sapiens

<400> SEQUENCE: 639

Gln Lys Arg Gly Arg Val
1               5

<210> SEQ ID NO 640
<211> LENGTH: 6
<212> TYPE: PRT
<213> ORGANISM: Homo sapiens

<400> SEQUENCE: 640

Ser Arg Arg Ser Lys Leu
1               5

<210> SEQ ID NO 641
<211> LENGTH: 6
<212> TYPE: PRT
<213> ORGANISM: Homo sapiens

<400> SEQUENCE: 641

Pro Lys Lys Ala Lys Ser
1               5

<210> SEQ ID NO 642
<211> LENGTH: 6
<212> TYPE: PRT
<213> ORGANISM: Homo sapiens

<400> SEQUENCE: 642

Ser Arg Arg Ser Lys Leu
1               5

<210> SEQ ID NO 643
<211> LENGTH: 6
<212> TYPE: PRT
<213> ORGANISM: Homo sapiens

<400> SEQUENCE: 643

Pro Lys Lys Ala Lys Ser
1               5

<210> SEQ ID NO 644
<211> LENGTH: 6
<212> TYPE: PRT
<213> ORGANISM: Homo sapiens

<400> SEQUENCE: 644

Glu Lys Arg Asn Arg Lys
1               5

<210> SEQ ID NO 645
<211> LENGTH: 6
<212> TYPE: PRT
<213> ORGANISM: Homo sapiens

<400> SEQUENCE: 645

Glu Lys Arg Asn Arg Lys
1               5

<210> SEQ ID NO 646
<211> LENGTH: 6
<212> TYPE: PRT
<213> ORGANISM: Homo sapiens
```

-continued

```
<400> SEQUENCE: 646

Gly Arg Arg Tyr Arg Arg
1               5

<210> SEQ ID NO 647
<211> LENGTH: 6
<212> TYPE: PRT
<213> ORGANISM: Homo sapiens

<400> SEQUENCE: 647

Pro Arg Lys Asn Lys Glu
1               5

<210> SEQ ID NO 648
<211> LENGTH: 6
<212> TYPE: PRT
<213> ORGANISM: Homo sapiens

<400> SEQUENCE: 648

Gly Arg Arg Tyr Arg Arg
1               5

<210> SEQ ID NO 649
<211> LENGTH: 6
<212> TYPE: PRT
<213> ORGANISM: Homo sapiens

<400> SEQUENCE: 649

Pro Arg Lys Asn Lys Glu
1               5

<210> SEQ ID NO 650
<211> LENGTH: 8
<212> TYPE: PRT
<213> ORGANISM: Homo sapiens

<400> SEQUENCE: 650

Lys Arg Arg Lys His Leu Lys Arg
1               5

<210> SEQ ID NO 651
<211> LENGTH: 6
<212> TYPE: PRT
<213> ORGANISM: Homo sapiens

<400> SEQUENCE: 651

Trp Lys Arg Arg Lys His
1               5

<210> SEQ ID NO 652
<211> LENGTH: 6
<212> TYPE: PRT
<213> ORGANISM: Homo sapiens

<400> SEQUENCE: 652

Leu Lys Arg Ser Arg Asp
1               5

<210> SEQ ID NO 653
<211> LENGTH: 6
<212> TYPE: PRT
<213> ORGANISM: Homo sapiens

<400> SEQUENCE: 653
```

```
Gly Arg Lys Leu Arg Leu
1               5

<210> SEQ ID NO 654
<211> LENGTH: 6
<212> TYPE: PRT
<213> ORGANISM: Homo sapiens

<400> SEQUENCE: 654

Ser Arg Lys Arg Lys Leu
1               5

<210> SEQ ID NO 655
<211> LENGTH: 6
<212> TYPE: PRT
<213> ORGANISM: Homo sapiens

<400> SEQUENCE: 655

Trp Lys Arg Arg Lys His
1               5

<210> SEQ ID NO 656
<211> LENGTH: 6
<212> TYPE: PRT
<213> ORGANISM: Homo sapiens

<400> SEQUENCE: 656

Leu Lys Arg Ser Arg Asp
1               5

<210> SEQ ID NO 657
<211> LENGTH: 6
<212> TYPE: PRT
<213> ORGANISM: Homo sapiens

<400> SEQUENCE: 657

Gly Arg Lys Leu Arg Leu
1               5

<210> SEQ ID NO 658
<211> LENGTH: 6
<212> TYPE: PRT
<213> ORGANISM: Homo sapiens

<400> SEQUENCE: 658

Ser Arg Lys Arg Lys Leu
1               5

<210> SEQ ID NO 659
<211> LENGTH: 8
<212> TYPE: PRT
<213> ORGANISM: Homo sapiens

<400> SEQUENCE: 659

Met Arg Arg Arg Gln Arg Arg Glu
1               5

<210> SEQ ID NO 660
<211> LENGTH: 6
<212> TYPE: PRT
<213> ORGANISM: Homo sapiens

<400> SEQUENCE: 660

Glu Lys Arg Thr Arg Leu
1               5
```

```
<210> SEQ ID NO 661
<211> LENGTH: 6
<212> TYPE: PRT
<213> ORGANISM: Homo sapiens

<400> SEQUENCE: 661

Arg Arg Arg Gln Arg Arg
1               5

<210> SEQ ID NO 662
<211> LENGTH: 6
<212> TYPE: PRT
<213> ORGANISM: Homo sapiens

<400> SEQUENCE: 662

Asn Arg Arg Cys Lys Leu
1               5

<210> SEQ ID NO 663
<211> LENGTH: 6
<212> TYPE: PRT
<213> ORGANISM: Homo sapiens

<400> SEQUENCE: 663

Glu Lys Arg Thr Arg Leu
1               5

<210> SEQ ID NO 664
<211> LENGTH: 6
<212> TYPE: PRT
<213> ORGANISM: Homo sapiens

<400> SEQUENCE: 664

Arg Arg Arg Gln Arg Arg
1               5

<210> SEQ ID NO 665
<211> LENGTH: 6
<212> TYPE: PRT
<213> ORGANISM: Homo sapiens

<400> SEQUENCE: 665

Asn Arg Arg Cys Lys Leu
1               5

<210> SEQ ID NO 666
<211> LENGTH: 6
<212> TYPE: PRT
<213> ORGANISM: Homo sapiens

<400> SEQUENCE: 666

Ala Lys Lys Tyr Arg Asp
1               5

<210> SEQ ID NO 667
<211> LENGTH: 6
<212> TYPE: PRT
<213> ORGANISM: Homo sapiens

<400> SEQUENCE: 667

Ala Lys Lys Tyr Arg Asp
1               5
```

-continued

```
<210> SEQ ID NO 668
<211> LENGTH: 8
<212> TYPE: PRT
<213> ORGANISM: Homo sapiens

<400> SEQUENCE: 668

Lys Arg Lys Lys Pro Ser Arg Pro
1               5

<210> SEQ ID NO 669
<211> LENGTH: 6
<212> TYPE: PRT
<213> ORGANISM: Homo sapiens

<400> SEQUENCE: 669

Ser Lys Lys Arg Lys Lys
1               5

<210> SEQ ID NO 670
<211> LENGTH: 6
<212> TYPE: PRT
<213> ORGANISM: Homo sapiens

<400> SEQUENCE: 670

Gln Lys Arg Gln Lys Cys
1               5

<210> SEQ ID NO 671
<211> LENGTH: 6
<212> TYPE: PRT
<213> ORGANISM: Homo sapiens

<400> SEQUENCE: 671

Tyr Arg Arg Arg Lys Arg
1               5

<210> SEQ ID NO 672
<211> LENGTH: 6
<212> TYPE: PRT
<213> ORGANISM: Homo sapiens

<400> SEQUENCE: 672

Ser Lys Lys Arg Lys Lys
1               5

<210> SEQ ID NO 673
<211> LENGTH: 6
<212> TYPE: PRT
<213> ORGANISM: Homo sapiens

<400> SEQUENCE: 673

Gln Lys Arg Gln Lys Cys
1               5

<210> SEQ ID NO 674
<211> LENGTH: 6
<212> TYPE: PRT
<213> ORGANISM: Homo sapiens

<400> SEQUENCE: 674

Tyr Arg Arg Arg Lys Arg
1               5

<210> SEQ ID NO 675
<211> LENGTH: 6
```

```
<212> TYPE: PRT
<213> ORGANISM: Homo sapiens

<400> SEQUENCE: 675

Arg Lys Arg Gln Arg Ala
1               5

<210> SEQ ID NO 676
<211> LENGTH: 6
<212> TYPE: PRT
<213> ORGANISM: Homo sapiens

<400> SEQUENCE: 676

Arg Lys Arg Gln Arg Ala
1               5

<210> SEQ ID NO 677
<211> LENGTH: 6
<212> TYPE: PRT
<213> ORGANISM: Homo sapiens

<400> SEQUENCE: 677

Leu Lys Lys Asp Arg Glu
1               5

<210> SEQ ID NO 678
<211> LENGTH: 6
<212> TYPE: PRT
<213> ORGANISM: Homo sapiens

<400> SEQUENCE: 678

Leu Lys Lys His Lys Glu
1               5

<210> SEQ ID NO 679
<211> LENGTH: 6
<212> TYPE: PRT
<213> ORGANISM: Homo sapiens

<400> SEQUENCE: 679

Leu Lys Lys Asp Arg Glu
1               5

<210> SEQ ID NO 680
<211> LENGTH: 6
<212> TYPE: PRT
<213> ORGANISM: Homo sapiens

<400> SEQUENCE: 680

Leu Lys Lys His Lys Glu
1               5

<210> SEQ ID NO 681
<211> LENGTH: 6
<212> TYPE: PRT
<213> ORGANISM: Homo sapiens

<400> SEQUENCE: 681

Ser Arg Arg Thr Arg Trp
1               5

<210> SEQ ID NO 682
<211> LENGTH: 6
<212> TYPE: PRT
<213> ORGANISM: Homo sapiens
```

```
<400> SEQUENCE: 682

Glu Arg Arg Arg Lys Phe
1               5

<210> SEQ ID NO 683
<211> LENGTH: 6
<212> TYPE: PRT
<213> ORGANISM: Homo sapiens

<400> SEQUENCE: 683

Leu Arg Arg Cys Arg Ala
1               5

<210> SEQ ID NO 684
<211> LENGTH: 6
<212> TYPE: PRT
<213> ORGANISM: Homo sapiens

<400> SEQUENCE: 684

Ser Arg Arg Ser Arg Ser
1               5

<210> SEQ ID NO 685
<211> LENGTH: 6
<212> TYPE: PRT
<213> ORGANISM: Homo sapiens

<400> SEQUENCE: 685

Gly Arg Arg Arg Lys Ser
1               5

<210> SEQ ID NO 686
<211> LENGTH: 6
<212> TYPE: PRT
<213> ORGANISM: Homo sapiens

<400> SEQUENCE: 686

Glu Arg Arg Ala Lys Gln
1               5

<210> SEQ ID NO 687
<211> LENGTH: 6
<212> TYPE: PRT
<213> ORGANISM: Homo sapiens

<400> SEQUENCE: 687

Ser Arg Arg Thr Arg Trp
1               5

<210> SEQ ID NO 688
<211> LENGTH: 6
<212> TYPE: PRT
<213> ORGANISM: Homo sapiens

<400> SEQUENCE: 688

Glu Arg Arg Arg Lys Phe
1               5

<210> SEQ ID NO 689
<211> LENGTH: 6
<212> TYPE: PRT
<213> ORGANISM: Homo sapiens

<400> SEQUENCE: 689
```

```
Leu Arg Arg Cys Arg Ala
1               5

<210> SEQ ID NO 690
<211> LENGTH: 6
<212> TYPE: PRT
<213> ORGANISM: Homo sapiens

<400> SEQUENCE: 690

Ser Arg Arg Ser Arg Ser
1               5

<210> SEQ ID NO 691
<211> LENGTH: 6
<212> TYPE: PRT
<213> ORGANISM: Homo sapiens

<400> SEQUENCE: 691

Gly Arg Arg Arg Lys Ser
1               5

<210> SEQ ID NO 692
<211> LENGTH: 6
<212> TYPE: PRT
<213> ORGANISM: Homo sapiens

<400> SEQUENCE: 692

Glu Arg Arg Ala Lys Gln
1               5

<210> SEQ ID NO 693
<211> LENGTH: 8
<212> TYPE: PRT
<213> ORGANISM: Homo sapiens

<400> SEQUENCE: 693

Leu Arg Arg Arg Arg Val Lys Arg
1               5

<210> SEQ ID NO 694
<211> LENGTH: 6
<212> TYPE: PRT
<213> ORGANISM: Homo sapiens

<400> SEQUENCE: 694

Leu Arg Arg Arg Arg Val
1               5

<210> SEQ ID NO 695
<211> LENGTH: 6
<212> TYPE: PRT
<213> ORGANISM: Homo sapiens

<400> SEQUENCE: 695

Glu Lys Arg Gly Lys Gly
1               5

<210> SEQ ID NO 696
<211> LENGTH: 6
<212> TYPE: PRT
<213> ORGANISM: Homo sapiens

<400> SEQUENCE: 696

Leu Arg Arg Arg Arg Val
```

-continued

```
<210> SEQ ID NO 697
<211> LENGTH: 6
<212> TYPE: PRT
<213> ORGANISM: Homo sapiens

<400> SEQUENCE: 697

Glu Lys Arg Gly Lys Gly
1               5

<210> SEQ ID NO 698
<211> LENGTH: 6
<212> TYPE: PRT
<213> ORGANISM: Homo sapiens

<400> SEQUENCE: 698

Asn Arg Arg Leu Lys His
1               5

<210> SEQ ID NO 699
<211> LENGTH: 6
<212> TYPE: PRT
<213> ORGANISM: Homo sapiens

<400> SEQUENCE: 699

Asn Arg Arg Leu Lys His
1               5

<210> SEQ ID NO 700
<211> LENGTH: 6
<212> TYPE: PRT
<213> ORGANISM: Homo sapiens

<400> SEQUENCE: 700

Lys Arg Arg Tyr Arg Gly
1               5

<210> SEQ ID NO 701
<211> LENGTH: 6
<212> TYPE: PRT
<213> ORGANISM: Homo sapiens

<400> SEQUENCE: 701

Lys Arg Arg Tyr Arg Gly
1               5

<210> SEQ ID NO 702
<211> LENGTH: 6
<212> TYPE: PRT
<213> ORGANISM: Homo sapiens

<400> SEQUENCE: 702

Ala Arg Arg Gln Arg Asp
1               5

<210> SEQ ID NO 703
<211> LENGTH: 6
<212> TYPE: PRT
<213> ORGANISM: Homo sapiens

<400> SEQUENCE: 703

Pro Lys Lys Pro Lys Thr
1               5
```

```
<210> SEQ ID NO 704
<211> LENGTH: 6
<212> TYPE: PRT
<213> ORGANISM: Homo sapiens

<400> SEQUENCE: 704

Asn Arg Arg Ser Arg Asn
1               5

<210> SEQ ID NO 705
<211> LENGTH: 6
<212> TYPE: PRT
<213> ORGANISM: Homo sapiens

<400> SEQUENCE: 705

Glu Lys Arg Asp Lys Glu
1               5

<210> SEQ ID NO 706
<211> LENGTH: 6
<212> TYPE: PRT
<213> ORGANISM: Homo sapiens

<400> SEQUENCE: 706

Ala Arg Arg Gln Arg Asp
1               5

<210> SEQ ID NO 707
<211> LENGTH: 6
<212> TYPE: PRT
<213> ORGANISM: Homo sapiens

<400> SEQUENCE: 707

Pro Lys Lys Pro Lys Thr
1               5

<210> SEQ ID NO 708
<211> LENGTH: 6
<212> TYPE: PRT
<213> ORGANISM: Homo sapiens

<400> SEQUENCE: 708

Asn Arg Arg Ser Arg Asn
1               5

<210> SEQ ID NO 709
<211> LENGTH: 6
<212> TYPE: PRT
<213> ORGANISM: Homo sapiens

<400> SEQUENCE: 709

Glu Lys Arg Asp Lys Glu
1               5

<210> SEQ ID NO 710
<211> LENGTH: 6
<212> TYPE: PRT
<213> ORGANISM: Homo sapiens

<400> SEQUENCE: 710

Gly Lys Lys Leu Lys Ala
1               5

<210> SEQ ID NO 711
```

```
<211> LENGTH: 6
<212> TYPE: PRT
<213> ORGANISM: Homo sapiens

<400> SEQUENCE: 711

Lys Arg Lys Glu Lys Leu
1               5

<210> SEQ ID NO 712
<211> LENGTH: 6
<212> TYPE: PRT
<213> ORGANISM: Homo sapiens

<400> SEQUENCE: 712

Gly Lys Lys Leu Lys Ala
1               5

<210> SEQ ID NO 713
<211> LENGTH: 6
<212> TYPE: PRT
<213> ORGANISM: Homo sapiens

<400> SEQUENCE: 713

Lys Arg Lys Glu Lys Leu
1               5

<210> SEQ ID NO 714
<211> LENGTH: 6
<212> TYPE: PRT
<213> ORGANISM: Homo sapiens

<400> SEQUENCE: 714

Ala Lys Lys His Lys Arg
1               5

<210> SEQ ID NO 715
<211> LENGTH: 6
<212> TYPE: PRT
<213> ORGANISM: Homo sapiens

<400> SEQUENCE: 715

Ala Lys Lys His Lys Arg
1               5

<210> SEQ ID NO 716
<211> LENGTH: 6
<212> TYPE: PRT
<213> ORGANISM: Homo sapiens

<400> SEQUENCE: 716

Lys Arg Lys Met Lys Ala
1               5

<210> SEQ ID NO 717
<211> LENGTH: 6
<212> TYPE: PRT
<213> ORGANISM: Homo sapiens

<400> SEQUENCE: 717

Lys Arg Lys Met Lys Ala
1               5

<210> SEQ ID NO 718
<211> LENGTH: 8
<212> TYPE: PRT
```

```
<213> ORGANISM: Homo sapiens

<400> SEQUENCE: 718

Lys Lys Lys Arg Lys Gln Arg Arg
1               5

<210> SEQ ID NO 719
<211> LENGTH: 6
<212> TYPE: PRT
<213> ORGANISM: Homo sapiens

<400> SEQUENCE: 719

Glu Lys Lys Lys Arg Lys
1               5

<210> SEQ ID NO 720
<211> LENGTH: 6
<212> TYPE: PRT
<213> ORGANISM: Homo sapiens

<400> SEQUENCE: 720

Gln Arg Arg Asn Arg Thr
1               5

<210> SEQ ID NO 721
<211> LENGTH: 6
<212> TYPE: PRT
<213> ORGANISM: Homo sapiens

<400> SEQUENCE: 721

Asn Arg Arg Ala Lys Phe
1               5

<210> SEQ ID NO 722
<211> LENGTH: 6
<212> TYPE: PRT
<213> ORGANISM: Homo sapiens

<400> SEQUENCE: 722

Glu Lys Lys Lys Arg Lys
1               5

<210> SEQ ID NO 723
<211> LENGTH: 6
<212> TYPE: PRT
<213> ORGANISM: Homo sapiens

<400> SEQUENCE: 723

Gln Arg Arg Asn Arg Thr
1               5

<210> SEQ ID NO 724
<211> LENGTH: 6
<212> TYPE: PRT
<213> ORGANISM: Homo sapiens

<400> SEQUENCE: 724

Asn Arg Arg Ala Lys Phe
1               5

<210> SEQ ID NO 725
<211> LENGTH: 8
<212> TYPE: PRT
<213> ORGANISM: Homo sapiens
```

```
<400> SEQUENCE: 725

Leu Lys Arg Lys Trp Ile Arg Cys
1               5

<210> SEQ ID NO 726
<211> LENGTH: 6
<212> TYPE: PRT
<213> ORGANISM: Homo sapiens

<400> SEQUENCE: 726

Thr Arg Lys Ile Lys Leu
1               5

<210> SEQ ID NO 727
<211> LENGTH: 6
<212> TYPE: PRT
<213> ORGANISM: Homo sapiens

<400> SEQUENCE: 727

Met Arg Lys Gln Arg Glu
1               5

<210> SEQ ID NO 728
<211> LENGTH: 6
<212> TYPE: PRT
<213> ORGANISM: Homo sapiens

<400> SEQUENCE: 728

Thr Arg Lys Ile Lys Leu
1               5

<210> SEQ ID NO 729
<211> LENGTH: 6
<212> TYPE: PRT
<213> ORGANISM: Homo sapiens

<400> SEQUENCE: 729

Met Arg Lys Gln Arg Glu
1               5

<210> SEQ ID NO 730
<211> LENGTH: 6
<212> TYPE: PRT
<213> ORGANISM: Homo sapiens

<400> SEQUENCE: 730

Pro Arg Arg Thr Arg Pro
1               5

<210> SEQ ID NO 731
<211> LENGTH: 6
<212> TYPE: PRT
<213> ORGANISM: Homo sapiens

<400> SEQUENCE: 731

Gly Arg Arg Lys Arg Phe
1               5

<210> SEQ ID NO 732
<211> LENGTH: 6
<212> TYPE: PRT
<213> ORGANISM: Homo sapiens

<400> SEQUENCE: 732
```

```
Gly Lys Lys Arg Lys Asn
1               5

<210> SEQ ID NO 733
<211> LENGTH: 6
<212> TYPE: PRT
<213> ORGANISM: Homo sapiens

<400> SEQUENCE: 733

Gly Lys Lys Arg Lys Cys
1               5

<210> SEQ ID NO 734
<211> LENGTH: 6
<212> TYPE: PRT
<213> ORGANISM: Homo sapiens

<400> SEQUENCE: 734

Pro Arg Arg Thr Arg Pro
1               5

<210> SEQ ID NO 735
<211> LENGTH: 6
<212> TYPE: PRT
<213> ORGANISM: Homo sapiens

<400> SEQUENCE: 735

Gly Arg Arg Lys Arg Phe
1               5

<210> SEQ ID NO 736
<211> LENGTH: 6
<212> TYPE: PRT
<213> ORGANISM: Homo sapiens

<400> SEQUENCE: 736

Gly Lys Lys Arg Lys Asn
1               5

<210> SEQ ID NO 737
<211> LENGTH: 6
<212> TYPE: PRT
<213> ORGANISM: Homo sapiens

<400> SEQUENCE: 737

Gly Lys Lys Arg Lys Cys
1               5

<210> SEQ ID NO 738
<211> LENGTH: 8
<212> TYPE: PRT
<213> ORGANISM: Homo sapiens

<400> SEQUENCE: 738

Ala Arg Arg Arg Cys Asp Arg Asp
1               5

<210> SEQ ID NO 739
<211> LENGTH: 6
<212> TYPE: PRT
<213> ORGANISM: Homo sapiens

<400> SEQUENCE: 739

Glu Lys Lys Ser Lys Asp
1               5
```

```
<210> SEQ ID NO 740
<211> LENGTH: 6
<212> TYPE: PRT
<213> ORGANISM: Homo sapiens

<400> SEQUENCE: 740

Glu Lys Lys Ser Lys Asp
1               5

<210> SEQ ID NO 741
<211> LENGTH: 6
<212> TYPE: PRT
<213> ORGANISM: Homo sapiens

<400> SEQUENCE: 741

Pro Arg Lys Ala Arg Val
1               5

<210> SEQ ID NO 742
<211> LENGTH: 6
<212> TYPE: PRT
<213> ORGANISM: Homo sapiens

<400> SEQUENCE: 742

Pro Arg Lys Ala Arg Val
1               5

<210> SEQ ID NO 743
<211> LENGTH: 6
<212> TYPE: PRT
<213> ORGANISM: Homo sapiens

<400> SEQUENCE: 743

Lys Lys Lys Tyr Lys Ala
1               5

<210> SEQ ID NO 744
<211> LENGTH: 6
<212> TYPE: PRT
<213> ORGANISM: Homo sapiens

<400> SEQUENCE: 744

Arg Arg Arg Leu Lys Glu
1               5

<210> SEQ ID NO 745
<211> LENGTH: 6
<212> TYPE: PRT
<213> ORGANISM: Homo sapiens

<400> SEQUENCE: 745

Lys Lys Lys Tyr Lys Ala
1               5

<210> SEQ ID NO 746
<211> LENGTH: 6
<212> TYPE: PRT
<213> ORGANISM: Homo sapiens

<400> SEQUENCE: 746

Arg Arg Arg Leu Lys Glu
1               5
```

```
<210> SEQ ID NO 747
<211> LENGTH: 6
<212> TYPE: PRT
<213> ORGANISM: Homo sapiens

<400> SEQUENCE: 747

Lys Arg Arg Gln Arg Asp
1               5

<210> SEQ ID NO 748
<211> LENGTH: 6
<212> TYPE: PRT
<213> ORGANISM: Homo sapiens

<400> SEQUENCE: 748

Lys Arg Arg Gln Arg Asp
1               5

<210> SEQ ID NO 749
<211> LENGTH: 6
<212> TYPE: PRT
<213> ORGANISM: Homo sapiens

<400> SEQUENCE: 749

Thr Arg Arg Cys Arg Cys
1               5

<210> SEQ ID NO 750
<211> LENGTH: 6
<212> TYPE: PRT
<213> ORGANISM: Homo sapiens

<400> SEQUENCE: 750

Ile Arg Arg Lys Arg Leu
1               5

<210> SEQ ID NO 751
<211> LENGTH: 6
<212> TYPE: PRT
<213> ORGANISM: Homo sapiens

<400> SEQUENCE: 751

Thr Arg Arg Cys Arg Cys
1               5

<210> SEQ ID NO 752
<211> LENGTH: 6
<212> TYPE: PRT
<213> ORGANISM: Homo sapiens

<400> SEQUENCE: 752

Ile Arg Arg Lys Arg Leu
1               5

<210> SEQ ID NO 753
<211> LENGTH: 8
<212> TYPE: PRT
<213> ORGANISM: Homo sapiens

<400> SEQUENCE: 753

Gln Lys Arg Arg Thr Leu Lys Asn
1               5

<210> SEQ ID NO 754
<211> LENGTH: 6
```

```
<212> TYPE: PRT
<213> ORGANISM: Homo sapiens

<400> SEQUENCE: 754

Met Arg Arg Leu Arg Ser
1               5

<210> SEQ ID NO 755
<211> LENGTH: 6
<212> TYPE: PRT
<213> ORGANISM: Homo sapiens

<400> SEQUENCE: 755

Met Arg Arg Leu Arg Ser
1               5

<210> SEQ ID NO 756
<211> LENGTH: 6
<212> TYPE: PRT
<213> ORGANISM: Homo sapiens

<400> SEQUENCE: 756

Gln Lys Lys Val Lys Ile
1               5

<210> SEQ ID NO 757
<211> LENGTH: 6
<212> TYPE: PRT
<213> ORGANISM: Homo sapiens

<400> SEQUENCE: 757

Asn Arg Arg Lys Arg Lys
1               5

<210> SEQ ID NO 758
<211> LENGTH: 6
<212> TYPE: PRT
<213> ORGANISM: Homo sapiens

<400> SEQUENCE: 758

Leu Arg Arg Tyr Lys Arg
1               5

<210> SEQ ID NO 759
<211> LENGTH: 6
<212> TYPE: PRT
<213> ORGANISM: Homo sapiens

<400> SEQUENCE: 759

Gln Lys Lys Val Lys Ile
1               5

<210> SEQ ID NO 760
<211> LENGTH: 6
<212> TYPE: PRT
<213> ORGANISM: Homo sapiens

<400> SEQUENCE: 760

Asn Arg Arg Lys Arg Lys
1               5

<210> SEQ ID NO 761
<211> LENGTH: 6
<212> TYPE: PRT
<213> ORGANISM: Homo sapiens
```

```
<400> SEQUENCE: 761

Leu Arg Arg Tyr Lys Arg
1               5

<210> SEQ ID NO 762
<211> LENGTH: 6
<212> TYPE: PRT
<213> ORGANISM: Homo sapiens

<400> SEQUENCE: 762

Lys Lys Lys Glu Lys Glu
1               5

<210> SEQ ID NO 763
<211> LENGTH: 6
<212> TYPE: PRT
<213> ORGANISM: Homo sapiens

<400> SEQUENCE: 763

Lys Lys Lys Glu Lys Glu
1               5

<210> SEQ ID NO 764
<211> LENGTH: 8
<212> TYPE: PRT
<213> ORGANISM: Homo sapiens

<400> SEQUENCE: 764

Ala Lys Arg Lys Ala Asp Arg Glu
1               5

<210> SEQ ID NO 765
<211> LENGTH: 6
<212> TYPE: PRT
<213> ORGANISM: Homo sapiens

<400> SEQUENCE: 765

Lys Lys Arg His Arg Glu
1               5

<210> SEQ ID NO 766
<211> LENGTH: 6
<212> TYPE: PRT
<213> ORGANISM: Homo sapiens

<400> SEQUENCE: 766

Lys Lys Arg His Arg Glu
1               5

<210> SEQ ID NO 767
<211> LENGTH: 8
<212> TYPE: PRT
<213> ORGANISM: Homo sapiens

<400> SEQUENCE: 767

Leu Arg Arg Arg Leu Glu Lys Arg
1               5

<210> SEQ ID NO 768
<211> LENGTH: 6
<212> TYPE: PRT
<213> ORGANISM: Homo sapiens

<400> SEQUENCE: 768
```

Ser Arg Arg Val Lys Ala
1               5

<210> SEQ ID NO 769
<211> LENGTH: 6
<212> TYPE: PRT
<213> ORGANISM: Homo sapiens

<400> SEQUENCE: 769

Ser Arg Arg Val Lys Ala
1               5

<210> SEQ ID NO 770
<211> LENGTH: 8
<212> TYPE: PRT
<213> ORGANISM: Homo sapiens

<400> SEQUENCE: 770

Arg Lys Arg Lys Leu Glu Arg Ile
1               5

<210> SEQ ID NO 771
<211> LENGTH: 6
<212> TYPE: PRT
<213> ORGANISM: Homo sapiens

<400> SEQUENCE: 771

Arg Lys Arg Leu Arg Asn
1               5

<210> SEQ ID NO 772
<211> LENGTH: 6
<212> TYPE: PRT
<213> ORGANISM: Homo sapiens

<400> SEQUENCE: 772

Cys Arg Lys Arg Lys Leu
1               5

<210> SEQ ID NO 773
<211> LENGTH: 6
<212> TYPE: PRT
<213> ORGANISM: Homo sapiens

<400> SEQUENCE: 773

Arg Lys Arg Leu Arg Asn
1               5

<210> SEQ ID NO 774
<211> LENGTH: 6
<212> TYPE: PRT
<213> ORGANISM: Homo sapiens

<400> SEQUENCE: 774

Cys Arg Lys Arg Lys Leu
1               5

<210> SEQ ID NO 775
<211> LENGTH: 6
<212> TYPE: PRT
<213> ORGANISM: Homo sapiens

<400> SEQUENCE: 775

Val Arg Lys Ala Arg Gly 1               5

<210> SEQ ID NO 776
<211> LENGTH: 6
<212> TYPE: PRT
<213> ORGANISM: Homo sapiens

<400> SEQUENCE: 776

Val Arg Lys Ala Arg Gly
1               5

<210> SEQ ID NO 777
<211> LENGTH: 6
<212> TYPE: PRT
<213> ORGANISM: Homo sapiens

<400> SEQUENCE: 777

Asp Arg Arg Phe Arg Ser
1               5

<210> SEQ ID NO 778
<211> LENGTH: 6
<212> TYPE: PRT
<213> ORGANISM: Homo sapiens

<400> SEQUENCE: 778

Ser Arg Arg Gln Arg Ile
1               5

<210> SEQ ID NO 779
<211> LENGTH: 6
<212> TYPE: PRT
<213> ORGANISM: Homo sapiens

<400> SEQUENCE: 779

Asp Arg Arg Phe Arg Ser
1               5

<210> SEQ ID NO 780
<211> LENGTH: 6
<212> TYPE: PRT
<213> ORGANISM: Homo sapiens

<400> SEQUENCE: 780

Ser Arg Arg Gln Arg Ile
1               5

<210> SEQ ID NO 781
<211> LENGTH: 6
<212> TYPE: PRT
<213> ORGANISM: Homo sapiens

<400> SEQUENCE: 781

Thr Lys Arg Arg Arg Lys
1               5

<210> SEQ ID NO 782
<211> LENGTH: 6
<212> TYPE: PRT
<213> ORGANISM: Homo sapiens

<400> SEQUENCE: 782

Val Lys Lys Tyr Lys Ser
1               5

```
<210> SEQ ID NO 783
<211> LENGTH: 6
<212> TYPE: PRT
<213> ORGANISM: Homo sapiens

<400> SEQUENCE: 783

Thr Lys Arg Arg Arg Lys
1               5

<210> SEQ ID NO 784
<211> LENGTH: 6
<212> TYPE: PRT
<213> ORGANISM: Homo sapiens

<400> SEQUENCE: 784

Val Lys Lys Tyr Lys Ser
1               5

<210> SEQ ID NO 785
<211> LENGTH: 8
<212> TYPE: PRT
<213> ORGANISM: Homo sapiens

<400> SEQUENCE: 785

Gln Arg Arg Arg Thr Leu Lys Asn
1               5

<210> SEQ ID NO 786
<211> LENGTH: 8
<212> TYPE: PRT
<213> ORGANISM: Homo sapiens

<400> SEQUENCE: 786

Asn Lys Lys Lys Ile Leu Arg Glu
1               5

<210> SEQ ID NO 787
<211> LENGTH: 6
<212> TYPE: PRT
<213> ORGANISM: Homo sapiens

<400> SEQUENCE: 787

Leu Lys Lys Leu Arg Ile
1               5

<210> SEQ ID NO 788
<211> LENGTH: 6
<212> TYPE: PRT
<213> ORGANISM: Homo sapiens

<400> SEQUENCE: 788

Phe Lys Lys Gly Arg Leu
1               5

<210> SEQ ID NO 789
<211> LENGTH: 6
<212> TYPE: PRT
<213> ORGANISM: Homo sapiens

<400> SEQUENCE: 789

Cys Arg Arg His Lys Ile
1               5

<210> SEQ ID NO 790
```

```
<211> LENGTH: 6
<212> TYPE: PRT
<213> ORGANISM: Homo sapiens

<400> SEQUENCE: 790

Leu Lys Lys Leu Arg Ile
1               5

<210> SEQ ID NO 791
<211> LENGTH: 6
<212> TYPE: PRT
<213> ORGANISM: Homo sapiens

<400> SEQUENCE: 791

Phe Lys Lys Gly Arg Leu
1               5

<210> SEQ ID NO 792
<211> LENGTH: 6
<212> TYPE: PRT
<213> ORGANISM: Homo sapiens

<400> SEQUENCE: 792

Cys Arg Arg His Lys Ile
1               5

<210> SEQ ID NO 793
<211> LENGTH: 6
<212> TYPE: PRT
<213> ORGANISM: Homo sapiens

<400> SEQUENCE: 793

Ala Lys Lys Ile Lys Met
1               5

<210> SEQ ID NO 794
<211> LENGTH: 6
<212> TYPE: PRT
<213> ORGANISM: Homo sapiens

<400> SEQUENCE: 794

Ala Lys Lys Ile Lys Met
1               5

<210> SEQ ID NO 795
<211> LENGTH: 8
<212> TYPE: PRT
<213> ORGANISM: Homo sapiens

<400> SEQUENCE: 795

Val Arg Lys Arg Cys His Lys His
1               5

<210> SEQ ID NO 796
<211> LENGTH: 6
<212> TYPE: PRT
<213> ORGANISM: Homo sapiens

<400> SEQUENCE: 796

Arg Lys Lys Phe Lys Cys
1               5

<210> SEQ ID NO 797
<211> LENGTH: 6
<212> TYPE: PRT
```

<213> ORGANISM: Homo sapiens

<400> SEQUENCE: 797

Arg Lys Lys Phe Lys Cys
1               5

<210> SEQ ID NO 798
<211> LENGTH: 6
<212> TYPE: PRT
<213> ORGANISM: Homo sapiens

<400> SEQUENCE: 798

Glu Lys Lys Ala Arg Ser
1               5

<210> SEQ ID NO 799
<211> LENGTH: 6
<212> TYPE: PRT
<213> ORGANISM: Homo sapiens

<400> SEQUENCE: 799

Gly Arg Arg Arg Arg Thr
1               5

<210> SEQ ID NO 800
<211> LENGTH: 6
<212> TYPE: PRT
<213> ORGANISM: Homo sapiens

<400> SEQUENCE: 800

Glu Arg Arg Gln Arg Phe
1               5

<210> SEQ ID NO 801
<211> LENGTH: 6
<212> TYPE: PRT
<213> ORGANISM: Homo sapiens

<400> SEQUENCE: 801

Glu Lys Lys Ala Arg Ser
1               5

<210> SEQ ID NO 802
<211> LENGTH: 6
<212> TYPE: PRT
<213> ORGANISM: Homo sapiens

<400> SEQUENCE: 802

Gly Arg Arg Arg Arg Thr
1               5

<210> SEQ ID NO 803
<211> LENGTH: 6
<212> TYPE: PRT
<213> ORGANISM: Homo sapiens

<400> SEQUENCE: 803

Glu Arg Arg Gln Arg Phe
1               5

<210> SEQ ID NO 804
<211> LENGTH: 6
<212> TYPE: PRT
<213> ORGANISM: Homo sapiens

```
<400> SEQUENCE: 804

Leu Arg Lys Phe Arg Thr
1               5

<210> SEQ ID NO 805
<211> LENGTH: 6
<212> TYPE: PRT
<213> ORGANISM: Homo sapiens

<400> SEQUENCE: 805

Leu Arg Lys Phe Arg Thr
1               5

<210> SEQ ID NO 806
<211> LENGTH: 6
<212> TYPE: PRT
<213> ORGANISM: Homo sapiens

<400> SEQUENCE: 806

Arg Arg Arg Cys Arg Asp
1               5

<210> SEQ ID NO 807
<211> LENGTH: 6
<212> TYPE: PRT
<213> ORGANISM: Homo sapiens

<400> SEQUENCE: 807

Val Lys Arg Pro Arg Phe
1               5

<210> SEQ ID NO 808
<211> LENGTH: 6
<212> TYPE: PRT
<213> ORGANISM: Homo sapiens

<400> SEQUENCE: 808

Val Arg Lys Arg Arg Val
1               5

<210> SEQ ID NO 809
<211> LENGTH: 6
<212> TYPE: PRT
<213> ORGANISM: Homo sapiens

<400> SEQUENCE: 809

Glu Lys Lys Ser Lys Asn
1               5

<210> SEQ ID NO 810
<211> LENGTH: 6
<212> TYPE: PRT
<213> ORGANISM: Homo sapiens

<400> SEQUENCE: 810

Arg Arg Arg Cys Arg Asp
1               5

<210> SEQ ID NO 811
<211> LENGTH: 6
<212> TYPE: PRT
<213> ORGANISM: Homo sapiens

<400> SEQUENCE: 811
```

```
Val Lys Arg Pro Arg Phe
1               5

<210> SEQ ID NO 812
<211> LENGTH: 6
<212> TYPE: PRT
<213> ORGANISM: Homo sapiens

<400> SEQUENCE: 812

Val Arg Lys Arg Arg Val
1               5

<210> SEQ ID NO 813
<211> LENGTH: 6
<212> TYPE: PRT
<213> ORGANISM: Homo sapiens

<400> SEQUENCE: 813

Glu Lys Lys Ser Lys Asn
1               5

<210> SEQ ID NO 814
<211> LENGTH: 8
<212> TYPE: PRT
<213> ORGANISM: Homo sapiens

<400> SEQUENCE: 814

Ile Arg Lys Lys Val Arg Arg Leu
1               5

<210> SEQ ID NO 815
<211> LENGTH: 6
<212> TYPE: PRT
<213> ORGANISM: Homo sapiens

<400> SEQUENCE: 815

Lys Arg Arg Ala Lys Ala
1               5

<210> SEQ ID NO 816
<211> LENGTH: 6
<212> TYPE: PRT
<213> ORGANISM: Homo sapiens

<400> SEQUENCE: 816

Met Lys Lys Val Arg Arg
1               5

<210> SEQ ID NO 817
<211> LENGTH: 6
<212> TYPE: PRT
<213> ORGANISM: Homo sapiens

<400> SEQUENCE: 817

Asp Lys Arg Lys Arg Ser
1               5

<210> SEQ ID NO 818
<211> LENGTH: 6
<212> TYPE: PRT
<213> ORGANISM: Homo sapiens

<400> SEQUENCE: 818

Arg Lys Lys Val Arg Arg
1               5
```

```
<210> SEQ ID NO 819
<211> LENGTH: 6
<212> TYPE: PRT
<213> ORGANISM: Homo sapiens

<400> SEQUENCE: 819

Thr Lys Lys Cys Arg Glu
1               5

<210> SEQ ID NO 820
<211> LENGTH: 6
<212> TYPE: PRT
<213> ORGANISM: Homo sapiens

<400> SEQUENCE: 820

Lys Arg Arg Ala Lys Ala
1               5

<210> SEQ ID NO 821
<211> LENGTH: 6
<212> TYPE: PRT
<213> ORGANISM: Homo sapiens

<400> SEQUENCE: 821

Met Lys Lys Val Arg Arg
1               5

<210> SEQ ID NO 822
<211> LENGTH: 6
<212> TYPE: PRT
<213> ORGANISM: Homo sapiens

<400> SEQUENCE: 822

Asp Lys Arg Lys Arg Ser
1               5

<210> SEQ ID NO 823
<211> LENGTH: 6
<212> TYPE: PRT
<213> ORGANISM: Homo sapiens

<400> SEQUENCE: 823

Arg Lys Lys Val Arg Arg
1               5

<210> SEQ ID NO 824
<211> LENGTH: 6
<212> TYPE: PRT
<213> ORGANISM: Homo sapiens

<400> SEQUENCE: 824

Thr Lys Lys Cys Arg Glu
1               5

<210> SEQ ID NO 825
<211> LENGTH: 8
<212> TYPE: PRT
<213> ORGANISM: Homo sapiens

<400> SEQUENCE: 825

Lys Arg Lys Lys Ser Glu Arg Thr
1               5
```

```
<210> SEQ ID NO 826
<211> LENGTH: 6
<212> TYPE: PRT
<213> ORGANISM: Homo sapiens

<400> SEQUENCE: 826

Thr Arg Lys Thr Arg Arg
1               5

<210> SEQ ID NO 827
<211> LENGTH: 6
<212> TYPE: PRT
<213> ORGANISM: Homo sapiens

<400> SEQUENCE: 827

Ile Lys Arg Lys Lys Ser
1               5

<210> SEQ ID NO 828
<211> LENGTH: 6
<212> TYPE: PRT
<213> ORGANISM: Homo sapiens

<400> SEQUENCE: 828

Thr Arg Lys Thr Arg Arg
1               5

<210> SEQ ID NO 829
<211> LENGTH: 6
<212> TYPE: PRT
<213> ORGANISM: Homo sapiens

<400> SEQUENCE: 829

Ile Lys Arg Lys Lys Ser
1               5

<210> SEQ ID NO 830
<211> LENGTH: 8
<212> TYPE: PRT
<213> ORGANISM: Homo sapiens

<400> SEQUENCE: 830

Arg Lys Arg Lys Ala Glu Lys Gln
1               5

<210> SEQ ID NO 831
<211> LENGTH: 8
<212> TYPE: PRT
<213> ORGANISM: Homo sapiens

<400> SEQUENCE: 831

Lys Lys Arg Lys Gly Gly Arg Asn
1               5

<210> SEQ ID NO 832
<211> LENGTH: 6
<212> TYPE: PRT
<213> ORGANISM: Homo sapiens

<400> SEQUENCE: 832

Ala Arg Arg Gly Arg Lys
1               5

<210> SEQ ID NO 833
<211> LENGTH: 6
```

```
<212> TYPE: PRT
<213> ORGANISM: Homo sapiens

<400> SEQUENCE: 833

Pro Lys Arg Gly Arg Pro
1               5

<210> SEQ ID NO 834
<211> LENGTH: 6
<212> TYPE: PRT
<213> ORGANISM: Homo sapiens

<400> SEQUENCE: 834

Glu Lys Lys Arg Lys Gly
1               5

<210> SEQ ID NO 835
<211> LENGTH: 6
<212> TYPE: PRT
<213> ORGANISM: Homo sapiens

<400> SEQUENCE: 835

Asp Arg Lys Arg Lys Gln
1               5

<210> SEQ ID NO 836
<211> LENGTH: 6
<212> TYPE: PRT
<213> ORGANISM: Homo sapiens

<400> SEQUENCE: 836

Leu Lys Lys Ile Arg Arg
1               5

<210> SEQ ID NO 837
<211> LENGTH: 9
<212> TYPE: PRT
<213> ORGANISM: Homo sapiens

<400> SEQUENCE: 837

Val Lys Lys Val Glu Lys Lys Arg Glu
1               5

<210> SEQ ID NO 838
<211> LENGTH: 6
<212> TYPE: PRT
<213> ORGANISM: Homo sapiens

<400> SEQUENCE: 838

Ala Arg Arg Gly Arg Lys
1               5

<210> SEQ ID NO 839
<211> LENGTH: 6
<212> TYPE: PRT
<213> ORGANISM: Homo sapiens

<400> SEQUENCE: 839

Pro Lys Arg Gly Arg Pro
1               5

<210> SEQ ID NO 840
<211> LENGTH: 6
<212> TYPE: PRT
<213> ORGANISM: Homo sapiens
```

-continued

<400> SEQUENCE: 840

Glu Lys Lys Arg Lys Gly
1               5

<210> SEQ ID NO 841
<211> LENGTH: 6
<212> TYPE: PRT
<213> ORGANISM: Homo sapiens

<400> SEQUENCE: 841

Asp Arg Lys Arg Lys Gln
1               5

<210> SEQ ID NO 842
<211> LENGTH: 6
<212> TYPE: PRT
<213> ORGANISM: Homo sapiens

<400> SEQUENCE: 842

Leu Lys Lys Ile Arg Arg
1               5

<210> SEQ ID NO 843
<211> LENGTH: 8
<212> TYPE: PRT
<213> ORGANISM: Homo sapiens

<400> SEQUENCE: 843

Thr Lys Arg Arg Lys Arg Lys Asn
1               5

<210> SEQ ID NO 844
<211> LENGTH: 6
<212> TYPE: PRT
<213> ORGANISM: Homo sapiens

<400> SEQUENCE: 844

Thr Lys Arg Arg Lys Arg
1               5

<210> SEQ ID NO 845
<211> LENGTH: 6
<212> TYPE: PRT
<213> ORGANISM: Homo sapiens

<400> SEQUENCE: 845

Thr Lys Arg Arg Lys Arg
1               5

<210> SEQ ID NO 846
<211> LENGTH: 6
<212> TYPE: PRT
<213> ORGANISM: Homo sapiens

<400> SEQUENCE: 846

Trp Lys Arg Ile Arg Phe
1               5

<210> SEQ ID NO 847
<211> LENGTH: 6
<212> TYPE: PRT
<213> ORGANISM: Homo sapiens

<400> SEQUENCE: 847

```
Trp Lys Arg Ile Arg Phe
1               5

<210> SEQ ID NO 848
<211> LENGTH: 8
<212> TYPE: PRT
<213> ORGANISM: Homo sapiens

<400> SEQUENCE: 848

Asp Lys Lys Lys Leu Arg Arg Leu
1               5

<210> SEQ ID NO 849
<211> LENGTH: 6
<212> TYPE: PRT
<213> ORGANISM: Homo sapiens

<400> SEQUENCE: 849

Met Arg Lys Asp Lys Lys
1               5

<210> SEQ ID NO 850
<211> LENGTH: 6
<212> TYPE: PRT
<213> ORGANISM: Homo sapiens

<400> SEQUENCE: 850

Asn Lys Arg Gln Lys Ile
1               5

<210> SEQ ID NO 851
<211> LENGTH: 6
<212> TYPE: PRT
<213> ORGANISM: Homo sapiens

<400> SEQUENCE: 851

Met Arg Lys Asp Lys Lys
1               5

<210> SEQ ID NO 852
<211> LENGTH: 6
<212> TYPE: PRT
<213> ORGANISM: Homo sapiens

<400> SEQUENCE: 852

Asn Lys Arg Gln Lys Ile
1               5

<210> SEQ ID NO 853
<211> LENGTH: 6
<212> TYPE: PRT
<213> ORGANISM: Homo sapiens

<400> SEQUENCE: 853

Lys Arg Lys His Arg Asn
1               5

<210> SEQ ID NO 854
<211> LENGTH: 6
<212> TYPE: PRT
<213> ORGANISM: Homo sapiens

<400> SEQUENCE: 854

Glu Lys Arg Arg Lys Ala
```

```
1               5

<210> SEQ ID NO 855
<211> LENGTH: 6
<212> TYPE: PRT
<213> ORGANISM: Homo sapiens

<400> SEQUENCE: 855

Lys Arg Lys His Arg Asn
1               5

<210> SEQ ID NO 856
<211> LENGTH: 6
<212> TYPE: PRT
<213> ORGANISM: Homo sapiens

<400> SEQUENCE: 856

Glu Lys Arg Arg Lys Ala
1               5

<210> SEQ ID NO 857
<211> LENGTH: 8
<212> TYPE: PRT
<213> ORGANISM: Homo sapiens

<400> SEQUENCE: 857

Glu Lys Lys Lys Val Ser Lys Ala
1               5

<210> SEQ ID NO 858
<211> LENGTH: 6
<212> TYPE: PRT
<213> ORGANISM: Homo sapiens

<400> SEQUENCE: 858

Ile Lys Arg Lys Lys Phe
1               5

<210> SEQ ID NO 859
<211> LENGTH: 6
<212> TYPE: PRT
<213> ORGANISM: Homo sapiens

<400> SEQUENCE: 859

Thr Lys Arg Val Lys Lys
1               5

<210> SEQ ID NO 860
<211> LENGTH: 6
<212> TYPE: PRT
<213> ORGANISM: Homo sapiens

<400> SEQUENCE: 860

Asp Arg Arg Gln Lys Arg
1               5

<210> SEQ ID NO 861
<211> LENGTH: 6
<212> TYPE: PRT
<213> ORGANISM: Homo sapiens

<400> SEQUENCE: 861

Ile Lys Arg Lys Lys Phe
1               5
```

<210> SEQ ID NO 862
<211> LENGTH: 6
<212> TYPE: PRT
<213> ORGANISM: Homo sapiens

<400> SEQUENCE: 862

Thr Lys Arg Val Lys Lys
1               5

<210> SEQ ID NO 863
<211> LENGTH: 6
<212> TYPE: PRT
<213> ORGANISM: Homo sapiens

<400> SEQUENCE: 863

Asp Arg Arg Gln Lys Arg
1               5

<210> SEQ ID NO 864
<211> LENGTH: 6
<212> TYPE: PRT
<213> ORGANISM: Homo sapiens

<400> SEQUENCE: 864

Gln Arg Lys Gly Arg Lys
1               5

<210> SEQ ID NO 865
<211> LENGTH: 6
<212> TYPE: PRT
<213> ORGANISM: Homo sapiens

<400> SEQUENCE: 865

Ala Arg Arg Leu Arg Ala
1               5

<210> SEQ ID NO 866
<211> LENGTH: 6
<212> TYPE: PRT
<213> ORGANISM: Homo sapiens

<400> SEQUENCE: 866

Gln Arg Lys Gly Arg Lys
1               5

<210> SEQ ID NO 867
<211> LENGTH: 6
<212> TYPE: PRT
<213> ORGANISM: Homo sapiens

<400> SEQUENCE: 867

Ala Arg Arg Leu Arg Ala
1               5

<210> SEQ ID NO 868
<211> LENGTH: 6
<212> TYPE: PRT
<213> ORGANISM: Homo sapiens

<400> SEQUENCE: 868

Leu Arg Arg Thr Arg Ile
1               5

<210> SEQ ID NO 869

```
<211> LENGTH: 6
<212> TYPE: PRT
<213> ORGANISM: Homo sapiens

<400> SEQUENCE: 869

Leu Arg Arg Thr Arg Ile
1               5

<210> SEQ ID NO 870
<211> LENGTH: 6
<212> TYPE: PRT
<213> ORGANISM: Homo sapiens

<400> SEQUENCE: 870

Ile Lys Lys Leu Lys Val
1               5

<210> SEQ ID NO 871
<211> LENGTH: 6
<212> TYPE: PRT
<213> ORGANISM: Homo sapiens

<400> SEQUENCE: 871

Ile Lys Lys Leu Lys Val
1               5

<210> SEQ ID NO 872
<211> LENGTH: 6
<212> TYPE: PRT
<213> ORGANISM: Homo sapiens

<400> SEQUENCE: 872

Ile Lys Lys Leu Lys Val
1               5

<210> SEQ ID NO 873
<211> LENGTH: 6
<212> TYPE: PRT
<213> ORGANISM: Homo sapiens

<400> SEQUENCE: 873

Ile Lys Lys Leu Lys Val
1               5

<210> SEQ ID NO 874
<211> LENGTH: 8
<212> TYPE: PRT
<213> ORGANISM: Homo sapiens

<400> SEQUENCE: 874

Ala Arg Arg Arg Arg Lys Arg Arg
1               5

<210> SEQ ID NO 875
<211> LENGTH: 8
<212> TYPE: PRT
<213> ORGANISM: Homo sapiens

<400> SEQUENCE: 875

Pro Arg Arg Arg Arg Arg Arg Thr
1               5

<210> SEQ ID NO 876
<211> LENGTH: 8
<212> TYPE: PRT
```

-continued

<213> ORGANISM: Homo sapiens

<400> SEQUENCE: 876

Trp Lys Lys Lys Thr Ser Arg Pro
1               5

<210> SEQ ID NO 877
<211> LENGTH: 6
<212> TYPE: PRT
<213> ORGANISM: Homo sapiens

<400> SEQUENCE: 877

Ala Arg Arg Arg Arg Lys
1               5

<210> SEQ ID NO 878
<211> LENGTH: 6
<212> TYPE: PRT
<213> ORGANISM: Homo sapiens

<400> SEQUENCE: 878

Pro Arg Arg Arg Arg Arg
1               5

<210> SEQ ID NO 879
<211> LENGTH: 6
<212> TYPE: PRT
<213> ORGANISM: Homo sapiens

<400> SEQUENCE: 879

Pro Arg Arg Pro Arg Ile
1               5

<210> SEQ ID NO 880
<211> LENGTH: 6
<212> TYPE: PRT
<213> ORGANISM: Homo sapiens

<400> SEQUENCE: 880

Thr Arg Arg Met Arg Trp
1               5

<210> SEQ ID NO 881
<211> LENGTH: 6
<212> TYPE: PRT
<213> ORGANISM: Homo sapiens

<400> SEQUENCE: 881

Ala Arg Arg Arg Arg Lys
1               5

<210> SEQ ID NO 882
<211> LENGTH: 6
<212> TYPE: PRT
<213> ORGANISM: Homo sapiens

<400> SEQUENCE: 882

Pro Arg Arg Arg Arg Arg
1               5

<210> SEQ ID NO 883
<211> LENGTH: 6
<212> TYPE: PRT
<213> ORGANISM: Homo sapiens -continued

```
<400> SEQUENCE: 883

Pro Arg Arg Pro Arg Ile
1               5

<210> SEQ ID NO 884
<211> LENGTH: 6
<212> TYPE: PRT
<213> ORGANISM: Homo sapiens

<400> SEQUENCE: 884

Thr Arg Arg Met Arg Trp
1               5

<210> SEQ ID NO 885
<211> LENGTH: 8
<212> TYPE: PRT
<213> ORGANISM: Homo sapiens

<400> SEQUENCE: 885

Cys Lys Lys Lys Met Arg Arg Lys
1               5

<210> SEQ ID NO 886
<211> LENGTH: 6
<212> TYPE: PRT
<213> ORGANISM: Homo sapiens

<400> SEQUENCE: 886

Lys Lys Lys Met Arg Arg
1               5

<210> SEQ ID NO 887
<211> LENGTH: 6
<212> TYPE: PRT
<213> ORGANISM: Homo sapiens

<400> SEQUENCE: 887

His Arg Arg Ser Lys Gln
1               5

<210> SEQ ID NO 888
<211> LENGTH: 6
<212> TYPE: PRT
<213> ORGANISM: Homo sapiens

<400> SEQUENCE: 888

Lys Lys Lys Met Arg Arg
1               5

<210> SEQ ID NO 889
<211> LENGTH: 6
<212> TYPE: PRT
<213> ORGANISM: Homo sapiens

<400> SEQUENCE: 889

His Arg Arg Ser Lys Gln
1               5

<210> SEQ ID NO 890
<211> LENGTH: 6
<212> TYPE: PRT
<213> ORGANISM: Homo sapiens

<400> SEQUENCE: 890
```

```
Arg Lys Arg Gly Lys Asn
1               5

<210> SEQ ID NO 891
<211> LENGTH: 6
<212> TYPE: PRT
<213> ORGANISM: Homo sapiens

<400> SEQUENCE: 891

Arg Lys Arg Gly Lys Asn
1               5

<210> SEQ ID NO 892
<211> LENGTH: 8
<212> TYPE: PRT
<213> ORGANISM: Homo sapiens

<400> SEQUENCE: 892

Ile Lys Lys Arg Ser Leu Arg Ser
1               5

<210> SEQ ID NO 893
<211> LENGTH: 6
<212> TYPE: PRT
<213> ORGANISM: Homo sapiens

<400> SEQUENCE: 893

Ser Lys Arg Pro Lys Asn
1               5

<210> SEQ ID NO 894
<211> LENGTH: 6
<212> TYPE: PRT
<213> ORGANISM: Homo sapiens

<400> SEQUENCE: 894

Ser Lys Arg Pro Lys Asn
1               5

<210> SEQ ID NO 895
<211> LENGTH: 6
<212> TYPE: PRT
<213> ORGANISM: Homo sapiens

<400> SEQUENCE: 895

Pro Arg Arg Ser Arg Arg
1               5

<210> SEQ ID NO 896
<211> LENGTH: 6
<212> TYPE: PRT
<213> ORGANISM: Homo sapiens

<400> SEQUENCE: 896

Trp Arg Arg Thr Arg Gly
1               5

<210> SEQ ID NO 897
<211> LENGTH: 6
<212> TYPE: PRT
<213> ORGANISM: Homo sapiens

<400> SEQUENCE: 897

Pro Arg Arg Ser Arg Arg
1               5
```

```
<210> SEQ ID NO 898
<211> LENGTH: 6
<212> TYPE: PRT
<213> ORGANISM: Homo sapiens

<400> SEQUENCE: 898

Trp Arg Arg Thr Arg Gly
1               5

<210> SEQ ID NO 899
<211> LENGTH: 6
<212> TYPE: PRT
<213> ORGANISM: Homo sapiens

<400> SEQUENCE: 899

Gly Lys Lys Leu Lys Leu
1               5

<210> SEQ ID NO 900
<211> LENGTH: 6
<212> TYPE: PRT
<213> ORGANISM: Homo sapiens

<400> SEQUENCE: 900

Ile Arg Lys Gln Lys Leu
1               5

<210> SEQ ID NO 901
<211> LENGTH: 6
<212> TYPE: PRT
<213> ORGANISM: Homo sapiens

<400> SEQUENCE: 901

Gly Lys Lys Leu Lys Leu
1               5

<210> SEQ ID NO 902
<211> LENGTH: 6
<212> TYPE: PRT
<213> ORGANISM: Homo sapiens

<400> SEQUENCE: 902

Ile Arg Lys Gln Lys Leu
1               5

<210> SEQ ID NO 903
<211> LENGTH: 8
<212> TYPE: PRT
<213> ORGANISM: Homo sapiens

<400> SEQUENCE: 903

Asn Arg Lys Lys His Arg Arg Lys
1               5

<210> SEQ ID NO 904
<211> LENGTH: 6
<212> TYPE: PRT
<213> ORGANISM: Homo sapiens

<400> SEQUENCE: 904

Arg Lys Lys His Arg Arg
1               5
```

```
<210> SEQ ID NO 905
<211> LENGTH: 6
<212> TYPE: PRT
<213> ORGANISM: Homo sapiens

<400> SEQUENCE: 905

Arg Lys Lys His Arg Arg
1               5

<210> SEQ ID NO 906
<211> LENGTH: 6
<212> TYPE: PRT
<213> ORGANISM: Homo sapiens

<400> SEQUENCE: 906

Ala Arg Arg Lys Arg Arg
1               5

<210> SEQ ID NO 907
<211> LENGTH: 6
<212> TYPE: PRT
<213> ORGANISM: Homo sapiens

<400> SEQUENCE: 907

Asn Lys Arg Ile Arg Tyr
1               5

<210> SEQ ID NO 908
<211> LENGTH: 6
<212> TYPE: PRT
<213> ORGANISM: Homo sapiens

<400> SEQUENCE: 908

Ala Arg Arg Lys Arg Arg
1               5

<210> SEQ ID NO 909
<211> LENGTH: 6
<212> TYPE: PRT
<213> ORGANISM: Homo sapiens

<400> SEQUENCE: 909

Asn Lys Arg Ile Arg Tyr
1               5

<210> SEQ ID NO 910
<211> LENGTH: 6
<212> TYPE: PRT
<213> ORGANISM: Homo sapiens

<400> SEQUENCE: 910

Asp Lys Lys Lys Arg Met
1               5

<210> SEQ ID NO 911
<211> LENGTH: 6
<212> TYPE: PRT
<213> ORGANISM: Homo sapiens

<400> SEQUENCE: 911

Lys Arg Lys Glu Lys Ala
1               5

<210> SEQ ID NO 912
<211> LENGTH: 6
```

```
<212> TYPE: PRT
<213> ORGANISM: Homo sapiens

<400> SEQUENCE: 912

Tyr Arg Lys Lys Lys Gln
1               5

<210> SEQ ID NO 913
<211> LENGTH: 6
<212> TYPE: PRT
<213> ORGANISM: Homo sapiens

<400> SEQUENCE: 913

Asp Lys Lys Lys Arg Met
1               5

<210> SEQ ID NO 914
<211> LENGTH: 6
<212> TYPE: PRT
<213> ORGANISM: Homo sapiens

<400> SEQUENCE: 914

Lys Arg Lys Glu Lys Ala
1               5

<210> SEQ ID NO 915
<211> LENGTH: 6
<212> TYPE: PRT
<213> ORGANISM: Homo sapiens

<400> SEQUENCE: 915

Tyr Arg Lys Lys Lys Gln
1               5

<210> SEQ ID NO 916
<211> LENGTH: 6
<212> TYPE: PRT
<213> ORGANISM: Homo sapiens

<400> SEQUENCE: 916

Ile Lys Arg Leu Lys Ile
1               5

<210> SEQ ID NO 917
<211> LENGTH: 6
<212> TYPE: PRT
<213> ORGANISM: Homo sapiens

<400> SEQUENCE: 917

Ile Lys Arg Leu Lys Ile
1               5

<210> SEQ ID NO 918
<211> LENGTH: 8
<212> TYPE: PRT
<213> ORGANISM: Homo sapiens

<400> SEQUENCE: 918

Arg Lys Arg Arg Gly Leu Arg Ser
1               5

<210> SEQ ID NO 919
<211> LENGTH: 8
<212> TYPE: PRT
<213> ORGANISM: Homo sapiens
```

```
<400> SEQUENCE: 919

Ser Arg Lys Lys Thr Arg Arg Met
1               5

<210> SEQ ID NO 920
<211> LENGTH: 6
<212> TYPE: PRT
<213> ORGANISM: Homo sapiens

<400> SEQUENCE: 920

Met Arg Arg Ser Arg Ala
1               5

<210> SEQ ID NO 921
<211> LENGTH: 6
<212> TYPE: PRT
<213> ORGANISM: Homo sapiens

<400> SEQUENCE: 921

Glu Arg Lys Arg Arg Gly
1               5

<210> SEQ ID NO 922
<211> LENGTH: 6
<212> TYPE: PRT
<213> ORGANISM: Homo sapiens

<400> SEQUENCE: 922

Arg Lys Lys Thr Arg Arg
1               5

<210> SEQ ID NO 923
<211> LENGTH: 6
<212> TYPE: PRT
<213> ORGANISM: Homo sapiens

<400> SEQUENCE: 923

Met Arg Arg Ser Arg Ala
1               5

<210> SEQ ID NO 924
<211> LENGTH: 6
<212> TYPE: PRT
<213> ORGANISM: Homo sapiens

<400> SEQUENCE: 924

Glu Arg Lys Arg Arg Gly
1               5

<210> SEQ ID NO 925
<211> LENGTH: 6
<212> TYPE: PRT
<213> ORGANISM: Homo sapiens

<400> SEQUENCE: 925

Arg Lys Lys Thr Arg Arg
1               5

<210> SEQ ID NO 926
<211> LENGTH: 8
<212> TYPE: PRT
<213> ORGANISM: Homo sapiens

<400> SEQUENCE: 926
```

```
Asn Lys Lys Lys His Leu Lys Lys
1               5

<210> SEQ ID NO 927
<211> LENGTH: 8
<212> TYPE: PRT
<213> ORGANISM: Homo sapiens

<400> SEQUENCE: 927

Glu Lys Lys Lys Leu Lys Arg His
1               5

<210> SEQ ID NO 928
<211> LENGTH: 6
<212> TYPE: PRT
<213> ORGANISM: Homo sapiens

<400> SEQUENCE: 928

Trp Lys Lys Lys Arg Ala
1               5

<210> SEQ ID NO 929
<211> LENGTH: 6
<212> TYPE: PRT
<213> ORGANISM: Homo sapiens

<400> SEQUENCE: 929

Arg Lys Lys Ala Lys Phe
1               5

<210> SEQ ID NO 930
<211> LENGTH: 6
<212> TYPE: PRT
<213> ORGANISM: Homo sapiens

<400> SEQUENCE: 930

Lys Lys Lys Leu Lys Arg
1               5

<210> SEQ ID NO 931
<211> LENGTH: 6
<212> TYPE: PRT
<213> ORGANISM: Homo sapiens

<400> SEQUENCE: 931

Trp Lys Lys Lys Arg Ala
1               5

<210> SEQ ID NO 932
<211> LENGTH: 6
<212> TYPE: PRT
<213> ORGANISM: Homo sapiens

<400> SEQUENCE: 932

Arg Lys Lys Ala Lys Phe
1               5

<210> SEQ ID NO 933
<211> LENGTH: 6
<212> TYPE: PRT
<213> ORGANISM: Homo sapiens

<400> SEQUENCE: 933

Lys Lys Lys Leu Lys Arg
```

-continued

<210> SEQ ID NO 934
<211> LENGTH: 6
<212> TYPE: PRT
<213> ORGANISM: Homo sapiens

<400> SEQUENCE: 934

Leu Lys Lys Phe Arg Gln
1               5

<210> SEQ ID NO 935
<211> LENGTH: 6
<212> TYPE: PRT
<213> ORGANISM: Homo sapiens

<400> SEQUENCE: 935

Leu Arg Lys Ile Arg Thr
1               5

<210> SEQ ID NO 936
<211> LENGTH: 6
<212> TYPE: PRT
<213> ORGANISM: Homo sapiens

<400> SEQUENCE: 936

Leu Lys Lys Phe Arg Gln
1               5

<210> SEQ ID NO 937
<211> LENGTH: 6
<212> TYPE: PRT
<213> ORGANISM: Homo sapiens

<400> SEQUENCE: 937

Leu Arg Lys Ile Arg Thr
1               5

<210> SEQ ID NO 938
<211> LENGTH: 8
<212> TYPE: PRT
<213> ORGANISM: Homo sapiens

<400> SEQUENCE: 938

Gln Lys Arg Arg Arg His Arg Ala
1               5

<210> SEQ ID NO 939
<211> LENGTH: 6
<212> TYPE: PRT
<213> ORGANISM: Homo sapiens

<400> SEQUENCE: 939

Gln Lys Arg Arg Arg His
1               5

<210> SEQ ID NO 940
<211> LENGTH: 6
<212> TYPE: PRT
<213> ORGANISM: Homo sapiens

<400> SEQUENCE: 940

Gln Lys Arg Arg Arg His
1               5

-continued

```
<210> SEQ ID NO 941
<211> LENGTH: 8
<212> TYPE: PRT
<213> ORGANISM: Homo sapiens

<400> SEQUENCE: 941

Gln Lys Arg Lys Thr Gly Arg Leu
1               5

<210> SEQ ID NO 942
<211> LENGTH: 8
<212> TYPE: PRT
<213> ORGANISM: Homo sapiens

<400> SEQUENCE: 942

Lys Arg Lys Lys Leu Val Arg Asp
1               5

<210> SEQ ID NO 943
<211> LENGTH: 8
<212> TYPE: PRT
<213> ORGANISM: Homo sapiens

<400> SEQUENCE: 943

Glu Lys Arg Arg Arg Glu Arg Glu
1               5

<210> SEQ ID NO 944
<211> LENGTH: 8
<212> TYPE: PRT
<213> ORGANISM: Homo sapiens

<400> SEQUENCE: 944

Glu Lys Lys Lys Lys Asn Lys Thr
1               5

<210> SEQ ID NO 945
<211> LENGTH: 6
<212> TYPE: PRT
<213> ORGANISM: Homo sapiens

<400> SEQUENCE: 945

Arg Lys Lys Asn Lys Gly
1               5

<210> SEQ ID NO 946
<211> LENGTH: 6
<212> TYPE: PRT
<213> ORGANISM: Homo sapiens

<400> SEQUENCE: 946

Ser Lys Lys Ser Lys Glu
1               5

<210> SEQ ID NO 947
<211> LENGTH: 6
<212> TYPE: PRT
<213> ORGANISM: Homo sapiens

<400> SEQUENCE: 947

Glu Lys Lys Val Arg Leu
1               5

<210> SEQ ID NO 948
```

```
<211> LENGTH: 6
<212> TYPE: PRT
<213> ORGANISM: Homo sapiens

<400> SEQUENCE: 948

Leu Lys Arg Lys Lys Leu
1               5

<210> SEQ ID NO 949
<211> LENGTH: 6
<212> TYPE: PRT
<213> ORGANISM: Homo sapiens

<400> SEQUENCE: 949

Glu Lys Arg Arg Arg Glu
1               5

<210> SEQ ID NO 950
<211> LENGTH: 6
<212> TYPE: PRT
<213> ORGANISM: Homo sapiens

<400> SEQUENCE: 950

Glu Lys Lys Glu Lys Lys
1               5

<210> SEQ ID NO 951
<211> LENGTH: 9
<212> TYPE: PRT
<213> ORGANISM: Homo sapiens

<400> SEQUENCE: 951

Gln Lys Lys Asp Val Val Lys Arg Gln
1               5

<210> SEQ ID NO 952
<211> LENGTH: 6
<212> TYPE: PRT
<213> ORGANISM: Homo sapiens

<400> SEQUENCE: 952

Arg Lys Lys Asn Lys Gly
1               5

<210> SEQ ID NO 953
<211> LENGTH: 6
<212> TYPE: PRT
<213> ORGANISM: Homo sapiens

<400> SEQUENCE: 953

Ser Lys Lys Ser Lys Glu
1               5

<210> SEQ ID NO 954
<211> LENGTH: 6
<212> TYPE: PRT
<213> ORGANISM: Homo sapiens

<400> SEQUENCE: 954

Glu Lys Lys Val Arg Leu
1               5

<210> SEQ ID NO 955
<211> LENGTH: 6
<212> TYPE: PRT
```

-continued

<213> ORGANISM: Homo sapiens

<400> SEQUENCE: 955

Leu Lys Arg Lys Lys Leu
1               5

<210> SEQ ID NO 956
<211> LENGTH: 6
<212> TYPE: PRT
<213> ORGANISM: Homo sapiens

<400> SEQUENCE: 956

Glu Lys Arg Arg Arg Glu
1               5

<210> SEQ ID NO 957
<211> LENGTH: 6
<212> TYPE: PRT
<213> ORGANISM: Homo sapiens

<400> SEQUENCE: 957

Glu Lys Lys Glu Lys Lys
1               5

<210> SEQ ID NO 958
<211> LENGTH: 6
<212> TYPE: PRT
<213> ORGANISM: Homo sapiens

<400> SEQUENCE: 958

Gly Lys Arg Tyr Lys Phe
1               5

<210> SEQ ID NO 959
<211> LENGTH: 6
<212> TYPE: PRT
<213> ORGANISM: Homo sapiens

<400> SEQUENCE: 959

Gly Lys Arg Tyr Lys Phe
1               5

<210> SEQ ID NO 960
<211> LENGTH: 6
<212> TYPE: PRT
<213> ORGANISM: Homo sapiens

<400> SEQUENCE: 960

Arg Arg Arg Gly Lys Thr
1               5

<210> SEQ ID NO 961
<211> LENGTH: 6
<212> TYPE: PRT
<213> ORGANISM: Homo sapiens

<400> SEQUENCE: 961

Arg Arg Arg Gly Lys Thr
1               5

<210> SEQ ID NO 962
<211> LENGTH: 6
<212> TYPE: PRT
<213> ORGANISM: Homo sapiens

```
<400> SEQUENCE: 962

Val Arg Arg Tyr Arg Ala
1               5

<210> SEQ ID NO 963
<211> LENGTH: 6
<212> TYPE: PRT
<213> ORGANISM: Homo sapiens

<400> SEQUENCE: 963

Val Arg Arg Tyr Arg Ala
1               5

<210> SEQ ID NO 964
<211> LENGTH: 6
<212> TYPE: PRT
<213> ORGANISM: Homo sapiens

<400> SEQUENCE: 964

Met Arg Arg Arg Lys Pro
1               5

<210> SEQ ID NO 965
<211> LENGTH: 6
<212> TYPE: PRT
<213> ORGANISM: Homo sapiens

<400> SEQUENCE: 965

Glu Lys Lys Lys Arg Glu
1               5

<210> SEQ ID NO 966
<211> LENGTH: 6
<212> TYPE: PRT
<213> ORGANISM: Homo sapiens

<400> SEQUENCE: 966

Met Arg Arg Arg Lys Pro
1               5

<210> SEQ ID NO 967
<211> LENGTH: 6
<212> TYPE: PRT
<213> ORGANISM: Homo sapiens

<400> SEQUENCE: 967

Glu Lys Lys Lys Arg Glu
1               5

<210> SEQ ID NO 968
<211> LENGTH: 6
<212> TYPE: PRT
<213> ORGANISM: Homo sapiens

<400> SEQUENCE: 968

Lys Lys Lys Val Lys Asn
1               5

<210> SEQ ID NO 969
<211> LENGTH: 6
<212> TYPE: PRT
<213> ORGANISM: Homo sapiens

<400> SEQUENCE: 969
```

Leu Arg Lys Thr Arg His
1               5

<210> SEQ ID NO 970
<211> LENGTH: 6
<212> TYPE: PRT
<213> ORGANISM: Homo sapiens

<400> SEQUENCE: 970

Lys Lys Lys Val Lys Asn
1               5

<210> SEQ ID NO 971
<211> LENGTH: 6
<212> TYPE: PRT
<213> ORGANISM: Homo sapiens

<400> SEQUENCE: 971

Leu Arg Lys Thr Arg His
1               5

<210> SEQ ID NO 972
<211> LENGTH: 6
<212> TYPE: PRT
<213> ORGANISM: Homo sapiens

<400> SEQUENCE: 972

Gly Lys Arg Trp Lys Glu
1               5

<210> SEQ ID NO 973
<211> LENGTH: 6
<212> TYPE: PRT
<213> ORGANISM: Homo sapiens

<400> SEQUENCE: 973

Gly Lys Arg Trp Lys Glu
1               5

<210> SEQ ID NO 974
<211> LENGTH: 6
<212> TYPE: PRT
<213> ORGANISM: Homo sapiens

<400> SEQUENCE: 974

Gly Lys Arg Trp Lys Glu
1               5

<210> SEQ ID NO 975
<211> LENGTH: 6
<212> TYPE: PRT
<213> ORGANISM: Homo sapiens

<400> SEQUENCE: 975

Leu Arg Lys Thr Lys Ala
1               5

<210> SEQ ID NO 976
<211> LENGTH: 6
<212> TYPE: PRT
<213> ORGANISM: Homo sapiens

<400> SEQUENCE: 976

Gly Lys Arg Trp Lys Glu
1               5

<210> SEQ ID NO 977
<211> LENGTH: 6
<212> TYPE: PRT
<213> ORGANISM: Homo sapiens

<400> SEQUENCE: 977

Leu Arg Lys Thr Lys Ala
1               5

<210> SEQ ID NO 978
<211> LENGTH: 8
<212> TYPE: PRT
<213> ORGANISM: Homo sapiens

<400> SEQUENCE: 978

Ile Arg Arg Arg Ala Val Arg Ser
1               5

<210> SEQ ID NO 979
<211> LENGTH: 6
<212> TYPE: PRT
<213> ORGANISM: Homo sapiens

<400> SEQUENCE: 979

Phe Lys Arg Lys Lys Phe
1               5

<210> SEQ ID NO 980
<211> LENGTH: 6
<212> TYPE: PRT
<213> ORGANISM: Homo sapiens

<400> SEQUENCE: 980

Ile Arg Lys Pro Arg His
1               5

<210> SEQ ID NO 981
<211> LENGTH: 6
<212> TYPE: PRT
<213> ORGANISM: Homo sapiens

<400> SEQUENCE: 981

Val Arg Lys Met Arg Asp
1               5

<210> SEQ ID NO 982
<211> LENGTH: 6
<212> TYPE: PRT
<213> ORGANISM: Homo sapiens

<400> SEQUENCE: 982

Phe Lys Arg Lys Lys Phe
1               5

<210> SEQ ID NO 983
<211> LENGTH: 6
<212> TYPE: PRT
<213> ORGANISM: Homo sapiens

<400> SEQUENCE: 983

Ile Arg Lys Pro Arg His
1               5

```
<210> SEQ ID NO 984
<211> LENGTH: 6
<212> TYPE: PRT
<213> ORGANISM: Homo sapiens

<400> SEQUENCE: 984

Val Arg Lys Met Arg Asp
1               5

<210> SEQ ID NO 985
<211> LENGTH: 6
<212> TYPE: PRT
<213> ORGANISM: Homo sapiens

<400> SEQUENCE: 985

Val Lys Lys Val Arg Leu
1               5

<210> SEQ ID NO 986
<211> LENGTH: 6
<212> TYPE: PRT
<213> ORGANISM: Homo sapiens

<400> SEQUENCE: 986

Val Lys Lys Val Arg Leu
1               5

<210> SEQ ID NO 987
<211> LENGTH: 6
<212> TYPE: PRT
<213> ORGANISM: Homo sapiens

<400> SEQUENCE: 987

Ala Arg Arg Leu Arg Asn
1               5

<210> SEQ ID NO 988
<211> LENGTH: 6
<212> TYPE: PRT
<213> ORGANISM: Homo sapiens

<400> SEQUENCE: 988

Ala Arg Arg Leu Arg Asn
1               5

<210> SEQ ID NO 989
<211> LENGTH: 8
<212> TYPE: PRT
<213> ORGANISM: Homo sapiens

<400> SEQUENCE: 989

Lys Lys Lys Lys Thr Gly Arg Ala
1               5

<210> SEQ ID NO 990
<211> LENGTH: 6
<212> TYPE: PRT
<213> ORGANISM: Homo sapiens

<400> SEQUENCE: 990

Glu Lys Lys Lys Lys Lys
1               5

<210> SEQ ID NO 991
<211> LENGTH: 6
```

```
<212> TYPE: PRT
<213> ORGANISM: Homo sapiens

<400> SEQUENCE: 991

Glu Lys Lys Lys Lys Lys
1               5

<210> SEQ ID NO 992
<211> LENGTH: 6
<212> TYPE: PRT
<213> ORGANISM: Homo sapiens

<400> SEQUENCE: 992

Leu Arg Arg His Lys Arg
1               5

<210> SEQ ID NO 993
<211> LENGTH: 6
<212> TYPE: PRT
<213> ORGANISM: Homo sapiens

<400> SEQUENCE: 993

Leu Arg Arg His Lys Arg
1               5

<210> SEQ ID NO 994
<211> LENGTH: 8
<212> TYPE: PRT
<213> ORGANISM: Homo sapiens

<400> SEQUENCE: 994

Asn Arg Lys Arg Leu Tyr Lys Val
1               5

<210> SEQ ID NO 995
<211> LENGTH: 8
<212> TYPE: PRT
<213> ORGANISM: Homo sapiens

<400> SEQUENCE: 995

Glu Arg Lys Arg Ser Arg Arg Arg
1               5

<210> SEQ ID NO 996
<211> LENGTH: 8
<212> TYPE: PRT
<213> ORGANISM: Homo sapiens

<400> SEQUENCE: 996

Gln Arg Arg Arg Thr Pro Arg Pro
1               5

<210> SEQ ID NO 997
<211> LENGTH: 8
<212> TYPE: PRT
<213> ORGANISM: Homo sapiens

<400> SEQUENCE: 997

Glu Lys Lys Lys Lys Arg Arg Glu
1               5

<210> SEQ ID NO 998
<211> LENGTH: 6
<212> TYPE: PRT
<213> ORGANISM: Homo sapiens
```

```
<400> SEQUENCE: 998

Val Arg Lys Leu Arg Lys
1               5

<210> SEQ ID NO 999
<211> LENGTH: 6
<212> TYPE: PRT
<213> ORGANISM: Homo sapiens

<400> SEQUENCE: 999

Gly Arg Arg Gln Lys Lys
1               5

<210> SEQ ID NO 1000
<211> LENGTH: 6
<212> TYPE: PRT
<213> ORGANISM: Homo sapiens

<400> SEQUENCE: 1000

Thr Lys Lys Gln Lys Arg
1               5

<210> SEQ ID NO 1001
<211> LENGTH: 6
<212> TYPE: PRT
<213> ORGANISM: Homo sapiens

<400> SEQUENCE: 1001

Arg Lys Arg Ser Arg Arg
1               5

<210> SEQ ID NO 1002
<211> LENGTH: 6
<212> TYPE: PRT
<213> ORGANISM: Homo sapiens

<400> SEQUENCE: 1002

Glu Lys Lys Lys Lys Arg
1               5

<210> SEQ ID NO 1003
<211> LENGTH: 6
<212> TYPE: PRT
<213> ORGANISM: Homo sapiens

<400> SEQUENCE: 1003

Val Arg Lys Leu Arg Lys
1               5

<210> SEQ ID NO 1004
<211> LENGTH: 6
<212> TYPE: PRT
<213> ORGANISM: Homo sapiens

<400> SEQUENCE: 1004

Gly Arg Arg Gln Lys Lys
1               5

<210> SEQ ID NO 1005
<211> LENGTH: 6
<212> TYPE: PRT
<213> ORGANISM: Homo sapiens

<400> SEQUENCE: 1005
```

```
Thr Lys Lys Gln Lys Arg
1               5

<210> SEQ ID NO 1006
<211> LENGTH: 6
<212> TYPE: PRT
<213> ORGANISM: Homo sapiens

<400> SEQUENCE: 1006

Arg Lys Arg Ser Arg Arg
1               5

<210> SEQ ID NO 1007
<211> LENGTH: 6
<212> TYPE: PRT
<213> ORGANISM: Homo sapiens

<400> SEQUENCE: 1007

Glu Lys Lys Lys Lys Arg
1               5

<210> SEQ ID NO 1008
<211> LENGTH: 6
<212> TYPE: PRT
<213> ORGANISM: Homo sapiens

<400> SEQUENCE: 1008

Trp Lys Arg Ile Lys Gly
1               5

<210> SEQ ID NO 1009
<211> LENGTH: 6
<212> TYPE: PRT
<213> ORGANISM: Homo sapiens

<400> SEQUENCE: 1009

Trp Lys Arg Ile Lys Gly
1               5

<210> SEQ ID NO 1010
<211> LENGTH: 8
<212> TYPE: PRT
<213> ORGANISM: Homo sapiens

<400> SEQUENCE: 1010

Asn Arg Arg Arg Gln Glu Arg Phe
1               5

<210> SEQ ID NO 1011
<211> LENGTH: 6
<212> TYPE: PRT
<213> ORGANISM: Homo sapiens

<400> SEQUENCE: 1011

Arg Lys Arg Ala Lys Asp
1               5

<210> SEQ ID NO 1012
<211> LENGTH: 6
<212> TYPE: PRT
<213> ORGANISM: Homo sapiens

<400> SEQUENCE: 1012

Arg Lys Arg Ala Lys Asp
```

```
1               5

<210> SEQ ID NO 1013
<211> LENGTH: 8
<212> TYPE: PRT
<213> ORGANISM: Homo sapiens

<400> SEQUENCE: 1013

Leu Arg Lys Lys Leu His Lys Phe
1               5

<210> SEQ ID NO 1014
<211> LENGTH: 6
<212> TYPE: PRT
<213> ORGANISM: Homo sapiens

<400> SEQUENCE: 1014

Ala Arg Lys Asn Lys Asn
1               5

<210> SEQ ID NO 1015
<211> LENGTH: 6
<212> TYPE: PRT
<213> ORGANISM: Homo sapiens

<400> SEQUENCE: 1015

Ala Arg Lys Asn Lys Asn
1               5

<210> SEQ ID NO 1016
<211> LENGTH: 6
<212> TYPE: PRT
<213> ORGANISM: Homo sapiens

<400> SEQUENCE: 1016

Ser Lys Lys Arg Lys Asn
1               5

<210> SEQ ID NO 1017
<211> LENGTH: 6
<212> TYPE: PRT
<213> ORGANISM: Homo sapiens

<400> SEQUENCE: 1017

Ser Lys Lys Arg Lys Asn
1               5

<210> SEQ ID NO 1018
<211> LENGTH: 6
<212> TYPE: PRT
<213> ORGANISM: Homo sapiens

<400> SEQUENCE: 1018

Ser Arg Arg Tyr Arg Gly
1               5

<210> SEQ ID NO 1019
<211> LENGTH: 6
<212> TYPE: PRT
<213> ORGANISM: Homo sapiens

<400> SEQUENCE: 1019

His Arg Lys Asn Lys Pro
1               5
```

```
<210> SEQ ID NO 1020
<211> LENGTH: 6
<212> TYPE: PRT
<213> ORGANISM: Homo sapiens

<400> SEQUENCE: 1020

Ser Arg Arg Tyr Arg Gly
1               5

<210> SEQ ID NO 1021
<211> LENGTH: 6
<212> TYPE: PRT
<213> ORGANISM: Homo sapiens

<400> SEQUENCE: 1021

His Arg Lys Asn Lys Pro
1               5

<210> SEQ ID NO 1022
<211> LENGTH: 8
<212> TYPE: PRT
<213> ORGANISM: Homo sapiens

<400> SEQUENCE: 1022

Ser Arg Arg Arg Phe Arg Lys Ile
1               5

<210> SEQ ID NO 1023
<211> LENGTH: 8
<212> TYPE: PRT
<213> ORGANISM: Homo sapiens

<400> SEQUENCE: 1023

Gln Arg Lys Lys Arg Trp Arg Ser
1               5

<210> SEQ ID NO 1024
<211> LENGTH: 8
<212> TYPE: PRT
<213> ORGANISM: Homo sapiens

<400> SEQUENCE: 1024

His Lys Lys Arg Ala Arg Arg Ser
1               5

<210> SEQ ID NO 1025
<211> LENGTH: 6
<212> TYPE: PRT
<213> ORGANISM: Homo sapiens

<400> SEQUENCE: 1025

Arg Arg Arg Phe Arg Lys
1               5

<210> SEQ ID NO 1026
<211> LENGTH: 6
<212> TYPE: PRT
<213> ORGANISM: Homo sapiens

<400> SEQUENCE: 1026

Ser Lys Lys Val Lys Ala
1               5

<210> SEQ ID NO 1027
```

```
<211> LENGTH: 6
<212> TYPE: PRT
<213> ORGANISM: Homo sapiens

<400> SEQUENCE: 1027

Leu Lys Arg Met Lys Ile
1               5

<210> SEQ ID NO 1028
<211> LENGTH: 6
<212> TYPE: PRT
<213> ORGANISM: Homo sapiens

<400> SEQUENCE: 1028

Gln Arg Lys Lys Arg Trp
1               5

<210> SEQ ID NO 1029
<211> LENGTH: 6
<212> TYPE: PRT
<213> ORGANISM: Homo sapiens

<400> SEQUENCE: 1029

Lys Lys Arg Ala Arg Arg
1               5

<210> SEQ ID NO 1030
<211> LENGTH: 6
<212> TYPE: PRT
<213> ORGANISM: Homo sapiens

<400> SEQUENCE: 1030

Ala Arg Lys Val Lys Gln
1               5

<210> SEQ ID NO 1031
<211> LENGTH: 6
<212> TYPE: PRT
<213> ORGANISM: Homo sapiens

<400> SEQUENCE: 1031

Arg Arg Arg Phe Arg Lys
1               5

<210> SEQ ID NO 1032
<211> LENGTH: 6
<212> TYPE: PRT
<213> ORGANISM: Homo sapiens

<400> SEQUENCE: 1032

Ser Lys Lys Val Lys Ala
1               5

<210> SEQ ID NO 1033
<211> LENGTH: 6
<212> TYPE: PRT
<213> ORGANISM: Homo sapiens

<400> SEQUENCE: 1033

Leu Lys Arg Met Lys Ile
1               5

<210> SEQ ID NO 1034
<211> LENGTH: 6
<212> TYPE: PRT
```

<213> ORGANISM: Homo sapiens

<400> SEQUENCE: 1034

Gln Arg Lys Lys Arg Trp
1               5

<210> SEQ ID NO 1035
<211> LENGTH: 6
<212> TYPE: PRT
<213> ORGANISM: Homo sapiens

<400> SEQUENCE: 1035

Lys Lys Arg Ala Arg Arg
1               5

<210> SEQ ID NO 1036
<211> LENGTH: 6
<212> TYPE: PRT
<213> ORGANISM: Homo sapiens

<400> SEQUENCE: 1036

Ala Arg Lys Val Lys Gln
1               5

<210> SEQ ID NO 1037
<211> LENGTH: 8
<212> TYPE: PRT
<213> ORGANISM: Homo sapiens

<400> SEQUENCE: 1037

Glu Arg Lys Lys Ile Thr Arg Glu
1               5

<210> SEQ ID NO 1038
<211> LENGTH: 6
<212> TYPE: PRT
<213> ORGANISM: Homo sapiens

<400> SEQUENCE: 1038

Gly Arg Lys Arg Lys Glu
1               5

<210> SEQ ID NO 1039
<211> LENGTH: 6
<212> TYPE: PRT
<213> ORGANISM: Homo sapiens

<400> SEQUENCE: 1039

Gly Arg Lys Arg Lys Glu
1               5

<210> SEQ ID NO 1040
<211> LENGTH: 6
<212> TYPE: PRT
<213> ORGANISM: Homo sapiens

<400> SEQUENCE: 1040

Leu Lys Arg Pro Arg Leu
1               5

<210> SEQ ID NO 1041
<211> LENGTH: 6
<212> TYPE: PRT
<213> ORGANISM: Homo sapiens

```
<400> SEQUENCE: 1041

Val Lys Arg Glu Lys Pro
1               5

<210> SEQ ID NO 1042
<211> LENGTH: 6
<212> TYPE: PRT
<213> ORGANISM: Homo sapiens

<400> SEQUENCE: 1042

Leu Lys Arg Pro Arg Leu
1               5

<210> SEQ ID NO 1043
<211> LENGTH: 6
<212> TYPE: PRT
<213> ORGANISM: Homo sapiens

<400> SEQUENCE: 1043

Val Lys Arg Glu Lys Pro
1               5

<210> SEQ ID NO 1044
<211> LENGTH: 6
<212> TYPE: PRT
<213> ORGANISM: Homo sapiens

<400> SEQUENCE: 1044

Ser Lys Arg Pro Lys Thr
1               5

<210> SEQ ID NO 1045
<211> LENGTH: 6
<212> TYPE: PRT
<213> ORGANISM: Homo sapiens

<400> SEQUENCE: 1045

Glu Lys Lys Asn Lys Leu
1               5

<210> SEQ ID NO 1046
<211> LENGTH: 6
<212> TYPE: PRT
<213> ORGANISM: Homo sapiens

<400> SEQUENCE: 1046

Asn Lys Arg Pro Arg Thr
1               5

<210> SEQ ID NO 1047
<211> LENGTH: 6
<212> TYPE: PRT
<213> ORGANISM: Homo sapiens

<400> SEQUENCE: 1047

Asp Lys Arg Leu Arg Thr
1               5

<210> SEQ ID NO 1048
<211> LENGTH: 6
<212> TYPE: PRT
<213> ORGANISM: Homo sapiens

<400> SEQUENCE: 1048
```

```
Gln Lys Arg Phe Arg Thr
1               5

<210> SEQ ID NO 1049
<211> LENGTH: 6
<212> TYPE: PRT
<213> ORGANISM: Homo sapiens

<400> SEQUENCE: 1049

Glu Lys Lys Ser Lys Leu
1               5

<210> SEQ ID NO 1050
<211> LENGTH: 6
<212> TYPE: PRT
<213> ORGANISM: Homo sapiens

<400> SEQUENCE: 1050

Gln Arg Lys Asp Lys Asp
1               5

<210> SEQ ID NO 1051
<211> LENGTH: 6
<212> TYPE: PRT
<213> ORGANISM: Homo sapiens

<400> SEQUENCE: 1051

Pro Lys Lys Glu Lys Gly
1               5

<210> SEQ ID NO 1052
<211> LENGTH: 6
<212> TYPE: PRT
<213> ORGANISM: Homo sapiens

<400> SEQUENCE: 1052

Ser Lys Arg Pro Lys Thr
1               5

<210> SEQ ID NO 1053
<211> LENGTH: 6
<212> TYPE: PRT
<213> ORGANISM: Homo sapiens

<400> SEQUENCE: 1053

Glu Lys Lys Asn Lys Leu
1               5

<210> SEQ ID NO 1054
<211> LENGTH: 6
<212> TYPE: PRT
<213> ORGANISM: Homo sapiens

<400> SEQUENCE: 1054

Asn Lys Arg Pro Arg Thr
1               5

<210> SEQ ID NO 1055
<211> LENGTH: 6
<212> TYPE: PRT
<213> ORGANISM: Homo sapiens

<400> SEQUENCE: 1055

Asp Lys Arg Leu Arg Thr
1               5
```

```
<210> SEQ ID NO 1056
<211> LENGTH: 6
<212> TYPE: PRT
<213> ORGANISM: Homo sapiens

<400> SEQUENCE: 1056

Gln Lys Arg Phe Arg Thr
1               5

<210> SEQ ID NO 1057
<211> LENGTH: 6
<212> TYPE: PRT
<213> ORGANISM: Homo sapiens

<400> SEQUENCE: 1057

Glu Lys Lys Ser Lys Leu
1               5

<210> SEQ ID NO 1058
<211> LENGTH: 6
<212> TYPE: PRT
<213> ORGANISM: Homo sapiens

<400> SEQUENCE: 1058

Gln Arg Lys Asp Lys Asp
1               5

<210> SEQ ID NO 1059
<211> LENGTH: 6
<212> TYPE: PRT
<213> ORGANISM: Homo sapiens

<400> SEQUENCE: 1059

Pro Lys Lys Glu Lys Gly
1               5

<210> SEQ ID NO 1060
<211> LENGTH: 6
<212> TYPE: PRT
<213> ORGANISM: Homo sapiens

<400> SEQUENCE: 1060

Tyr Lys Arg Arg Lys Lys
1               5

<210> SEQ ID NO 1061
<211> LENGTH: 6
<212> TYPE: PRT
<213> ORGANISM: Homo sapiens

<400> SEQUENCE: 1061

Tyr Lys Arg Arg Lys Lys
1               5

<210> SEQ ID NO 1062
<211> LENGTH: 6
<212> TYPE: PRT
<213> ORGANISM: Homo sapiens

<400> SEQUENCE: 1062

Thr Arg Arg Glu Arg Ala
1               5
```

```
<210> SEQ ID NO 1063
<211> LENGTH: 6
<212> TYPE: PRT
<213> ORGANISM: Homo sapiens

<400> SEQUENCE: 1063

His Arg Lys Leu Lys Val
1               5

<210> SEQ ID NO 1064
<211> LENGTH: 6
<212> TYPE: PRT
<213> ORGANISM: Homo sapiens

<400> SEQUENCE: 1064

Thr Arg Arg Glu Arg Ala
1               5

<210> SEQ ID NO 1065
<211> LENGTH: 6
<212> TYPE: PRT
<213> ORGANISM: Homo sapiens

<400> SEQUENCE: 1065

His Arg Lys Leu Lys Val
1               5

<210> SEQ ID NO 1066
<211> LENGTH: 6
<212> TYPE: PRT
<213> ORGANISM: Homo sapiens

<400> SEQUENCE: 1066

Pro Lys Lys Pro Lys Gly
1               5

<210> SEQ ID NO 1067
<211> LENGTH: 6
<212> TYPE: PRT
<213> ORGANISM: Homo sapiens

<400> SEQUENCE: 1067

Gly Lys Lys Lys Lys Asp
1               5

<210> SEQ ID NO 1068
<211> LENGTH: 6
<212> TYPE: PRT
<213> ORGANISM: Homo sapiens

<400> SEQUENCE: 1068

Pro Lys Lys Pro Lys Gly
1               5

<210> SEQ ID NO 1069
<211> LENGTH: 6
<212> TYPE: PRT
<213> ORGANISM: Homo sapiens

<400> SEQUENCE: 1069

Gly Lys Lys Lys Lys Asp
1               5

<210> SEQ ID NO 1070
<211> LENGTH: 4
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1070

Arg Arg Lys Arg
1

<210> SEQ ID NO 1071
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1071

Phe Phe Lys Lys
1

<210> SEQ ID NO 1072
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1072

Lys Lys Lys Lys
1

<210> SEQ ID NO 1073
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1073

Arg Arg Arg Lys
1

<210> SEQ ID NO 1074
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1074

Arg Arg Lys Asn
1
```